US009278966B2

(12) United States Patent
Sunagawa et al.

(10) Patent No.: US 9,278,966 B2
(45) Date of Patent: Mar. 8, 2016

(54) METHOD FOR MANUFACTURING OXETANE COMPOUND, METHOD FOR MANUFACTURING AZOLYLMETHYLCYCLOPENTANOL COMPOUND, AND INTERMEDIATE COMPOUND

(75) Inventors: Kazuhiko Sunagawa, Tokyo (JP); Toru Yamazaki, Tokyo (JP); Emiko Obata, Tokyo (JP)

(73) Assignee: KUREHA CORPORATION, Tokyo (JP)

( * ) Notice: Subject to any disclaimer, the term of this patent is extended or adjusted under 35 U.S.C. 154(b) by 0 days.

(21) Appl. No.: 14/124,114

(22) PCT Filed: Jun. 6, 2012

(86) PCT No.: PCT/JP2012/064601

§ 371 (c)(1), (2), (4) Date: Dec. 5, 2013

(87) PCT Pub. No.: WO2012/169555

PCT Pub. Date: Dec. 13, 2012

(65) Prior Publication Data

US 2014/0128611 A1 May 8, 2014

(30) Foreign Application Priority Data

Jun. 7, 2011 (JP) ................................ 2011-127766

(51) Int. Cl.

| | |
|---|---|
| ***C07D 401/00*** | (2006.01) |
| ***C07D 277/22*** | (2006.01) |
| ***C07D 277/30*** | (2006.01) |
| ***C07D 249/08*** | (2006.01) |
| ***C07D 305/00*** | (2006.01) |
| ***C07D 407/00*** | (2006.01) |
| ***C07D 493/00*** | (2006.01) |
| ***C07D 417/14*** | (2006.01) |
| ***C07D 333/28*** | (2006.01) |
| ***C07C 309/66*** | (2006.01) |
| ***C07C 309/73*** | (2006.01) |
| ***C07D 401/08*** | (2006.01) |
| ***C07D 405/06*** | (2006.01) |
| ***C07D 409/06*** | (2006.01) |
| ***C07D 409/08*** | (2006.01) |
| ***C07D 417/06*** | (2006.01) |
| ***C07D 417/08*** | (2006.01) |
| ***C07D 277/20*** | (2006.01) |
| ***C07D 277/32*** | (2006.01) |

(Continued)

(52) U.S. Cl.

CPC ............ *C07D 417/14* (2013.01); *C07C 309/66* (2013.01); *C07C 309/73* (2013.01); *C07D 213/61* (2013.01); *C07D 249/08* (2013.01); *C07D 277/20* (2013.01); *C07D 277/32* (2013.01); *C07D 305/14* (2013.01); *C07D 333/28* (2013.01); *C07D 401/08* (2013.01); *C07D 405/06* (2013.01); *C07D 405/14* (2013.01); *C07D 409/06* (2013.01); *C07D 409/08* (2013.01); *C07D 417/06* (2013.01); *C07D 417/08* (2013.01); *C07C 2101/08* (2013.01)

(58) Field of Classification Search

None

See application file for complete search history.

(56) References Cited

U.S. PATENT DOCUMENTS 3,871,964 A 3/1975 Huper et al.
4,938,792 A 7/1990 Kumazawa et al.

(Continued)

FOREIGN PATENT DOCUMENTS

CN 1030232 A 1/1989
CN 1137789 A 12/1996

(Continued)

OTHER PUBLICATIONS

Johnstone, RA. et al. Heterogeneous Catalytic Transfer Hydrogenation and Its Relation to Other Methods for Reduction of Organic Compounds. Chem. Rev. 1985, vol. 85, p. 141.*

(Continued)

*Primary Examiner* — Janet L Andres
*Assistant Examiner* — Ben S Michelson
(74) *Attorney, Agent, or Firm* — Birch, Stewart, Kolasch & Birch, LLP

(57) ABSTRACT

In order to produce an intermediate from which a cyclic alcohol compound can be stereoselectively obtained, a method for producing an oxetane compound according to the present invention includes the step of reacting, with a cyanide salt, a compound represented by Formula (I):

(I)

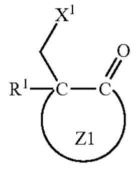

wherein $R^1$ is selected from a hydrogen atom and an alkyl group optionally having a substituent; $X^1$ is selected from a halogen atom and —$OSO_2R^3$ where $R^3$ is selected from an alkyl group optionally having a substituent, a phenyl group, and a naphthyl group; and a ring Z1 represents a cyclic hydrocarbon optionally having a substituent, to obtain a compound represented by Formula (II):

(II)

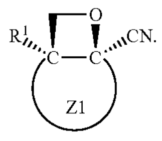

12 Claims, No Drawings

(51) Int. Cl.
*C07D 213/61* (2006.01)
*C07D 305/14* (2006.01)
*C07D 405/14* (2006.01)

(56) References Cited

U.S. PATENT DOCUMENTS

| | | | |
|---|---|---|---|
| 5,028,254 | A | 7/1991 | Kumazawa et al. |
| 5,159,118 | A | 10/1992 | Kumazawa et al. |
| 5,239,089 | A | 8/1993 | Kumazawa et al. |
| 5,405,972 | A | 4/1995 | Holton et al. |
| 5,414,105 | A | 5/1995 | Kumazawa et al. |
| 5,618,952 | A | 4/1997 | Holton et al. |
| 5,637,732 | A | 6/1997 | Holton et al. |
| 5,760,252 | A | 6/1998 | Holton et al. |
| 6,005,120 | A | 12/1999 | Holton et al. |
| 6,278,026 | B1 | 8/2001 | Holton et al. |
| 6,420,364 | B1 | 7/2002 | Emmanuel et al. |
| 6,515,152 | B1 | 2/2003 | Annby et al. |
| 7,166,750 | B1 | 1/2007 | Sunagawa et al. |
| 2001/0053857 | A1 | 12/2001 | Holton et al. |
| 2002/0137932 | A1 | 9/2002 | Bekkali et al. |
| 2003/0050485 | A1 | 3/2003 | Holton et al. |
| 2010/0261766 | A1 | 10/2010 | Albert et al. |
| 2014/0107372 | A1 | 4/2014 | Kanno |

FOREIGN PATENT DOCUMENTS

| | | | |
|---|---|---|---|
| CN | 1333763 | A | 1/2002 |
| CN | 1384830 | A | 12/2002 |
| CN | 1454200 | A | 11/2003 |
| CN | 101638399 | A | 2/2010 |
| CN | 101878205 | A | 11/2010 |
| DE | 3902031 | A1 | 7/1990 |
| EP | 0 537 909 | B1 | 1/1997 |
| EP | 2 719 681 | A1 | 4/2014 |
| FR | 1379787 | A | 10/1964 |
| JP | 2004-115526 | A | 4/2004 |
| WO | WO 02/00608 | A2 | 1/2002 |
| WO | WO 2011/070771 | A1 | 6/2011 |
| WO | WO 2012/169468 | A1 | 12/2012 |

OTHER PUBLICATIONS

Dorwold, FZ. Side Reactions in Organic Synthesis. Wiley. 2005, preface.*

Extended European Search Report issued Sep. 29, 2014, in European Patent Application No. 12796110.0.

First Office Action issued Sep. 28, 2014, in Chinese Patent Application No. 201280026438.6, with English Translation.

Searls et al., "The Reaction of Trimethylene Oxide with Amines," O. Hromatka, Ber., (May 20, 1954), vol. 75B, pp. 2789-2790.

Ye et al., "Cationic Ring-opening Polymerization of Substituted Oxetane Monomers," Journal of Functional Polymers (Dec. 2005), vol. 18, No. 4, pp. 653-654 (with English abstract).

Bottger, D. and P. Welzel, "Synthesis of the C25 alcohol moenocinol. Studies of . . . ," Liebigs Annalen der Chemie (1985), pp. 837-852.

Burkhard et al., "Oxetanes as Versalite Elements in Drug Discovery and Synthesis," Agnew. Chem. Ind. Ed. (2010), vol. 49, pp. 9052-9067.

Cizmarikova et al., "Reaction of the 2,2,5,5-tetrakis (hydroxymethyl) cyclopentanone tosyl ether and . . . ," Zeitschrift fuer Chemie (1978), vol. 18, No. 10, pp. 380-381.

English translation of International Preliminary Report on Patentability and Written Opinion issued Dec. 27, 2013, in PCT International Application No. PCT/JP2012/064601.

Fitton et al., "2-Substituted 3,3-Diethyloxetanes," J. Chem. Research (S) (1989), p. 337.

Fitton et al., "2-Substituted 3,3-Diethyloxetanes," J. Chem. Research Miniprint (1989), pp. 2740-2750.

International Search Report issued Jul. 24, 2012, in PCT International Application No. PCT/JP2012/064601.

Lucas et al., "Fragmentation reactions of carbonyl . . . ," Chemische Berichte (1971), vol. 104, No. 11, pp. 3607-3617.

Sulmon et al., "Synthesis of Azetidines from β-chloro Imines," Tetrahedron (1988), vol. 44, No. 12, pp. 3653-3670.

Takahashi et al., "Ring Opening of Aryl Cyclopropyl Ketones to 1-Acyl-1,1-3-tribromopropanes and their Cyclization to . . . ," J. Heterocyclic Chem. (1983), vol. 20, pp. 209-211.

Chinese Office Action dated Jun. 25, 2015 for Chinese Application No. 201280026438.6 with English Translation.

European Office Communication for European Application No. 12796110.0, dated Oct. 7, 2015.

Japanese Office Action for Japanese Application No. 2013-519516, dated Sep. 15, 2015, with an English translation.

Chinese Office Action for Application No. 201510079726.3 dated Dec. 18, 2015 with English language translation.

Yingxiang, Liu et al., "Design, synthesis and antitumor activity of substituted benzylidenecyclopentanone derivatives", Chinese J. of Medicinal Chemistry, vol. 20, No. 1, Feb. 28, 2010, pp. 11-18.

* cited by examiner

METHOD FOR MANUFACTURING OXETANE COMPOUND, METHOD FOR MANUFACTURING AZOLYLMETHYLCYCLOPENTANOL COMPOUND, AND INTERMEDIATE COMPOUND

TECHNICAL FIELD

The present invention relates to: a method for producing an oxetane compound; a method for producing an azolylmethylcyclopentanol compound, which method employs the method for producing an oxetane compound; an intermediate compound employed in any of these production methods; and an intermediate compound obtained by any of these production methods.

BACKGROUND ART

Conventionally, a typical method for forming an oxetane ring includes: a method of coupling a hydroxy group with a methyl group, adjacent to the hydroxy group, having a leaving group; and a method of adding a double-bond compound to a carbonyl compound (see Non-patent Literature 1). Other examples of the method for forming an oxetane ring include: a method of reacting an aldehyde with a cyanide (see Non-Patent Literatures 2 and 3); a method of reacting a haloalkyl ketone with a cyanide (see Non-Patent Literature 4); and a method of refluxing diol mesylate or diol tosylate in a base (see Patent Literature 1).

CITATION LIST

Patent Literature

Patent Literature 1

Japanese Patent Application Publication, Tokukai, No. 2004-115526 A (published on Apr. 15, 2004)

Non-Patent Literatures

Non-Patent Literature 1

Johannes A. Burkhard, Georg Wuitschik, Mark Roger-Evans, Klaus Muller, and Erick M. Carreira, Angew. Chem. Int. Ed., 2010, 49, 9052.

Non-Patent Literature 2

Alan O. Fitton, John Hill, David E. Jane, and Ross Millar, J. Chem. Research Synopses, 1989, 337.

Non-Patent Literature 3

Alan O. Fitton, John Hill, David E. Jane, and Ross Millar, J. Chem. Research Miniprint, 1989, 2740-2750.

Non-Patent Literature 4

Masahiko Takahashi, Noriaki Takeshi, Kohji Myojoh, Hideyuki Sano, and Toshio Morisawa, J of Heterocyclic Chemistry, 1983, 209.

SUMMARY OF INVENTION

Technical Problem

In a hydrocarbon having a cyclic structure, there may be cases where a geometrical isomerism due to the organic groups bonded to the cyclic structure is problematic. In a case where the cyclic hydrocarbon and an oxetane ring form a condensed ring, two functional groups bonded to the cyclic hydrocarbon are obtained by opening of the oxetane ring. Both of these functional groups take a cis configuration.

Therefore, if it is possible to selectively synthesize an oxetane compound, the steric configuration of the adjacent functional groups resulting from the ring opening can be controlled to be a cis configuration.

According to the production methods described in Non-Patent Literatures 1 and 2 listed above, oxetane compounds obtained by the methods are not arranged such that a specific geometrical isomer is selectively obtained by opening of an oxetane ring of the oxetane compound. The method described in Patent Literature 1 listed above discloses an oxetane compound wherein steric configurations of functional groups obtained by opening of an oxetane ring thereof are preselected before the opening of the oxetane ring thereof.

In view of this problem, an object of the present invention is to provide (i) a novel intermediate compound used to selectively obtain a specific geometrical isomer and (ii) a method for producing such an intermediate compound.

Solution to Problem

A method for producing an oxetane compound, according to the present invention, is a method for producing an oxetane compound represented by Formula (II) shown below, comprising the step of:

reacting, with a cyanide salt, a compound represented by Formula (I):

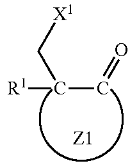

(I)

wherein $R^1$ is selected from a hydrogen atom and a linear or branched $C_1$-$C_6$ alkyl group; a hydrogen atom(s) contained in the alkyl group may be substituted with a $C_1$-$C_4$ alkoxy group; $X^1$ is selected from a halogen atom and —$OSO_2R^3$ where $R^3$ is selected from a $C_1$-$C_3$ alkyl group, a phenyl group, and a naphthyl group, and a hydrogen atom(s) contained in any one of the alkyl group, the phenyl group, and the naphthyl group may be substituted; and a ring Z1 represents a $C_5$-$C_8$ cyclic hydrocarbon having a ring structure which includes (i) a carbon atom bonded to $R^1$ and (ii) a carbonyl carbon atom, where a hydrogen atom(s) contained in the cyclic hydrocarbon may be substituted, to obtain the oxetane compound represented by Formula (II):

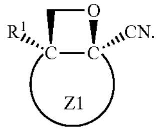

(II)

wherein $R^1$ and a ring Z1 are identical to $R^1$ and the ring Z1 in Formula (I), respectively.

A method for producing an oxetane compound, according to the present invention, is a method for producing an oxetane compound represented by Formula (V) shown below, comprising the steps of:

reacting, with a cyanide salt, a compound represented by Formula (III):

(III)

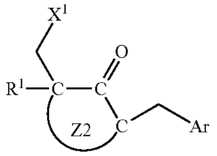

wherein $R^1$ is selected from a hydrogen atom and a linear or branched $C_1$-$C_6$ alkyl group; a hydrogen atom(s) contained in the alkyl group may be substituted with a $C_1$-$C_4$ alkoxy group; $X^1$ is selected from a halogen atom and —$OSO_2R^3$ where $R^3$ is selected from a $C_1$-$C_3$ alkyl group, a phenyl group, and a naphthyl group, and a hydrogen atom(s) contained in any one of the alkyl group, the phenyl group, and the naphthyl group may be substituted; Ar is selected from a $C_6$-$C_{10}$ aromatic hydrocarbon group having a hydrogen atom(s) which may be substituted and a 5 to 10-membered aromatic heterocyclic group having a hydrogen atom(s) which may be substituted; and a ring Z2 represents a $C_5$-$C_8$ cyclic hydrocarbon having a ring structure which includes (i) a carbon atom bonded to $R^1$, (ii) a carbonyl carbon atom, and (iii) a carbon atom bonded to —$CH_2$—Ar, where a hydrogen atom(s) contained in the cyclic hydrocarbon may be substituted, to obtain an oxetane compound represented by Formula (IV):

(IV)

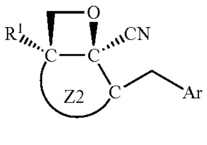

wherein $R^1$, a ring Z2, and Ar are identical to $R^1$, the ring Z2, and Ar in Formula (III) shown above, respectively; and reacting the oxetane compound represented by Formula (IV) shown above with an alkoxide, to obtain the oxetane compound represented by Formula (V):

(V)

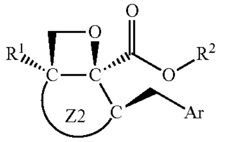

wherein $R^1$, a ring Z2, and Ar are identical to $R^1$, the ring Z2, and Ar in Formula (III) shown above, respectively, and $R^2$ represents a linear or branched $C_1$-$C_6$ alkyl group. A method for producing an azolylmethylcyclopentanol compound, according to the present invention, is a method for producing an azolylmethylcyclopentanol compound, comprising the aforementioned method for producing an oxetane compound, wherein the compound represented by Formula (I) is a compound represented by Formula (4):

(4)

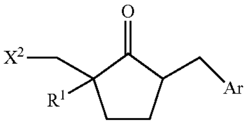

wherein $R^1$ represents a linear or branched $C_1$-$C_6$ alkyl group; a hydrogen atom(s) contained in the alkyl group may be substituted with a $C_1$-$C_4$ alkoxy group; $X^2$ is selected from a halogen atom and —$OSO_2R^3$ where $R^3$ is selected from a $C_1$-$C_3$ alkyl group, a phenyl group, and a naphthyl group, and a hydrogen atom(s) contained in any one of the alkyl group, the phenyl group, and the naphthyl group may be substituted; and Ar is selected from a $C_6$-$C_{10}$ aromatic hydrocarbon group having a hydrogen atom(s) which may be substituted and a 5 to 10-membered aromatic heterocyclic group having a hydrogen atom(s) which may be substituted;

the compound represented by Formula (II) is a compound represented by Formula (5):

(5)

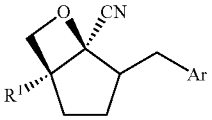

wherein $R^1$ and Ar are identical to $R^1$ and Ar in Formula (4) shown above, respectively; and the azolylmethylcyclopentanol compound is represented by Formula (11):

(11)

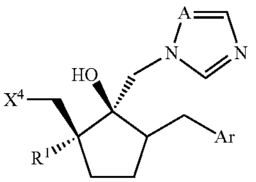

wherein $R^1$ and Ar are identical to $R^1$ and Ar in Formula (4), respectively, $X^4$ represents a halogen atom, and A is selected from a nitrogen atom and a methine group.

A method for producing an azolylmethylcyclopentanol compound, according to the present invention, is a method for producing an azolylmethylcyclopentanol compound represented by Formula (11a):

(11a)

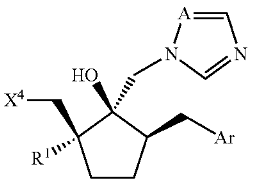

wherein $R^1$ and Ar are identical to $R^1$ and Ar in Formula (4), respectively, $X^4$ represents a halogen atom, and A is selected from a nitrogen atom and a methine group, the method comprising the aforementioned method for producing an oxetane compound.

An intermediate compound according to the present invention is an intermediate compound represented by Formula (5):

(5)

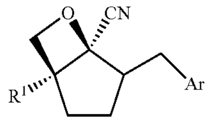

wherein $R^1$ represents a linear or branched $C_1$-$C_6$ alkyl group, a hydrogen atom(s) contained in the alkyl group may be substituted with a $C_1$-$C_4$ alkoxy group, and Ar is selected from: a $C_6$-$C_{10}$ aromatic hydrocarbon group having a hydrogen atom(s) which may be substituted; and a 5 to 10-membered aromatic heterocyclic group having a hydrogen atom(s) which may be substituted.

An intermediate compound according to the present invention is an intermediate compound represented by Formula (6a):

(6a)

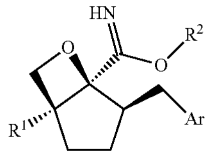

wherein $R^1$ represents a linear or branched $C_1$-$C_6$ alkyl group, a hydrogen atom(s) contained in the alkyl group may be substituted with a $C_1$-$C_4$ alkoxy group, Ar is selected from: a $C_6$-$C_{10}$ aromatic hydrocarbon group having a hydrogen atom(s) which may be substituted; and a 5 to 10-membered aromatic heterocyclic group having a hydrogen atom(s) which may be substituted, and $R^2$ represents a linear or branched $C_1$-$C_6$ alkyl group.

An intermediate compound according to the present invention is an intermediate compound represented by Formula (12):

(12)

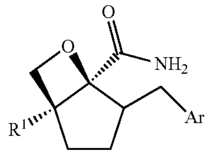

wherein $R^1$ represents a linear or branched $C_1$-$C_6$ alkyl group, a hydrogen atom(s) contained in the alkyl group may be substituted with a $C_1$-$C_4$ alkoxy group, and Ar is selected from: a $C_6$-$C_{10}$ aromatic hydrocarbon group having a hydrogen atom(s) which may be substituted; and a 5 to 10-membered aromatic heterocyclic group having a hydrogen atom(s) which may be substituted.

An intermediate compound according to the present invention is an intermediate compound represented by Formula (15):

(15)

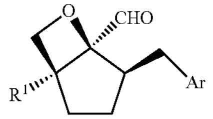

wherein $R^1$ represents a linear or branched $C_1$-$C_6$ alkyl group, a hydrogen atom(s) contained in the alkyl group may be substituted with a $C_1$-$C_4$ alkoxy group, and Ar is selected from: a $C_6$-$C_{10}$ aromatic hydrocarbon group having a hydrogen atom(s) which may be substituted; and a 5 to 10-membered aromatic heterocyclic group having a hydrogen atom(s) which may be substituted.

An intermediate compound according to the present invention is an intermediate compound represented by Formula (4):

(4)

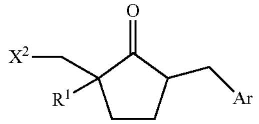

wherein $R^1$ represents a linear or branched $C_1$-$C_6$ alkyl group; a hydrogen atom(s) contained in the alkyl group may be substituted with a $C_1$-$C_4$ alkoxy group; $X^2$ is selected from a halogen atom and —$OSO_2R^3$ where $R^3$ is selected from a $C_1$-$C_3$ alkyl group, a phenyl group and a naphthyl group, and a hydrogen atom(s) contained in any one of the alkyl group, the phenyl group, and the naphthyl group may be substituted; and Ar is selected from a $C_6$-$C_{10}$ aromatic hydrocarbon group having a hydrogen atom(s) which may be substituted and a 5 to 10-membered aromatic heterocyclic group having a hydrogen atom(s) which may be substituted.

Advantageous Effects of Invention

According to a method for producing an oxetane compound according to the present invention, it is possible to suitably produce an intermediate compound from which a specific geometrical isomer of a cyclic alcohol compound can be selectively obtained. Further, according to a method for producing an azolylmethylcyclopentanol compound according to the present invention, which method includes the method for producing an oxetane compound, it is possible to selectively produce a specific geometrical isomer of azolylmethylcyclopentanol. Still further, with use of an intermediate compound according to the present invention, it is possible to selectively produce a specific geometrical isomer of a cyclic alcohol compound.

DESCRIPTION OF EMBODIMENTS

The following will describe a method for producing an oxetane compound, a method for producing an azolylmethylcyclopentanol compound, and an intermediate compound, according to the present invention.

[Method 1 for Producing Oxetane Compound]

According to the present invention, a method for producing an oxetane compound represented by Formula (II) shown below includes the step of reacting, with a cyanide salt, a compound represented by Formula (I):

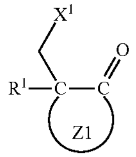

(I)

wherein $R^1$ is selected from a hydrogen atom and a linear or branched $C_1$-$C_6$ alkyl group; a hydrogen atom(s) contained in the alkyl group may be substituted with a $C_1$-$C_4$ alkoxy group; $X^1$ is selected from a halogen atom and —$OSO_2R^3$ where $R^3$ is selected from a $C_1$-$C_3$ alkyl group, a phenyl group, and a naphthyl group, and a hydrogen atom(s) contained in any one of the alkyl group, the phenyl group, and the naphthyl group may be substituted; and a ring Z1 represents a $C_5$-$C_8$ cyclic hydrocarbon having a ring structure which includes (i) a carbon atom bonded to $R^1$ and (ii) a carbonyl carbon atom, where a hydrogen atom(s) contained in the cyclic hydrocarbon may be substituted, to obtain an oxetane compound represented by Formula (II):

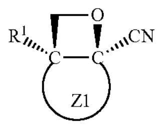

(II)

wherein $R^1$ and a ring Z1 are identical to $R^1$ and the ring Z1 in Formula (I), respectively.

In Formula (I), $R^1$ is selected from a hydrogen atom and a linear or branched $C_1$-$C_6$ alkyl group. Specific examples of the linear or branched $C_1$-$C_6$ alkyl group include a methyl group, an ethyl group, an n-propyl group, an isopropyl group, a 1-methylpropyl group, a 2-methylpropyl group, an n-butyl group, a 1-methylbutyl group, a 2-methylbutyl group, a 1-ethylpropyl group, and 1,1-dimethylethyl group. Especially, a $C_1$-$C_4$ alkyl group is preferable.

A hydrogen atom(s) contained in the alkyl group may be substituted with a $C_1$-$C_4$ alkoxy group. Specific examples of the $C_1$-$C_4$ alkoxy group include a methoxy group, an ethoxy group, and an n-propoxy group. The number of hydrogen atoms to be substituted is not limited and can be one or more.

$X^1$ is selected from a halogen atom and —$OSO_2R^3$ where $R^3$ is selected from a $C_1$-$C_3$ alkyl group, a phenyl group, and a naphthyl group.

Specific examples of the $C_1$-$C_3$ alkyl group as $R^3$ include a methyl group, an ethyl group, an n-propyl group, and an isopropyl group. Especially, a methyl group is preferable. In the $C_1$-$C_3$ alkyl group, a hydrogen atom may be substituted with a halogen atom. Specific examples of the halogen atom include a fluorine atom, a chlorine atom, a bromine atom, and an iodine atom. Among these atoms, a fluorine atom or a chlorine atom is preferable.

In the phenyl group and the naphthyl group both of which can serve as $R^3$, a hydrogen atom may be substituted with a halogen atom, a methyl group, a trifluoromethyl group, a nitro group, or an amino group. Examples of the halogen atom to substitute for the hydrogen atom include a fluorine atom, a chlorine atom, a bromine atom, and an iodine atom.

As —$OSO_2R^3$, any group may be used without particular limitation as long as it falls under the above definition. Examples of —$OSO_2R^3$ include a methanesulfonyloxy group, a propanesulfonyloxy group, a trifluoromethanesulfonyloxy group, a benzenesulfonyloxy group, a chlorobenzenesulfonyloxy group, a p-toluenesulfonyloxy group, a naphthalenesulfonyloxy group, an o-nitrobenzenesulfonyloxy group, and a dimethylaminonaphthylsulfonyloxy group. Especially, a methanesulfonyloxy group and a p-toluenesulfonyloxy group are preferable.

The halogen atom serving as $X^1$ is preferably a chlorine atom or a bromine atom.

The ring Z1 represents a $C_5$-$C_8$ cyclic hydrocarbon having a ring structure which includes (i) a carbon atom bonded to $R^1$ and (ii) a carbonyl carbon atom. The ring Z1 is preferably a $C_5$-$C_7$ cyclic hydrocarbon, and especially preferably a $C_5$ cyclic hydrocarbon (cyclopentane ring). It should be noted that the number of carbon atoms specified here is the number of carbon atoms including the carbon atom bonded to $R^1$ and the carbonyl carbon atom. Further, a hydrogen atom(s) contained in the cyclic hydrocarbon may be substituted with a substituent. Examples of the substituent in the cyclic hydrocarbon include: an aliphatic hydrocarbon group; an aromatic hydrocarbon group; an aromatic heterocyclic group; an aliphatic hydrocarbon group in which a hydrogen atom is substituted with an aromatic hydrocarbon group or an aromatic heterocyclic group; an alkoxylalkyl group; a carbonyloxyalkyl group; and an amido group. Moreover, hydrogen atoms contained in these substituents may be each substituted with a halogen atom; an alkoxy group; an alkyl group; a haloalkyl group; an aromatic hydrocarbon group; an aromatic heterocyclic group; and the like. Further, in a case where there are a plurality of substituents in the ring Z1, the substituents may form another ring structure, in addition to the ring Z1, together with respective carbon atoms bonded to the substituents.

The substituent of the ring Z1 is preferably exemplified by —$CH_2$—Ar. Ar of —$CH_2$—Ar is selected from: a $C_6$-$C_{10}$ aromatic hydrocarbon group having a hydrogen atom(s) which may be substituted; and a 5 to 10-membered aromatic heterocyclic group having a hydrogen atom(s) which may be substituted.

Examples of the $C_6$-$C_{10}$ aromatic hydrocarbon group serving as Ar include a phenyl group, a naphtyl group, an indene group, and an azulene group. Examples of an aromatic heterocycle making up the 5 to 10-membered aromatic heterocyclic group include thiophene, pyridine, thiazole, furan, pyrrole, oxazole, isoxazole, isothiazole, triazole, furazan, imidazole, pyrazole, pyrazine, pyrimidine, triazine, quinoline, quinoxaline, benzothiophene, benzimidazole, benzothiazole, benzofuran, coumarin, and isoquinoline.

As to Ar, examples of a substituent that can be included in one of the aromatic hydrocarbon group and the aromatic heterocyclic group include a halogen atom, a phenyl group, a $C_1$-$C_4$ alkyl group, a $C_1$-$C_4$ haloalkyl group, a $C_1$-$C_4$ alkoxy group, and a $C_1$-$C_4$ haloalkoxy group. Examples of the halogen atom include a fluorine atom, a chlorine atom, and a bromine atom. Examples of the $C_1$-$C_4$ alkyl group include a methyl group, an ethyl group, an n-propyl group, an isopropyl group, and an n-butyl group.

Examples of the $C_1$-$C_4$ haloalkyl group include a trifluoromethyl group, a 1,1,2,2,2-pentafluoroethyl group, a chloromethyl group, a trichloromethyl group, and a bromomethyl group. Examples of the $C_1$-$C_4$ alkoxy group include a methoxy group, an ethoxy group, and an n-propoxy group. Examples of the $C_1$-$C_4$ haloalkoxy group include a trifluoromethoxy group, a difluoromethoxy group, a 1,1,2,2,2-pentafluoroethoxy group, and a 2,2,2-trifluoroethoxy group. Further, in the phenyl group serving as the substituent, a hydrogen atom may be substituted with a halogen atom.

As to Ar, the number and position of substituents in the aromatic hydrocarbon group or the aromatic heterocyclic group are not particularly limited. Further, in a case where there are a plurality of substituents in the aromatic hydrocarbon group or the aromatic heterocyclic group, the substituents may be identical to each other or may be mutually different from each other.

The cyanide salt to be reacted with the compound represented by Formula (I) shown above includes an alkali metal cyanide such as sodium cyanide and potassium cyanide, an alkaline earth metal cyanide such as calcium cyanide, metal cyanide such as copper cyanide, silver cyanide, and zinc cyanide, and an organic cyanide such as tetrabutylammonium cyanide. Among these, alkali metal cyanide is preferably employed. Especially preferable is sodium cyanide.

The solvent employed is not particularly limited as long as it does not affect any reaction, and examples of the solvent usually include: aromatic hydrocarbons such as benzene, toluene, xylene, and the like; ethers such as diethyl ether, tetrahydrofuran, dioxane, dimethoxymethane, and the like; amides such as N,N-dimethylformamide, N,N-dimethylacetamide, N-methyl-2-pyrrolidone, and the like; alcohols such as methanol, ethanol, isopropanol, and the like; dimethyl sulfoxide; and water. These solvents may be used in combination of at least two thereof.

To the solvent described above, a catalyst may be added. The catalyst employed is not limited particularly. Examples of the catalyst include: a carbonate of an alkali metal such as sodium carbonate, sodium hydrogen carbonate, potassium carbonate, potassium hydrogen carbonate and the like; a carbonate of an alkaline earth metal such as calcium carbonate, barium carbonate and the like; a hydroxide of an alkali metal such as sodium hydroxide, potassium hydroxide and the like; a halide of an alkali metal such as sodium iodide and the like; an alkoxide of an alkali metal such as sodium methoxide, sodium ethoxide, potassium t-butoxide and the like; an alkali metal hydride such as sodium hydride, potassium hydride, lithium hydride and the like; an organic metal compound of an alkali metal such as n-butyl lithium and the like; an alkali metal amide such as lithium diisopropyl amide and the like; an organic amine such as triethylamine, pyridine, 4-dimethylaminopyridine, N,N-dimethylaniline, 1,8-diazabicyclo-7-[5,4,0]undecene and the like; and a phase transfer catalyst such as tetramethylammonium chloride, benzyltriethylammonium chloride, crown ether and the like. Among these, a halide of an alkali metal, an organic amine, or a phase transfer catalyst is preferably added to the solvent. Sodium iodide, triethylamine, 1,8-diazabicyclo-7-[5,4,0]undecene, or benzyltriethylammonium chloride is more preferably added to the solvent.

The amount of cyanide salt employed per mole of the compound represented by Formula (I) is preferably 0.8 to 20 moles, and more preferably 1 to 5 moles.

The reaction temperature and reaction time can be appropriately selected depending upon the types of solvent, starting material, and cyanide salt as employed, and other conditions. For example, the reaction temperature is in the range from −20° C. to 150° C., and preferably 0° C. to 100° C. The reaction time is, for example, 0.5 hour to 20 days, and preferably 1 hour to 5 days.

In a case where, in an oxetane derivative which is obtained from the compound represented by Formula (II) shown above, which compound is obtained by the production method described above, an oxetane ring is opened with use of, for example, a hydrogen halide, it is possible to obtain only geometrical isomers wherein a hydroxy group and a halogenated methyl group, both of which are formed by the ring opening, are in cis configuration.

A specific example of the method for producing an oxetane compound is, for example, a method for producing an oxetane compound represented by Formula (5) shown below, the method including: the step of reacting, with a cyanide salt, a compound represented by Formula (4):

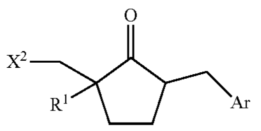

(4)

wherein $R^1$ represents a linear or branched $C_1$-$C_6$ alkyl group; a hydrogen atom(s) contained in the alkyl group may be substituted with a $C_1$-$C_4$ alkoxy group; $X^2$ is selected from a halogen atom and —$OSO_2R^3$ where $R^3$ is selected from a $C_1$-$C_3$ alkyl group, a phenyl group, and a naphthyl group, and a hydrogen atom(s) contained in any one of the alkyl group, the phenyl group, and the naphthyl group may be substituted; and Ar is selected from a $C_6$-$C_{10}$ aromatic hydrocarbon group having a hydrogen atom(s) which may be substituted and a 5 to 10-membered aromatic heterocyclic group having a hydrogen atom(s) which may be substituted, to obtain an oxetane compound represented by Formula (5):

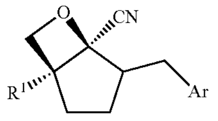

(5)

wherein $R^1$ and Ar are identical to $R^1$ and Ar in Formula (4) shown above, respectively. However, the present invention is not limited to this method. Details of such a specific example will be described later.

[Method 2 for Producing Oxetane Compound]

A second embodiment of a method for producing an oxetane compound, in accordance with the present invention, is a method for producing an oxetane compound represented by Formula (V) shown below, the method including the steps of: reacting, with a cyanide salt, a compound represented by Formula (III):

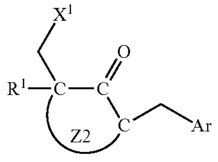

(III)

wherein $R^1$ is selected from a hydrogen atom and a linear or branched $C_1$-$C_6$ alkyl group; a hydrogen atom(s) contained in the alkyl group may be substituted with a $C_1$-$C_4$ alkoxy group; $X^1$ is selected from a halogen atom and —$OSO_2R^3$ where $R^3$ is selected from a $C_1$-$C_3$ alkyl group, a phenyl group, and a naphthyl group, and a hydrogen atom(s) contained in any one of the alkyl group, the phenyl group, and the naphthyl group may be substituted; Ar is selected from a $C_6$-$C_{10}$ aromatic hydrocarbon group having a hydrogen atom(s) which may be substituted and a 5 to 10-membered aromatic heterocyclic group having a hydrogen atom(s) which may be substituted; and a ring Z2 represents a $C_5$-$C_8$ cyclic hydrocarbon having a ring structure which includes (i) a carbon atom bonded to $R^1$, (ii) a carbonyl carbon atom, and (iii) a carbon atom bonded to —$CH_2$—Ar, where a hydrogen atom(s) contained in the cyclic hydrocarbon may be substituted, to obtain an oxetane compound represented by Formula (IV):

(IV)

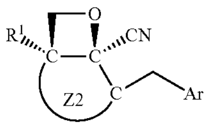

wherein $R^1$, a ring Z2, and Ar are identical to $R^1$, the ring Z2, and Ar in Formula (III) shown above, respectively; and reacting the oxetane compound represented by Formula (IV) shown above with an alkoxide, to obtain the oxetane compound represented by Formula (V):

(V)

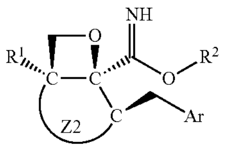

wherein $R^1$, a ring Z2, and Ar are identical to $R^1$, the ring Z2, and Ar in Formula (III) shown above, respectively, and $R^2$ represents a linear or branched $C_1$-$C_6$ alkyl group.

Note that the definitions of $R^1$ and $X^1$ in Formula (iii) are identical to those of $R^1$ and $X^1$ in Formula (I) shown above, respectively.

Ar is selected from: a $C_6$-$C_{10}$ aromatic hydrocarbon group having a hydrogen atom(s) which may be substituted; and a 5 to 10-membered aromatic heterocyclic group having a hydrogen atom(s) which may be substituted. As to Ar, the aromatic hydrocarbon group and the aromatic heterocyclic group and any substituents that can be contained in these groups are as defined above.

As to Ar, the number and position of substituents in the aromatic hydrocarbon group or the aromatic heterocyclic group are not particularly limited. Further, in a case where there are a plurality of substituents in the aromatic hydrocarbon group or the aromatic heterocyclic group, the substituents may be identical to each other or may be mutually different from each other.

Examples of Ar include, but are not limited to, the following formulae (a) through (d):

(a)

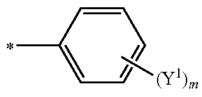

(b)

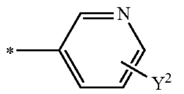

-continued (c)

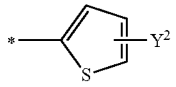

(d)

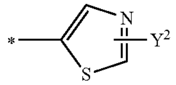

wherein $Y^1$ is selected from a halogen atom, a $C_1$-$C_3$ alkyl group, and a $C_1$-$C_3$ haloalkoxy group, m is selected from 0, 1, and 2, and $Y^2$ represents a halogen atom, and * represents bonding to a methylene group.

Apart from Formulae (a) through (d), examples of Ar include: a polycyclic aromatic hydrocarbon such as naphthalene and azulene; and a polycyclic aromatic heterocycle such as quinoline and benzothiophene.

The ring Z2 represents a $C_5$-$C_8$ cyclic hydrocarbon having a ring structure which includes (i) a carbon atom bonded to $R^1$ and (ii) a carbonyl carbon atom, and (iii) a carbon atom bonded to —$CH_2$—Ar. The ring Z2 is preferably a $C_5$-$C_7$ cyclic hydrocarbon, and especially preferably a $C_5$ cyclic hydrocarbon (cyclopentane). It should be noted that the number of carbon atoms specified here is the number of carbon atoms including the carbon atom bonded to $R^1$, the carbonyl carbon atom, and the carbon atom bonded to —$CH_2$—Ar. Further, a hydrogen atom(s) contained in the cyclic hydrocarbon may be substituted with a substituent. Examples of the substituent in the cyclic hydrocarbon include: an aliphatic hydrocarbon group; an aromatic hydrocarbon group; an aromatic heterocyclic group; an aliphatic hydrocarbon group in which a hydrogen atom is substituted with an aromatic hydrocarbon group or an aromatic heterocyclic group; an alkoxylalkyl group; a carbonyloxyalkyl group; and an amido group. Moreover, hydrogen atoms contained in these substituents may be each substituted with a halogen atom; an alkoxy group; an alkyl group; an aromatic hydrocarbon group; an aromatic heterocyclic group; and the like. Further, in a case where there are a plurality of substituents in the ring Z2, the substituents may form another ring structure, in addition to the ring Z2, together with respective carbon atoms bonded to the substituents.

$R^2$ represents a linear or branched $C_1$-$C_6$ alkyl group. More specifically, examples of $R^2$ include a methyl group, an ethyl group, an n-propyl group, an isopropyl group, an n-butyl group, an isobutyl group, a sec-butyl group, a t-butyl group, an n-pentyl group, a neopentyl group, and an n-hexyl group. $R^2$ is preferably a methyl group and an ethyl group. Among these, a $C_1$-$C_4$ alkyl group is preferable. The type and amount of cyanide salt to be reacted with the compound represented by Formula (III) shown above are identical to those of cyanide to be reacted with the compound represented by Formula (I) shown above.

A solvent that can be used for the reaction of the compound represented by Formula (III) shown above with a cyanide salt and a catalyst that can be added to the solvent are identical to those that can be used for the reaction of the compound represented by Formula (I) shown above with a cyanide salt.

An alkoxide to be reacted with the oxetane compound represented by Formula (IV) shown above is a linear or branched $C_1$-$C_6$ alkoxide. More specifically, such an alkoxide is exemplified by, for example, an alkoxide of an alkali metal such as sodium methoxide, sodium ethoxide, sodium t-butoxide, and potassium t-butoxide.

The amount of alkoxide per mole of the oxetane compound represented by Formula (VI) is, for example, 0.8 to 20 moles, and preferably 1 to 10 moles.

The solvent employed for the reaction with the alkoxide includes alcohols such as methanol, ethanol, isopropanol, butanol, and the like.

The reaction temperature and reaction time can be appropriately selected depending upon the types of solvent, starting material, and alkoxide as employed, and other conditions. For example, the reaction temperature is in the range from −30° C. to 150° C., and preferably −20° C. to 120° C. The reaction time is, for example, 0.5 hour to 10 days, and preferably 1 hour to 7 days.

A specific example of the method for producing an oxetane compound is, for example, a method for producing an oxetane compound represented by Formula (6a) shown below, the method including the steps of: reacting the compound represented by Formula (4) shown above with a cyanide salt to obtain the oxetane compound represented by Formula (5) shown above; and reacting the oxetane compound represented by Formula (5) shown above with an alkoxide to obtain the oxetane compound represented by Formula (6a):

(6a)

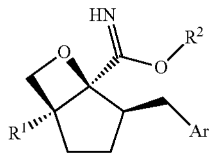

wherein $R^1$ and Ar are identical to $R^1$ and Ar in Formula (4) shown above, respectively, and $R^2$ represents a linear or branched $C_1$-$C_6$ alkyl group. However, the present invention is not limited to this method. Details of such a specific example will be described later.

[Method for Producing Azolylmethylcyclopentanol Compound]

Referring to a preferred example for carrying out the present invention, the following will describe respective embodiments of a method for producing an oxetane compound, a method for producing an azolylmethylcyclopentanol compound, and an intermediate compound in accordance with the present invention. Specifically, the following exemplify methods for producing azolylmethylcyclopentanol compounds each having a 1-position hydroxy group and a 2-position halogenated methyl group in cis configuration (1,2-cis form) and represented by Formula (11):

(11)

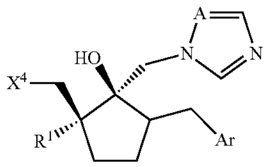

wherein $R^1$ represents a linear or branched $C_1$-$C_6$ alkyl group, a hydrogen atom(s) contained in the alkyl group may be substituted with a $C_1$-$C_4$ alkoxy group, Ar is selected from: a $C_1$-$C_6$ aromatic hydrocarbon group having a hydrogen atom(s) which may be substituted; and a 5 to 10-membered aromatic heterocyclic group having a hydrogen atom(s) which may be substituted, A is selected from a nitrogen atom and a methine group, and $X^4$ represents a halogen atom.

<First Production Method>

According to a first method for producing an azolylmethylcyclopentanol compound, it is possible to selectively produce, out of the azolylmethylcyclopentanol compounds represented by Formula (11) shown above, a cyclopentanol compound having a 1-position hydroxy group and a 5-position —$CH_2$—Ar group in cis configuration (1,5-cis form) and represented by Formula (11a):

(11a)

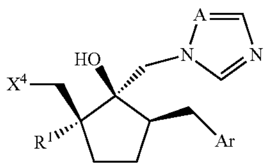

wherein $R^1$, $X^4$, Ar, and A are as defined above in Formula (11) shown above.

A production scheme of the first production method is schematically shown below.

(Production Scheme 1)

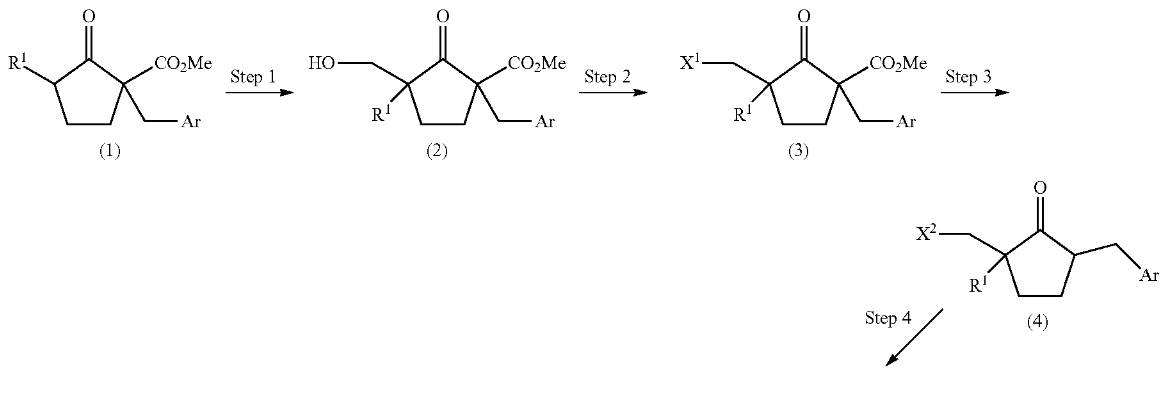

(1) (2) (3) (4)

-continued

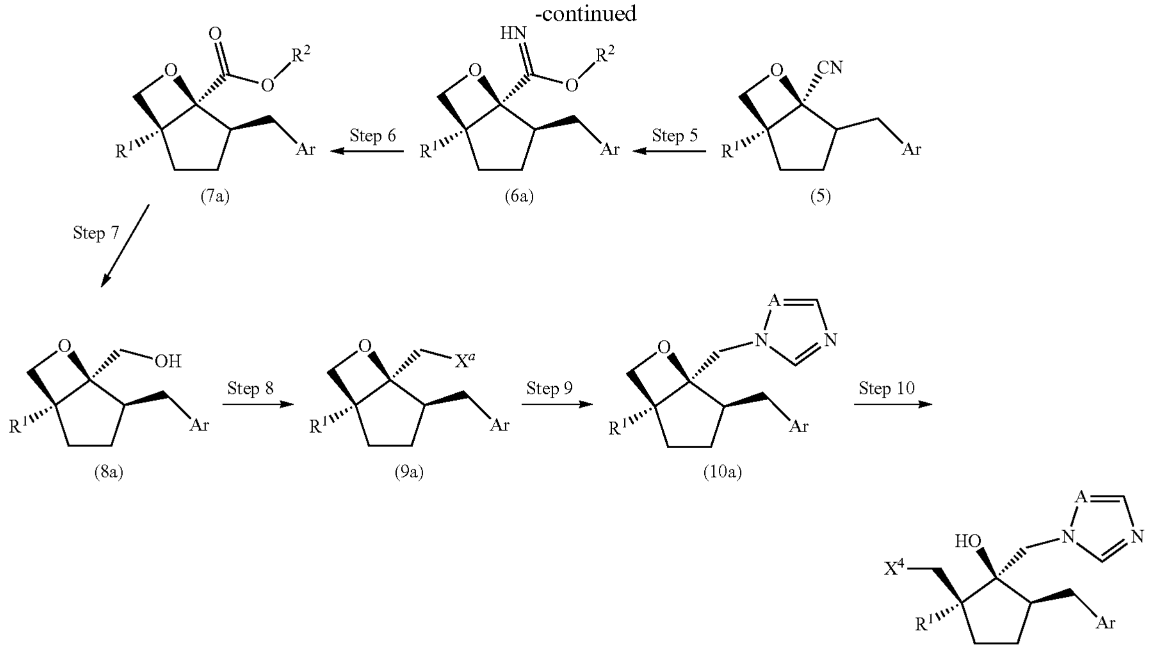

(7a) (6a) (5)

(8a) (9a) (10a)

(11a)

The following will describe steps of the first production method.

(Step 1: Hydroxymethylation)

In the first method for producing an azolylmethylcyclopentanol compound, a compound represented by Formula (1) (hereinafter referred to as "Compound (1)") is hydroxymethylated to obtain a compound represented by Formula (2) (hereinafter referred to as "Compound (2)") (See Reaction Formula (1) shown below).

(Reaction Formula 1)

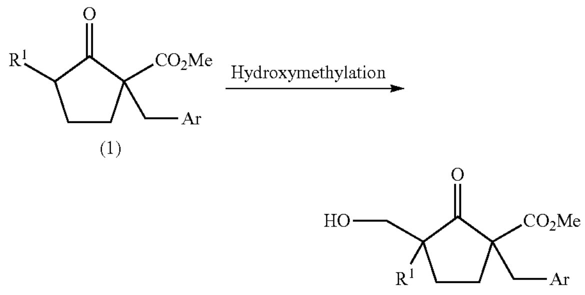

(1)

(2)

Here, $R^1$ in Compound (1) and $R^1$ in Compound (2) are identical, and they are as defined above. Similarly, Ar in Compound (1) and Ar in Compound (2) are identical, and they are as defined above. Examples of Ar include groups represented by the following Formulae (a) through (d):

(a)

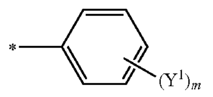

-continued (b)

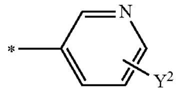

(c)

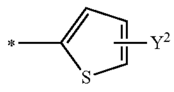

(d)

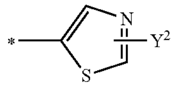

wherein $Y^1$ is selected from a halogen atom, a $C_1$-$C_3$ alkyl group, and a $C_1$-$C_3$ haloalkoxy group, m is selected from 0, 1, and 2, $Y^2$ represents a halogen atom, and * represents bonding to a methylene group.

Specific examples of Ar include, but are not limited to, aromatic hydrocarbon groups and aromatic heterocyclic groups represented by the following Formulae (e) through (1):

(e)

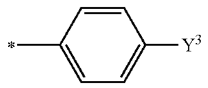

(f)

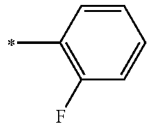

-continued (g)

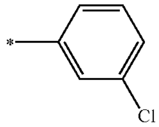

(h)

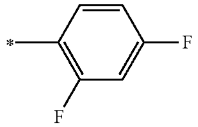

(i)

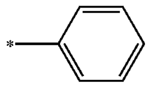

(j)

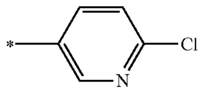

(k)

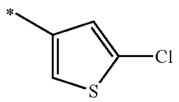

(l)

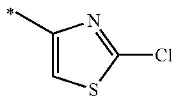

wherein * represents bonding to a methylene group, and in Formula (e), $Y^3$ is selected from a chlorine atom, a fluorine atom, a methyl group, a phenyl group, and a trifluoromethoxy group.

Further, $R^1$ in Compound (2) is as defined above, and preferably a methyl group, an ethyl group, a methoxymethyl group, or an ethoxymethyl group.

A specific method for obtaining Compound (2) is exemplified by a method of reacting Compound (1) with formaldehyde or a formaldehyde derivative (hereinafter referred collectively to as "formaldehyde or the like") in the presence of a base in a solvent.

Here, examples of the formaldehyde derivative include paraformaldehyde, 1,3,5-trioxane, formaldehyde dialkylacetal, and the like.

The amount of formaldehyde or the like per mole of Compound (1) is, for example, 0.5 to 20 moles, and preferably 0.8 to 10 moles.

Examples of the base include, but are not limited to, alkali metal carbonates such as sodium carbonate, potassium carbonate, and the like, alkali metal hydroxides such as sodium hydroxide, potassium hydroxide, and the like, and hydrogen carbonates such as sodium hydrogen carbonate and the like.

The amount of base employed per mole of Compound (1) is, for example, 0.1 to 10 moles, and preferably 0.2 to 5 moles.

Examples of a solvent employed include, but are not particularly limited, ethers such as diethyl ether, tetrahydrofuran, dioxane, and the like; aromatic hydrocarbons such as benzene, toluene, xylene, and the like; and water. These solvents may be used in the form of a mixture of any two or more, if necessary. It should be noted that in a case where the reaction system forms two phases, a phase transfer catalyst, e.g. a customary quaternary ammonium salt (for example, benzyltriethylammonium chloride), is preferably employed.

The reaction temperature is, for example, in the range from 0° C. to 250° C., preferably 0° C. to 100° C., and especially preferably room temperature to 40° C. The reaction time is, for example, 0.1 hour to several days, preferably 0.5 hour to 2 days, and especially preferably 1 hour to 24 hours.

After the reaction, some of excess reaction products may be treated with an aqueous solution of hydrochloric acid, to return them to the intended products (Compound (2)).

Compound (1) used herein can be produced by using a known method (for example, the method described in Patent Literature, Japanese Patent Application Publication Tokukaihei No. 01-93574).

(Step 2: Replacement with Leaving Group)

Next, a predetermined hydroxy group in Compound (2) is replaced with a leaving group, so that the compound represented by Formula (3) (hereinafter referred to as "Compound (3)) is obtained (see Reaction Formula (2) shown below).

(Reaction Formula 2)

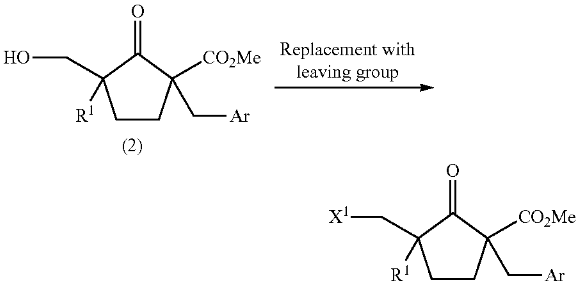

(2)

(3)

$R^1$ and Ar in Compound (3) are identical to $R^1$ and Ar in Compound (2), respectively.

$X^1$ in Compound (3) is as defined above, and preferably a chlorine atom, a methanesulfonyloxy group, or a p-toluenesulfonyloxy group.

A method for replacing a hydroxy group with a leaving group ($X^1$) can be (i) a method of reacting Compound (2) with a sulfonyl chloride, in a solvent, in the presence of an excessive amount of base and (ii) a method of reacting Compound (2) with a thionyl halide.

Examples of the sulfonyl chloride include methanesulfonyl chloride, propanesulfonyl chloride, trifluoromethanesulfonyl chloride, benzenesulfonyl chloride, chlorobenzenesulfonyl chloride, p-toluenesulfonyl chloride, naphthalenesulfonyl chloride, o-nitrobenzenesulfonyl chloride, dimethylaminonaphthylsulfonyl chloride, and the like. Among these sulfonyl chlorides, p-toluenesulfonyl chloride and methanesulfonyl chloride are preferably employed.

The base is not particularly limited. Examples of the base include: aliphatic amines such as triethylamine, diisopropylethylamine, and the like; inorganic bases such as sodium hydride and the like; and aromatic organic bases such as pyridine and the like. Among these, trimethylamine is preferably employed.

In case where p-toluenesulfonyl chloride is employed as the sulfonyl chloride, it is preferable that the reaction of Compound (2) with p-toluenesulfonyl chloride be carried out in the presence of a catalyst such as N-methylimidazole and dimethylaminopyridine.

The amount of sulfonyl chloride employed per mole of Compound (2) is, for example, 0.8 to 10 moles, and preferably 0.9 to 5 moles. The amount of base employed per mole of Compound (2) is, for example, 0.9 to 20 moles, and preferably 1 to 10 moles.

The solvent is not particularly limited. Examples of the solvent include: aromatic hydrocarbons such as benzene, toluene, xylene, and the like; halogenated hydrocarbons such as methylene chloride, chloroform, and the like; and ethers such as tetrahydrofuran, diethyl ether, and the like. Among these, toluene is preferably employed.

As the thionyl halide, thionyl bromide and thionyl chloride, and the like can be employed. Among these, thionyl chloride is preferably employed.

No catalyst and no further solvent are needed in the case where the substitution of the hydroxy group in Compound (2) with a halogen atom is made by the reaction of Compound (2) with the thionyl halide.

The reaction temperature and reaction time can be appropriately selected depending upon the types of solvent as employed, sulfonyl chloride or thionyl halide as employed for the reaction, base as employed, etc. In a case where the reaction is to be carried out with use of a sulfonyl chloride, the reaction temperature is, for example, in the range from −20° C. to 150° C., and preferably −10° C. to 40° C. On the other hand, in a case where the reaction is to be carried out with use of a thionyl halide, the reaction temperature is, for example, −20° C. to 150° C., and preferably 80° C. to 100° C.

In a case where the reaction is to be carried out with use of a sulfonyl chloride, the reaction time is, for example, 0.1 hour to 24 hours, and preferably 0.5 hour to 5 hours. On the other hand, in a case where the reaction is to be carried out with use of a thionyl halide, the reaction time is, for example, 0.5 hour to 24 hours, and preferably 2.5 hour to 3 hours.

(Step 3: Hydrolysis and Decarbonation)

Next, a methoxycarbonyl group of Compound (3) is substituted with hydrogen so that a compound represented by Formula (4) (hereinafter referred to as "Compound (4)") is obtained (see Reaction Formula (3) shown below).

(Reaction Formula 3)

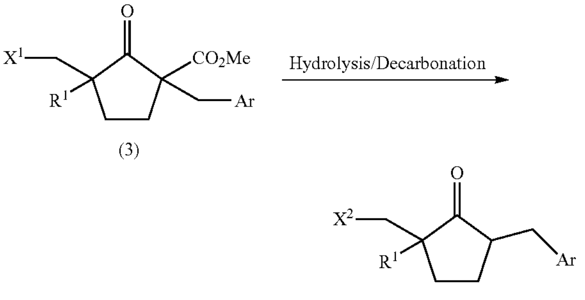

$R^1$ and Ar in Compound (4) are identical to $R^1$ and Ar in Compound (3), respectively.

$X^2$ in Compound (4) is as defined above, but $X^2$ in Compound (4) can be different from $X^1$ in Compound (3). $X^2$ is preferably a chlorine atom, a bromine atom, a methanesulfonyloxy group, or a p-toluenesulfonyloxy group.

A method for substituting the methoxycarbonyl group with hydrogen can be a method of subjecting the methoxycarbonyl group in Compound (3) to hydrolysis and decarbonation with use of an acid catalyst.

Examples of the acid catalyst include: hydrogen bromide; hydrogen chloride; a substituted sulfonic acid such as methanesulfonic acid and p-toluenesulfonic acid; and sulfuric acid. In a case where hydrogen bromide is employed as the acid catalyst, $X^1$ in Compound (3) is often substituted with bromine.

As the solvent, water and acetic acid are preferably employed.

The reaction temperature and reaction time can be appropriately selected depending upon the types of solvent and acid catalyst as employed and other conditions. For example, the reaction temperature (reflux temperature) is in the range from 0° C. to 150° C., and preferably 80° C. to 130° C. The reaction time is, for example, 0.5 hour to 48 hours, and preferably 1 hour to 24 hours.

(Step 4: Oxetane Ring Closure)

Next, conversion into oxetane is carried out by reaction of Compound (4) with a cyanide salt, so that an oxetane compound represented by Formula (5) (hereinafter referred to as "Compound (5)") is obtained (see Reaction Formula (4) shown below).

(Reaction Formula (4))

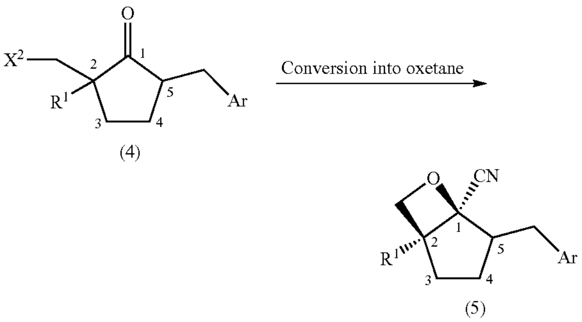

$R^1$ and Ar in Compound (5) are identical to $R^1$ and Ar in Compound (4), respectively.

Examples of the cyanide salt include: an alkali metal cyanide such as sodium cyanide, potassium cyanide and the like; calcium cyanide; and tetrabutylammonium cyanide. Among these, sodium cyanide is preferably employed.

The amount of cyanide salt employed per mole of Compound (4) is, for example, 0.8 to 20 moles, and preferably 0.2 to 5 moles.

Examples of the solvent employed include: aromatic hydrocarbons such as benzene, toluene, xylene, and the like; ethers such as dimethoxyethane, tetrahydrofuran, and the like; amides such as N-methyl-2-pyrrolidone, dimethylformamide, and the like; alcohols such as methanol, ethanol, isopropanol, and the like; dimethyl sulfoxide; water; and a mixture of at least two of these solvents. Further, in a case where the solvent is a binary phase solvent composed of water and an organic solvent, a phase transfer catalyst can be used. A preferably employed phase transfer catalyst is benzyltributylammonium chloride, tetrabutylammonium bromide, or trioctylmethylammonium chloride.

The reaction temperature and reaction time can be appropriately selected depending upon the types of solvent(s) and cyanide salt as employed and other conditions. For example, the reaction temperature is in the range from −10° C. to 150° C., and preferably room temperature to 70° C. The reaction time is, for example, 0.5 hour to 30 days and preferably from 1 hour to 11 days. In a case where $X^2$ in Compound (4) is bromine atom, the reaction time is relatively as short as, for example, 1 to 24 hours. On the other hand, in a case where $X^2$ in Compound (4) is a chlorine atom, the reaction time needs to be relatively as long as, for example, 48 hours to 14 days. In a case where $X^2$ in Compound (4) is a substituted sulfonyloxy group such as a toluenesulfonyloxy group and a methanesulfonyloxy group, the reaction time is, for example, 1 hour to 7 days.

In the reaction carried out in the present step, a catalyst may be added to the solvent(s). Examples of the catalyst preferably employed include sodium iodide, sodium bromide, triethylamine, benzyltriethylammonium chloride, and 1,8-diazabicyclo-7-[5,4,0]undecene.

As to adjacent groups of a cyclopentane ring, they are able to form an oxetane compound only when they are 1,2-cis forms under constraints on their steric configurations. However, when subjected to cyanide-ion addition, which is an equilibrium reaction, an isomer (1,2-trans form) causing no oxetane ring opening returns to Compound (4) as an original material. In this case, the cyanide-ion addition reaction is carried out again. In order to maintain equilibrium until cyanide ions are added to the isomers (1,2-cis form) that cause oxetane ring opening reaction, resultant products are converged to oxetane compounds wherein oxetane ring closure reactions have occurred.

Further, since an organic group adjacent to the oxetane ring generated in a cyclopentane ring (i.e. an organic group corresponding to the 5-position organic group in Compound (4). For convenience of explanation, the position number of this organic group herein is regarded as "5-position" even after the condensed ring is formed, and the same applies to other intermediate compounds each having a condensed ring formed from a cyclopentane ring and oxetane.) is relatively bulky, steric configuration of such an organic group preferentially becomes cis (hereinafter referred to as 1,5-cis form) due to its steric hindrance (For example, 1,5-cis forms and 1,5-trans forms are obtained in the ratio of approximately 9:1 in a case where they are obtained by room temperature reaction in a N-methyl-2-pyrrolidone solvent.).

(Step 5: Imidization)

Next, Compound (5) is reacted with an alkoxide, so that an imidate compound represented by Formula (6a) (hereinafter referred to as "Compound (6a)") is obtained (see Reaction Formula (5) shown below).

(Reaction Formula (5))

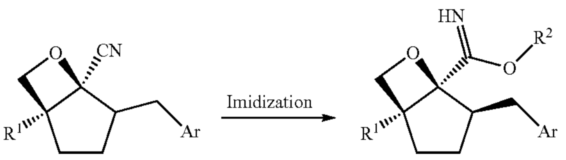

(5) (6a)

$R^1$ and Ar in Compound (6a) are identical to $R^1$ and Ar in Compound (5), respectively.

$R^2$ in Compound (6a) is as defined above, and a methyl group and an ethyl group are preferably employed as $R^2$.

The alkoxide to be reacted with Compound (5) is a linear or branched $C_1$-$C_6$ alkoxide. Examples of the alkoxide include an alkoxide of an alkali metal such as sodium methoxide, sodium ethoxide, sodium t-butoxide, potassium t-butoxide, and the like. Among these, sodium methoxide, sodium ethoxide, and potassium t-butoxide are preferably employed.

The amount of alkoxide employed per mole of Compound (5) is, for example, 0.8 to 100 moles, and preferably 1 to 50 moles.

A solvent employed for the reaction with the alkoxide includes alcohols such as methanol, ethanol, isopropanol, butanol, and the like. In particular, an alcohol having the same hydrocarbon structure as that of the alkoxide is preferably employed. For example, in a case where sodium methoxide is employed as the alkoxide, methanol is preferably employed as the solvent. Meanwhile, in a case where sodium ethoxide is employed as the alkoxide, ethanol is preferably employed as the solvent.

The reaction temperature and reaction time can be appropriately selected depending upon the types of solvent and alkoxide as employed and other conditions. For example, the reaction temperature is in the range from −30° C. to 150° C., and preferably room temperature to 70° C. The reaction time is, for example, 0.5 hour to 10 days, and preferably 15 hours to 90 hours.

In the present step, the alkoxide addition reaction with respect to the cyano group proceeds only for a 1,5-cis form of Compound (5). Accordingly, a resultant products obtained at this point of time is one type of geometric isomer (with a 1,2-cis form and a 1,5-cis form).

(Step 6: Esterification)

Next, Compound (6a) is reacted with an acid catalyst, so that an ester compound represented by Formula (7a) (hereinafter referred to as "Compound (7a)") is obtained (see Reaction Formula (6) shown below).

(Reaction Formula (6))

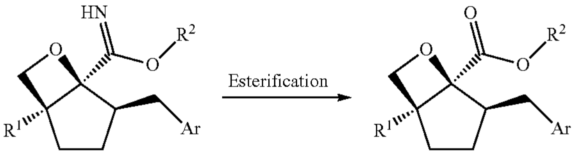

(6a) (7a)

$R^1$, $R^2$, and Ar in Compound (7a) are identical to $R^1$, $R^2$, and Ar in Compound (6a), respectively.

The reaction for esterification of Compound (6a) includes the following reaction: Compound (6a) is reacted with an acid catalyst to add an acid to Compound (6a), and the reaction for ammonium removal is then carried out.

The acid catalyst is not particularly limited. Examples of the acid catalyst employed include: halogen acid such as hydrogen chloride, hydrogen bromide, hydrogen iodide, and the like; sulfuric acid; and an organic acid such as formic acid, acetic acid, butyric acid, trifluoroacetic acid, p-toluenesulfonic acid, and the like. Among these, sulfuric acid, toluenesulfonic acid, methanesulfonic acid, trifluoroacetic acid, citric acid, and acetic acid are preferably employed.

The amount of acid catalyst employed per mole of Compound (6a) is, for example, 0.1 to 10 moles, and preferably 0.5 to 5 moles.

Examples of the solvent include: ethers such as dimethyl ether, tetrahydrofuran, diethyl ether, cyclopentylmethyl ether, and the like; alcohols such as methanol, ethanol, isopropanol, and the like; and aromatic hydrocarbons such as benzene, toluene, xylene, and the like. Among these, dimethyl ether, tetrahydrofuran, diethyl ether, cyclopentylmethyl ether, toluene, and methanol are preferably employed.

The reaction temperature and reaction time can be appropriately selected depending upon the types of solvent and acid catalyst as employed and other conditions. For example, the reaction temperature is in the range from −20° C. to 150° C., and preferably room temperature to 80° C. The reaction time is, for example, 0.5 hour to 10 days, and preferably 1 hour to 90 hours.

(Step 7: Reduction Reaction)

Next, Compound (7a) is reduced so that a compound represented by Formula (8a) (hereinafter referred to as "Compound (8a)") is obtained (see Reaction Formula (7) shown below).

(Reaction Formula (7))

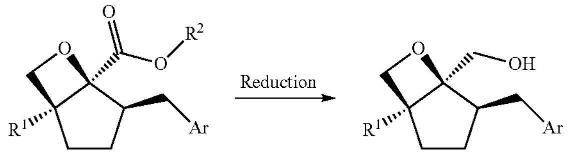

(7a) (8a)

$R^1$ and Ar in Compound (8a) are identical to $R^1$ and Ar in Compound (7a), respectively.

A reducing agent for reducing Compound (7a) includes a hydride type reducing agent. For example, the hydride type reducing agent includes sodium borohydride, calcium borohydride, lithium borohydride, lithium aluminum hydride, and the like. Among these, sodium borohydride and calcium borohydride are preferably employed. Further, the reducing agent can be prepared in a reaction system if necessary.

The amount of reducing agent employed per mole of Compound (7a) is, for example, 0.2 to 50 moles, and preferably 0.5 to 20 moles.

The solvent include: alcohols such as methanol, ethanol, isopropanol, and the like; and ethers such as diethyl ether, tetrahydrofuran, dioxane, and the like. Among these, methanol, ethanol, and tetrahydrofuran are preferably employed.

The reaction temperature and reaction time can be appropriately selected depending upon the types of solvent as employed and reducing agent as employed, the presence or absence of an additive(s), and other conditions. For example, in a case where calcium borohydride is employed as the reducing agent, the reaction temperature (reflux temperature) is, for example, in the range from −30° C. to 70° C., and preferably −20° C. to 50° C. In this case, the reaction time is, for example, 0.5 hour to 24 hours, and preferably 1 hour to 8 hours.

(Step 8: Substitution with Leaving Group)

Next, a hydroxy group of Compound (8a) is substituted with a leaving group, so that a compound represented by Formula (9a) (hereinafter referred to as "Compound (9a)") is obtained (see Reaction Formula (8) shown below).

(Reaction Formula (8))

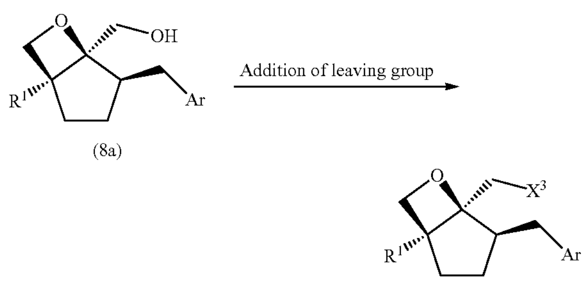

(8a)

(9a)

$R^1$ and Ar in Compound (9a) are identical to $R^1$ and Ar in Compound (8a), respectively.

$X^3$ in Compound (9a) is not particularly limited as long as it is a leaving group. For example, $X^3$ includes: a halogen atom such as a fluorine atom, a chlorine atom, a bromine atom, and the like; and a substituted sulfonyloxy group such as a methanesulfonyloxy group, a propanesulfonyloxy group, a trifluoromethanesulfonyloxy group, a benzenesulfonyloxy group, a chlorobenzenesulfonyloxy group, a p-toluenesulfonyloxy group, a naphthalenesulfonyloxy group, an o-nitrobenzenesulfonyloxy group, a dimethylaminonaphthylsulfonyloxy group, and the like. Among these, a chlorine atom, a p-toluenesulfonyloxy group, and a methanesulfonyloxy group are preferably employed. Especially, a p-toluenesulfonyloxy group and a methanesulfonyloxy group are preferably employed.

A method for substituting a hydroxy group with a leaving group can be (i) a method of reacting Compound (8a) with a sulfonyl chloride, in a solvent, in the presence of an excessive amount of base and (ii) a method of reacting Compound (8a) with a thionyl halide. Among these methods, the method (i) is more preferably selected.

The sulfonyl chloride and thionyl halide that are useful in the present step are the same as those that are useful in the Step 2.

Similarly, the base and solvent that are useful in the present step are the same as those that are useful in the Step 2. No further solvent is needed in a case where the hydroxy group in Compound (8a) is halogenated by the reaction of Compound (8a) with the thionyl halide.

In case where p-toluenesulfonyl chloride is employed as the sulfonyl chloride, it is preferable that the reaction of Compound (8a) with p-toluenesulfonyl chloride be carried out in the presence of a catalyst such as N-methylimidazole and dimethylaminopyridine.

The amount of sulfonyl chloride employed per mole of Compound (8a) is, for example, 0.8 to 10 moles, and preferably 0.9 to 5 moles. The amount of base employed per mole of Compound (8a) is, for example, 0.9 to 12 moles, and preferably 1 to 6 moles.

The reaction temperature and reaction time can be appropriately selected depending upon the types of solvent as employed, sulfonyl chloride as employed for the reaction or thionyl halide as employed for the reaction, base as employed, etc. In a case where the reaction is to be carried out with use of a sulfonyl chloride, the reaction temperature is, for example, in the range from −20° C. to 150° C., and preferably 0° C. to 40° C. In this case, the reaction time is, for example, 0.1 hour to 24 hours, and preferably 0.5 hour to 5 hours.

(Step 9: Addition of Azole)

Next, Compound (9a) is reacted with a triazole compound or an imidazole compound, so that a compound represented by Formula (10a) (hereinafter referred to as "Compound (10a)") is obtained (see Reaction Formula (9) shown below).

(Reaction Formula (9))

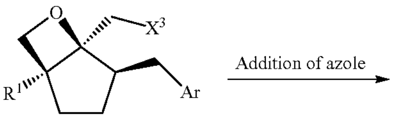

(9a)

-continued

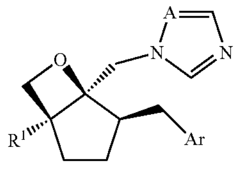

(10a)

$R^1$ and Ar in Compound (10a) are identical to $R^1$ and Ar in Compound (9a), respectively.

A in Compound (10a) represents a nitrogen atom or a methine group.

A method for obtaining Compound (10a) can be a method of reacting Compound (9a) with an imidazole compound or a triazole compound, in a solvent, in the presence of a base.

The imidazole compound and the triazole compound can be, respectively, a metal salt of imidazole and a metal salt of 1,2,4-triazole represented by Formula (VI):

(VI)

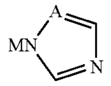

wherein A represents a nitrogen atom or a methine group, and M represents a metal. Preferably employed as M are alkali metals. Among the alkali metals, sodium and potassium are especially preferable.

The base is not particularly limited. The base includes: alkali metal hydroxides such as sodium hydroxide, potassium hydroxide, and the like; a metal hydride compound such as sodium hydride, potassium hydride, and lithium hydride, and the like; and an alkoxide of an alkali metal such as sodium methoxide, sodium ethoxide, sodium t-butoxide, potassium t-butoxide, and the like. Among these, sodium hydroxide, potassium hydroxide, sodium hydride, and potassium t-butoxide are preferably employed, and sodium hydroxide and potassium hydroxide are more preferably employed. Further, the base may be used to be processed with an azole compound in advance so as to form a salt, or may be used by letting the base and the azole compound coexist in a reaction system.

The solvent is not particularly limited. For example, the solvent includes: amides such as N,N-dimethylformamide, N,N-dimethylacetamide, N-methyl-2-pyrrolidone, and the like; and ethers such as 1,4-dioxane, tetrahydrofuran, and the like. Among these, N,N-dimethylformamide and N-methylpyrrolidone are preferably employed.

The amount of imidazole compound or triazole compound employed per mole of Compound (9a) is, for example, 0.8 to 20 moles, and preferably 1 to 5 moles.

The reaction temperature and reaction time can be appropriately selected depending upon the types of solvent and base as employed and other conditions. For example, the reaction temperature is in the range from 0° C. to 150° C., and preferably 100° C. to 130° C. The reaction time is, for example, 0.5 hour to 48 hours, and preferably 2 hour to 12 hours.

(Step 10: Ring Opening of Oxetane)

Next, an oxetane ring possessed by Compound (10a) is subjected to ring opening, so that an azolylmethylcyclopentanol compound represented by Formula (11a) (hereinafter referred to as "Compound (11a)") is obtained (see Reaction Formula (10) shown below).

(Reaction Formula (10))

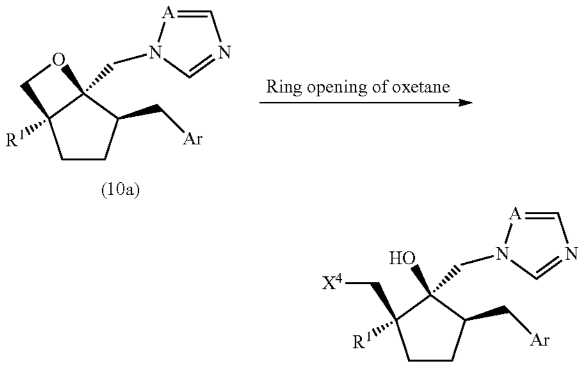

(10a)

(11a)

$R^1$, Ar, and A in Compound (11a) are identical to $R^1$, Ar, and A in Compound (10a), respectively.

$X^4$ in Compound (11a) represents a halogen atom. Specifically, $X^4$ in Compound (11a) is selected from a fluorine atom, a chlorine atom, a bromine atom, and an iodine atom, and preferably a chlorine atom or a bromine atom.

Preferably employed as a method for subjecting an oxetane ring possessed by Compound (10a) to ring opening is a method of mixing Compound (10a) and a halogen acid in a solvent to produce a halogenated methyl group and a tertiary hydroxy group.

The halogen acid includes hydrogen fluoride, hydrogen chloride, hydrogen bromide, and hydrogen iodide. Among these, hydrogen chloride and hydrogen bromide are preferably employed. The halogen acid may be introduced as a gas or may be added in the form of being dissolved in an organic solvent. It should be noted that the halogen acid employed to obtain Compound (11a) from Compound (10a) may be a halogen acid produced by mixing a halide salt (e.g. lithium chloride and sodium chloride) and an acid irrelevant to the halogenic acid salt (e.g. a Bronsted acid such as toluenesulfonic acid, methanesulfonic acid, sulfuric acid, and the like or a Lewis acid such as aluminum chloride and the like) in a reaction system. The solvent is not particularly limited. For example, the solvent includes: amides such as N-methylpyrrolidone, N,N-dimethylformamide, and the like; alcohols such as methanol, ethanol, and the like; ethers such as tetrahydrofuran, dioxane, and the like; and water. Among these, dimethylformamide, methanol, water, and dioxane are preferably employed.

The amount of halogen acid employed per mole of Compound (10a) is, for example, 0.5 to 50 moles, and preferably 1 to 20 moles.

A reaction temperature can be appropriately selected depending upon the type of solvent as employed and other conditions. For example, the reaction temperature is in the range from −20° C. to 250° C., preferably −10° C. to 150° C., and especially preferably 50° C. to 80° C. A reaction time can be appropriately selected depending upon the type of solvent as employed and other conditions. For example, the reaction time is 0.1 hour to several days, and preferably 1 hour to 48 hours.

In a case where a halogen acid is added to the oxetane, Compound (11a) thus obtained has a 1-position tertiary hydroxy group and a 2-position halogenated methyl group.

As described above, according to (a) a method for producing an oxetane compound in the present embodiment and (b) a method for producing an azolylmethylcyclopentanol compound in the present embodiment, it is possible to selectively and suitably produce an azolylmethylcyclopentanol compound which is one type of geometric isomer with a 1,2-cis form and a 1,5-cis form and represented by Formula (11a) shown above.

The intermediates obtained respectively in the Steps 3, 4, and 5, i.e. Compound (4), Compound (5), and Compound (6), are suitably used in (a) the method for producing an oxetane compound in the present embodiment and (b) a method for producing an azolylmethylcyclopentanol compound, wherein the method (b) includes the method (a), in the present embodiment. Thus, these intermediates are also encompassed by the scope of the present invention.

<Second Production Method>

The following will describe another embodiment (second production method) of the method for producing an azolylmethylcyclopentanol compound. A production scheme of the second production method is schematically shown below.

(Reaction Formula (B1))

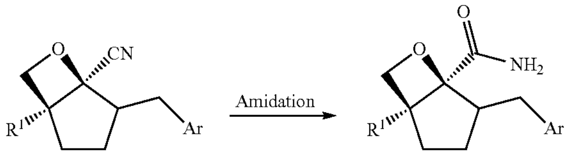

(5) (12)

$R^1$ and Ar in Compound (12) are identical to $R^1$ and Ar in Compound (5), respectively.

A specific method for obtaining Compound (12) can be a method of subjecting the cyano group in Compound (5) to hydrolysis in a solvent in the presence of a base.

The base includes alkali metal hydroxides such as sodium hydroxide, potassium hydroxide, and the like. Preferably employed is sodium hydroxide.

The amount of base employed per mole of Compound (5) is, for example, 0.5 to 20 moles, and preferably 1 to 10 moles.

The solvent include: water; alcohols such as methanol, ethanol, isopropanol, and the like; and ethers such as diethyl ether, tetrahydrofuran, dioxane, and the like. Among these, water, methanol, tetrahydrofuran, and a mixture of at least two thereof are preferably employed.

(Production Scheme 2)

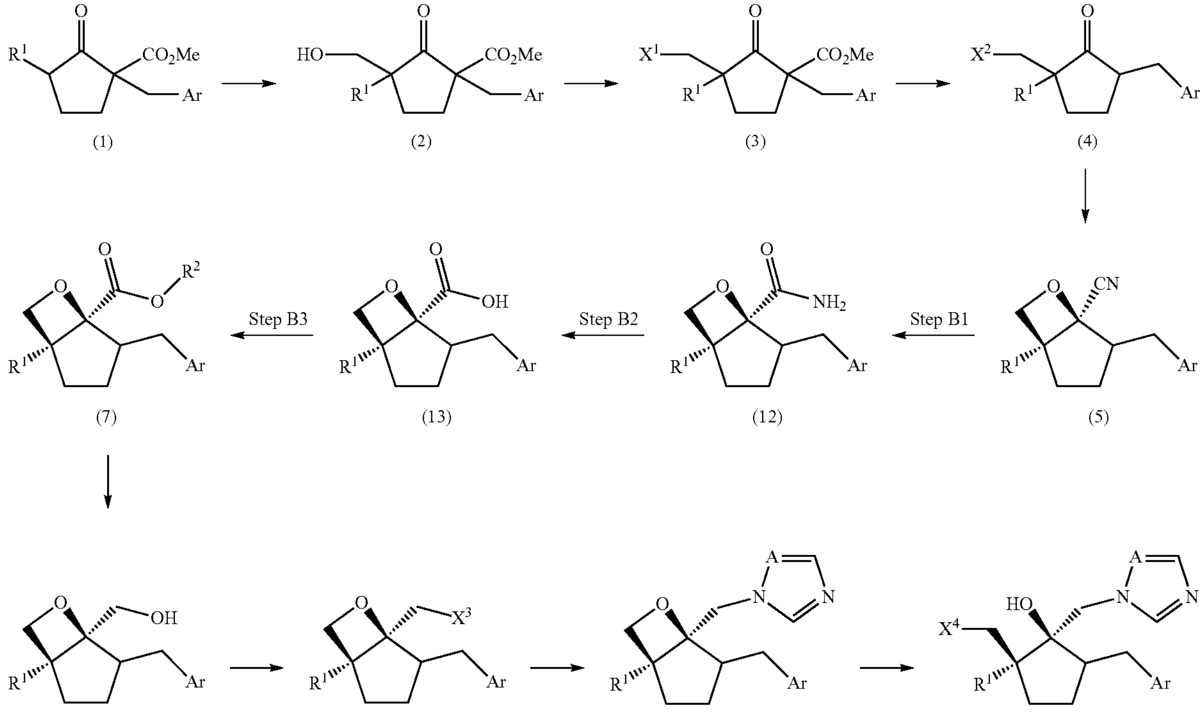

(1) (2) (3) (4)

(7) (13) (12) (5)

(8) (9) (10) (11)

The following will describe steps of the second production method. The steps undergone until Compound (5) is obtained are the same as the Steps 1 through 4 of the first production method, and explanation thereof is therefore omitted.

(Step B1: Amidation)

A cyano group of Compound (5) is subjected to hydrolysis, so that an amide compound represented by Formula (12) (hereinafter referred to as "Compound (12)") is obtained (see Reaction Formula (B1) shown below).

The reaction temperature and reaction time can be appropriately selected depending upon the types of solvent and base as employed and other conditions. For example, the reaction temperature (reflux temperature) is in the range from −20° C. to 150° C., and preferably room temperature to 100° C. The reaction time is, for example, 0.5 hour to 48 hours, and preferably 2 hours to 8 hours.

In a case where the reaction system is a water-containing system, the amidation carried out in the present step proceeds in preference to the imidation carried out in the Step 5. However, unlike the imidation carried out in the Step 5, the amidation carried out in the present step proceeds for a 1,5-trans form (see Reaction Formula (b 1) shown below) as well of Compound (5) represented by Formula (5b).

(Reaction Formula (b1))

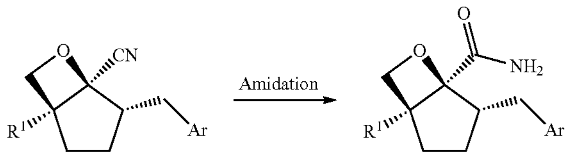

(5b) (12b)

(Step B2: Carboxylation)

Next, Compound (12) is subjected to carboxylation, so that a compound represented by Formula (13) (hereinafter referred to as "Compound (13)") is obtained (see Reaction Formula (B2) shown below).

(Reaction Formula (B2))

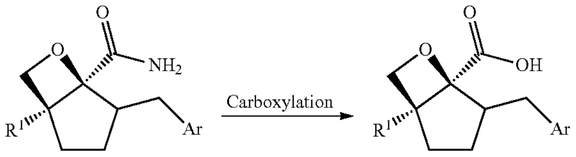

(12) (13)

$R^1$ and Ar in Compound (13) are identical to $R^1$ and Ar in Compound (12), respectively.

A specific method for obtaining Compound (13) can be (i) a method of reacting Compound (12) with a nitrogen oxide so as to nitrosate Compound (12), and then subjecting Compound (12) thus nitrosated to carboxylation with denitrification and (ii) a method of carrying out hydrolysis with use of a high concentration aqueous solution of hydroxide.

(i) Nitrosation

A nitrosation reagent includes nitrite gas and nitrogen oxide such as dinitrogen trioxide. These nitrosation reagents may be introduced in gaseous form or may be generated in the reaction system. In the case where the nitrosation reagent is to be generated in the reaction system, the nitrosation reagent can be obtained by coexistence of a nitrite such as sodium nitrite, potassium nitrite, and the like with an acid such as hydrochloric acid, sulfuric acid, and the like. In the case where the nitrosation reagent is to be introduced in gaseous form, gas generated in the aforementioned manner may be supplied to the reaction system.

The amount of nitrogen oxide employed per mole of Compound (12) is, for example, 0.8 to 100 moles, and preferably 1 to 50 moles.

A solvent employed for the nitrosation includes acetic acid, water, and the like. Preferably employed is acetic acid.

The reaction temperature and reaction time for the nitrosation reaction are as follows. For example, the reaction temperature is in the range from −20° C. to 150° C., and preferably room temperature to 50° C. The reaction time is, for example, 1 hour to 72 hours, and preferably 1 hour to 48 hours. For example, the preferable reaction time is 15 hours.

(ii) Hydrolysis with use of High Concentration Aqueous Solution of Hydroxide

In a case where hydrolysis is to be carried out with use of a high concentration aqueous solution of hydroxide, an aqueous solution of hydroxide includes: an aqueous solution of alkali metal hydroxide, such as an aqueous solution of sodium hydroxide, an aqueous solution of potassium hydroxide, and the like; calcium hydroxide; barium hydroxide; and the like. Among these, an aqueous solution of sodium hydroxide is preferably employed. The aqueous solution of hydroxide needs to be of high concentration. The concentration of the aqueous solution of hydroxide is, for example, 20% to 98%, and preferably 50% to 98%.

The solvent includes alcohols such as ethylene glycol, propylene glycol, diethylene glycol, glycerin, and the like. Among these, ethylene glycol is preferably employed.

The reaction temperature and reaction time for the hydrolysis with use of an aqueous solution of hydroxide can be appropriately selected depending upon the types of solvent as employed and aqueous hydroxide solution as employed, and other conditions. For example, the reaction temperature is in the range from −10° C. to 200° C., and preferably room temperature to 150° C. The reaction time is, for example, 0.5 hour to 48 hours, and preferably 1 hour to 24 hours. For example, the preferable reaction time is 13 hours.

(Step B3: Esterification)

Next, Compound (13) is subjected to esterification, so that a compound represented by Formula (7) (hereinafter referred to as "Compound (7)") is obtained (see Reaction Formula (B3) shown below).

(Reaction Formula (B3))

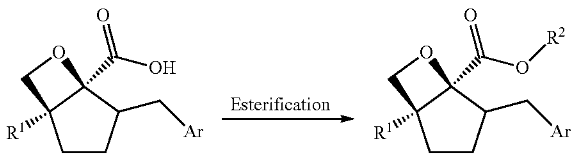

(13) (7)

Compound (7) obtained in the Step B3 is the same as Compound (7a), except that Compound (7) includes not only a 1,5-cis form but also a 1,5-trans form represented by Formula (7b):

(7b)

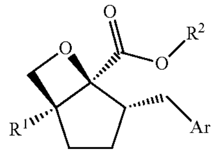

A method for esterifying Compound (13) can be (i) a method of subjecting Compound (13) to alcohol substitution with use of an acid catalyst in an alcohol solvent and (ii) a method of preparing an acid halide of Compound (13) in the presence of a base and then subjecting the acid halide thus prepared to alcohol substitution in an alcohol solvent.

(i) Alcohol Substitution with Use of Acid Catalyst

The acid catalyst includes toluenesulfonic acid, sulfuric acid, and the like. Among these, toluenesulfonic acid is preferably employed.

The alcohol solvent employed for the alcohol substitution with use of the acid catalyst includes alcohols such as methanol, ethanol, isopropanol, butanol, and the like. Among these, methanol and ethanol are preferably employed.

The reaction temperature and reaction time for the alcohol substitution with use of the acid catalyst are as follows. For example, the reaction temperature (reflux temperature) is in the range from −20° C. to 120° C., and preferably −10° C. to 80° C. The reaction time is, for example, 1 hour to 48 hours, and preferably 2 hour to 24 hours. For example, the preferable reaction time is 18 hours.

(ii) Alcohol Substitution Through Preparation of Acid Halide

An acid halogenating agent includes: thionyl halides such as thionyl chloride, thionyl bromide, and the like; oxalyl chloride; and the like. Among these, thionyl chloride is preferably employed.

The amount of acid halogenating agent employed per mole of Compound (13) is, for example, 0.8 to 20 moles, and preferably 0.9 to 10 moles.

The base includes amines such as triethylamine, diisopropylethylamine, and the like. Among these, triethylamine is preferably employed.

A solvent employed for the preparation of an acid halide includes: aromatic hydrocarbons such as benzene, toluene, xylene, and the like; ethers such as tetrahydrofuran and the like; and halogenated hydrocarbons such as chloroform, methylene chloride, and the like. Among these, toluene is preferably employed.

The reaction temperature for the preparation of an acid halide is, for example, in the range from −20° C. to 100° C., and preferably 0° C. to room temperature. The reaction time is, for example, 0.1 hour to 24 hours, and preferably 0.2 hour to 12 hours. For example, the preferable reaction time is 1 hour.

The alcohol solvent employable for the alcohol substitution of the acid halide includes alcohols such as methanol, ethanol, isopropanol, butanol, and the like. Among these, methanol and ethanol are preferably employed.

The base includes amines such as triethylamine, diisopropylethylamine, and the like. Among these, triethylamine is preferably employed.

The reaction temperature for the alcohol substitution is, for example, in the range from −20° C. to 120° C., and preferably 0° C. to room temperature. The reaction time is, for example, 0.1 hour to 24 hours, and preferably 0.2 hour to 12 hours. For example, the preferable reaction time is 0.5 hour.

To the steps undergone until Compound (11) is obtained from Compound (7), the Steps 7 through 10 of the first production method can be applied. As described previously, Compound (7) includes not only a 1,5-cis form but also a 1,5-trans form. Accordingly, Compound (11) finally obtained, which is different from Compound (11) produced by the first production method, includes not only a 1,5-cis form but also a 1,5-trans form represented by Formula (11b):

(11b)

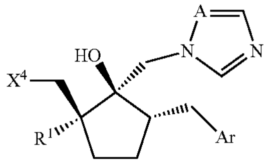

In the Step B3 of the second production method, Compound (7) is obtained by esterifying a carboxy group of Compound (13).

Alternatively, a compound represented by Formula (8) (hereafter referred to as "Compound (8)") may be obtained through a step of preparing an acid halide of Compound (13) (in Reaction Formula (B4), forming an acid chloride of Compound (13)) (Step B4) and a step of reducing the acid halide (Step B5), as shown below in Reaction Formulae (B4) and (B5), respectively.

(Reaction Formula (B4))

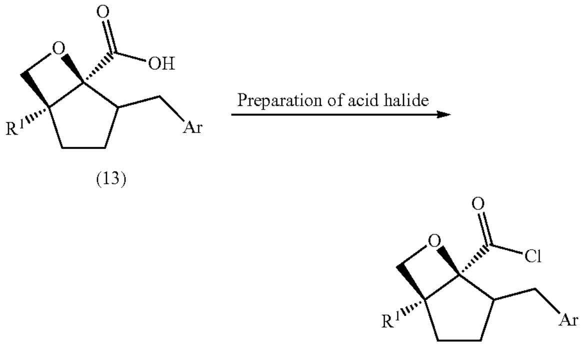

(13)

(14)

(Reaction Formula (B5))

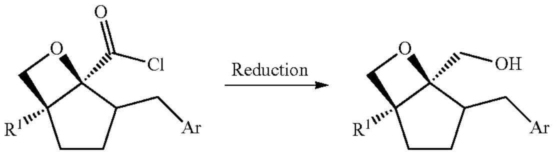

(14) (8)

Compound (8) obtained through the Steps B4 and B5 is the same as Compound (8a), except that Compound (8) includes not only a 1,5-cis form but also a 1,5-trans form.

An acid halogenating agent employed in the Step B4 includes thionyl chloride, oxalyl chloride, and the like.

Further, a reducing agent employed in the Step B5 includes sodium borohydride, lithium aluminum hydride, and the like.

To the steps undergone until Compound (11) is obtained from Compound (8), the Steps 8 through 10 of the first production method can be applied.

As described above, the second production method is a method for producing an azolylmethylcyclopentanol compound, including the step of hydrolyzing the compound represented by Formula (5), which compound is obtained by a method for producing an oxetane compound in accordance with the present invention, to obtain the compound represented by Formula (12).

According to the method for producing an oxetane compound in the present embodiment and the method for producing an azolylmethylcyclopentanol compound in the present embodiment, it is possible to proceed the reactions of not only a 1,5-cis form but also a 1,5-trans form. This makes it possible to increase the yield of an azolylmethylcyclopentanol compound finally obtained.

<Third Production Method>

The following will describe still another embodiment (third production method) of the method for producing an azolylmethylcyclopentanol compound. A production scheme of the third production method is schematically shown below.

-continued

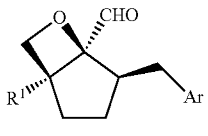

(15)

(Production Scheme 3)

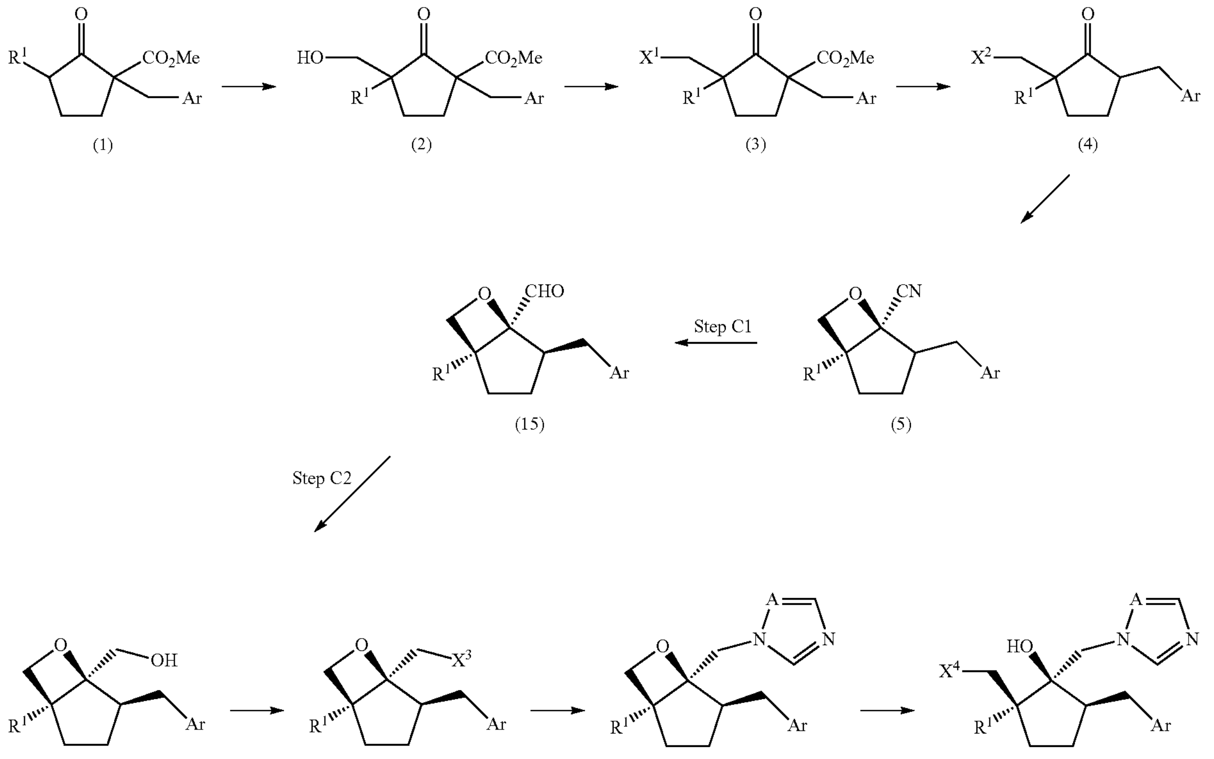

(1) (2) (3) (4)

(15) (5)

(8a) (9a) (10a) (11a)

The following will describe steps of the third production method. The steps undergone until Compound (5) is obtained are the same as the Steps 1 through 4 of the first production method, and explanation thereof is therefore omitted.

(Step C1: Substitution with Aldehyde)

The cyano group in Compound (5) is substituted with an aldehyde, so that a compound represented by Formula (15) (hereinafter referred to as "Compound (15)") is obtained (see Reaction Formula (C1) shown below).

(Reaction Formula (C1))

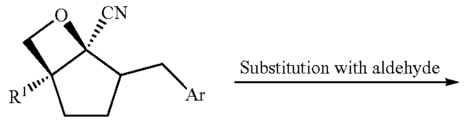

(5)

$R^1$ and Ar in Compound (15) are identical to $R^1$ and Ar in Compound (5), respectively.

A specific method for obtaining Compound (15) can be a method of subjecting a cyano group of Compound (5) to reduction and hydrolysis by reacting Compound (5) with diisobutylaluminum hydride (DIBALH) in a solvent.

The amount of diisobutylaluminum hydride employed per mole of Compound (5) is, for example, 0.2 to 20 moles, and preferably 0.5 to 10 moles.

The solvent includes: aromatic hydrocarbons such as benzene, toluene, xylene, and the like; ethers such as diethyl ether, tetrahydrofuran, dioxane, and the like; aliphatic hydrocarbons such as hexane, dichloromethane, and the like; and a mixture of at least two thereof. Preferable are toluene and hexane.

After the reduction, hydrolysis is carried out with water and an alcohol such as methanol or ethanol, in the presence of an acid catalyst. The acid catalyst includes tartaric acid, citric acid, and the like. Preferably employed is tartaric acid.

The reaction temperature for the reaction between diisobutylaluminum hydride and Compound (5) is, for example, in the range from −100° C. to 100° C., and preferably −78° C. to 30° C. The reaction time is, for example, 0.5 hour to 24 hours, and preferably 1 hour to 12 hours.

(Step C2: Reduction Reaction)

Next, an aldehyde group in Compound (15) is reduced, so that it is possible to obtain Compound (8a) (see Reaction Formula (C2) shown below).

(Reaction Formula (C2))

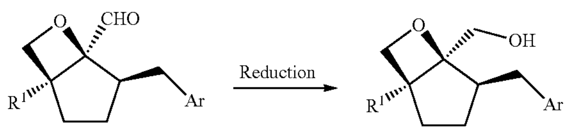

(15) (8a)

A reducing agent for reducing Compound (15) can be a hydride type reducing agent. For example, the hydride type reducing agent includes sodium borohydride, lithium borohydride, calcium borohydride, lithium aluminum hydride, and the like. Among these, sodium borohydride is preferably employed.

The amount of reducing agent employed per mole of Compound (15) is, for example, 0.2 to 20 moles, and preferably 0.3 to 10 moles.

The solvent include: alcohols such as methanol, ethanol, isopropanol, and the like; and ethers such as diethyl ether, tetrahydrofuran, dioxane, and the like. Among these, methanol, ethanol, and tetrahydrofuran are preferably employed.

The reaction temperature and reaction time can be appropriately selected depending upon the types of solvent as employed and reducing agent as employed and other conditions. For example, the reaction temperature is in the range from −100° C. to 100° C., and preferably −78° C. to 40° C. The reaction time is, for example, 0.1 hour to 24 hours, and preferably 0.5 hour to 12 hours.

To the steps undergone until Compound (11a) is obtained from Compound (8a), the Steps 8 through 10 of the first production method can be applied.

As described above, the third production method is a method for producing an azolylmethylcyclopentanol compound, including the step of reducing and hydrolyzing the compound represented by Formula (5), which compound is obtained by a method for producing an oxetane compound in accordance with the present invention, to obtain the compound represented by Formula (15).

According to the method for producing an oxetane compound in the present embodiment and the method for producing an azolylmethylcyclopentanol compound in the present embodiment, it is possible to produce Compound (8a) from Compound (5) through the two steps (Step C1 and Step C2). This makes it possible to reduce the number of steps as compared to the first and second production methods, thus improving practicality.

It should be noted that the reaction in the Step C1 proceeds only for a 1,5-cis form. For this reason, it is possible to selectively obtain only a 1,5-cis form for an azolylmethylcyclopentanol compound finally obtained, as in the case with the first production method.

As described above, according to a method for producing an oxetane compound according to the present embodiment, it is possible to obtain a ring-condensed oxetane compound through (i) cyanohydrin formation to convert a carbonyl group contained in an intermediate ketone to a cyanohydrin and (ii) ring closure reaction of a hydroxy group formed by the cyanohydrin formation with an adjacent alkyl group having a leaving group. At this time, by utilizing that the cyanohydrin formation is an equilibrium reaction, only an intermediate having a steric configuration corresponding to an oxetane compound is selectively caused to be out of the equilibrium reaction as a result of the ring closure. Consequently, a resultant compound converges to a desired oxetane compound. That is, according to a method for producing an oxetane compound in accordance with the present embodiment, it is possible to suitably produce an intermediate compound from which a specific geometrical isomer of a cyclic alcohol compound can be selectively obtained. Thus, according to a method for producing an azolylmethylcyclopentanol compound in accordance with the present embodiment, which method includes the method for producing an oxetane compound in accordance with the present embodiment, it is possible to selectively produce a specific geometrical isomer of azolylmethylcyclopentanol. Further, with use of an intermediate compound in accordance with the present embodiment, it is possible to selectively produce a specific geometrical isomer of a cyclic alcohol compound.

The term "room temperature" used herein refers to a temperature in the range from 10° C. to 30° C.

[Use of Azolylmethylcyclopentanol Compound]

The utilities of azolylmethylcyclopentanol compounds obtained by a production method according to the invention and with use of an intermediate according to the invention as an agro-horticultural agent and an industrial material protecting agent (hereinafter also referred to as "agro-horticultural agent and the like") are described below.

Since Compound (11) has a 1,2,4-triazolyl group or an imidazolyl group, it forms an acid addition salt of an inorganic acid or an organic acid, as well as a metal complex. Accordingly, Compound (11) can be employed also in the form of such an acid addition salt or the metal complex.

Compound (11) may have at least three asymmetric carbon atoms. Thus, depending on the composition, it may be a stereoisomer mixture (enantiomer or diastereomer) or either one of the stereoisomers. Accordingly, at least one of these stereoisomers can be employed also as an active ingredient of an agro-horticultural agent and the like.

(1) Plant Disease Controlling Effects

Compound (11) exhibits a controlling effect on a broad range of plant diseases. Applicable diseases are exemplified below. Soybean rust (*Phakopsora pachyrhizi, Phakopsora meibomiae*), rice blast (*Pyricularia grisea*), rice brown spot (*Cochliobolus miyabeanus*), rice leaf blight (*Xanthomonas oryzae*), rice sheath blight (*Rhizoctonia solani*), rice stem rot (*Helminthosporium sigmoideun*), rice Bakanae disease (*Gibberella fujikuroi*), rice bacterial seedling blight (*Pythium aphanidermatum*), apple powdery mildew (*Podosphaera leucotricha*), apple scab (*Venturia inaequalis*), apple blossom blight (*Monilinia mali*), apple *alternaria* blotch (*Alternaria alternata*), apple *valsa* canker (*Valsa mali*), pear black spot (*Alternaria kikuchiana*), pear powdery mildew (*Phyllactinia pyri*), pear rust (*Gymnosporangium asiaticum*), pear scab (*Venturia nashicola*), grape powdery mildew (*Uncinula necator*), grape downy mildew (*Plasmopara viticola*), grape ripe rot (*Glomerella cingulata*), barley powdery mildew (*Erysiphe graminis* f. sp *hordei*), barley stem rust (*Puccinia graminis*), barley stripe rust (*Puccinia striiformis*), barley stripe (*Pyrenophora graminea*), barley leaf blotch (*Rhynchosporium secalis*), wheat powdery mildew (*Erysiphe graminis* f. sp *tritici*), wheat brown rust (*Puccinia recondita*), wheat stripe rust (*Puccinia striiformis*), wheat eye spot (*Pseudocercosporella herpotrichoides*), wheat *Fusarium* blight (*Fusarium graminearum, Microdochium nivale*), wheat glume blotch (*Phaeosphaeria nodorum*), wheat leaf blight (*Septoria tritici*), gourd powdery mildew (*Sphaerotheca fuliginea*), gourd anthracnose (*Colletotrichum lagenarium*), cucumber downy mildew (*Pseudoperonospora cubensis*), cucumber *phytophthora* rot (*Phytophthora capsici*), tomato powdery mildew (*Erysiphe cichoracearum*), tomato early blight (*Alternaria solani*), eggplant powdery mildew (*Erysiphe cichoracearum*), strawberry powdery mildew (*Sphaerotheca humuli*), tobacco powdery mildew (*Erysiphe cichoracearum*), sugar beet *cercpspora* leaf spot (*Cercospora beticola*), maize smut (*Ustillaga maydis*), plum brown rot (*Monilinia fructicola*), various plants-affecting gray mold (*Botrytis cinerea*), *sclerotinia* rot (*Sclerotinia sclerotiorum*) and the like may be exemplified. Among these, it exhibits an effect superior to a commercially available metoconazol described in Patent Literature (Japanese Patent Application Publication Tokukaihei No. 01-93574 A (1989)) especially against wheat leaf blight (*Septoria tritici*) which is a critical disease in wheat.

Examples of applicable plants may be wild plants, cultivated plant cultivars, plants and cultivated plant cultivars obtained by conventional biological breeding such as heterologous mating or plasma fusion, and plants and cultivated plant cultivars obtained by gene engineering. The gene-engineered plants and the cultivated plant cultivars may for example be herbicide-resistant crops, vermin-resistant crops having insecticidal protein-producing genes integrated therein, disease-resistant crops having disease resistance inducer-producing genes integrated therein, palatably improved crops, productively improved crops, preservably improved crops, productively improved crops and the like. The gene-engineered cultivated plant cultivars may for example be those involving trade marks such as ROUNDUP READY, LIVERTY LINK, CLEARFIELD, YIELDGARD, HERCULEX, BLLGARD and the like.

(2) Plant Growth Promoting Effect

Furthermore, Compound (11) exhibits yield-increasing effects and quality-improving effects on a broad range of crops and horticultural plants by regulating the growth. Examples of such crops include: wheat, barley, oats, rice, rapeseed, sugarcane, corn, maize, soybean, pea, peanut, sugar beet, cabbage, garlic, radish, carrot, apple, pear, citric fruits such as mandarin, orange, lemon and the like, peach, cherry, avocado, mango, papaya, red pepper, cucumber, melon, strawberry, tobacco, tomato, eggplant, turf, chrysanthemum, azalea, and other ornamental plants.

(3) Industrial Material Protecting Effect

Moreover, Compound (11) exhibits an excellent ability of protecting an industrial material from a broad spectrum of hazardous microorganisms which invade such a material. Examples of such microorganisms include: paper/pulp deteriorating microorganisms (including slime-forming microorganisms) such as *Aspergillus* sp., *Trichoderma* sp., *Penicillium* sp., *Geotrichum* sp., *Chaetomium* sp., *Cadophora* sp., *Ceratostomella* sp., *Cladosporium* sp., *Corticium* sp., *Lentinus* sp., *Lezites* sp., *Phoma* sp., *Polysticus* sp., *Pullularia* sp., *Stereum* sp., *Trichosporium* sp., *Aerobacter* sp., *Bacillus* sp., *Desulfovibrio* sp., *Pseudomonas* sp., *Flavobacterium* sp., and *Micrococcus* sp.; fiber-deteriorating microorganisms such as *Aspergillus* sp., *Penicillium* sp., *Chaetomium* sp., *Myrothecium* sp., *Curvularia* sp., *Gliomastix* sp., *Memnoniella* sp., *Sarcopodium* sp., *Stachybotrys* sp., *Stemphylium* sp., *Zygorhynchus* sp., *Bacillus* sp., and *Staphylococcus* sp.; lumber-deteriorating fungi such as *Tyromyces palustris, Coriolus versicolor, Aspergillus* sp., *Penicillium* sp., *Rhizopus* sp., *Aureobasidium* sp., *Gliocladium* sp., *Cladosporium* sp., *Chaetomium* sp. and *Trichoderma* sp.; leather-deteriorating microorganisms such as *Aspergillus* sp., *Penicillium* sp., *Chaetomium* sp., *Cladosporium* sp., *Mucor* sp., *Paecilomyces* sp., *Pilobus* sp., *Pullularia* sp., *Trichosporon* sp. and *Tricothecium* sp.; rubber/plastic-deteriorating microorganisms such as *Aspergillus* sp., *Penicillium* sp., *Rhizopus* sp., *Trichoderma* sp., *Chaetomium* sp., *Myrothecium* sp., *Streptomyces* sp., *Pseudomonas* sp., *Bacillus* sp., *Micrococcus* sp., *Serratia* sp., *Margarinomyces* sp. and *Monascus* sp.; paint-deteriorating microorganisms such as *Aspergillus* sp., *Penicillium* sp., *Cladosporium* sp., *Aureobasidium* sp., *Gliocladium* sp., *Botryodiplodia* sp., *Macrosporium* sp., *Monilia* sp., *Phoma* sp., *Pullularia* sp., *Sporotrichum* sp., *Trichoderma* sp., *Bacillus* sp., *Proteus* sp., *Pseudomonas* sp. and *Serratia* sp.

(4) Formulations

An agro-horticultural formulation containing Compound (11) as an active ingredient may contain various components other than Compound (11). The agro-horticultural formulation containing Compound (11) as an active ingredient can be mixed with a solid carrier, a liquid carrier, a surfactant, and other formulation auxiliary agents. The dosage form of the agro-horticultural formulation containing Compound (11) as an active ingredient may for example be a dust formulation, wettable powder, granule, emulsifiable concentrate and the like.

The agro-horticultural formulation may contain Compound (11) as an active ingredient in an amount of 0.1 to 95% by weight based on the total amount of the agro-horticultural formulation. Compound (11) as an active ingredient is contained preferably in an amount of 0.5 to 90% by weight, and more preferably 2 to 80% by weight.

Carriers, diluents and surfactants employed as formulation auxiliary agents are exemplified below. The solid carriers include talc, kaolin, bentonite, diatomaceous earth, white carbon, clay and the like. The liquid diluents include water, xylene, toluene, chlorobenzene, cyclohexane, cyclohexanone, dimethyl sulfoxide, dimethylformamide, alcohols and the like. The surfactant may appropriately be selected for an intended effect. The emulsifier may for example be polyoxiethylene alkylaryl ether, polyoxyethylene sorbitan monolaurate and the like, the dispersing agent may for example be lignin sulfonate, dibutylnaphthalene sulfonate and the like, and the wetting agent may for example be an alkyl sulfonate, alkylphenyl sulfonate and the like.

The formulation may be used as it is, or used as being diluted in a diluent such as water to a certain concentration. The concentration of Compound (11) when used as being diluted is preferably 0.001% to 1.0%. The amount of Compound (11) for 1 ha of the agro-horticultural field such as a farm, paddy field, orchard, greenhouse and the like is 20 to 5000 g, and more preferably 50 to 2000 g. Since these concentration and amount to be used may vary depending on the dosage form, timing of use, method of use, place of use, subject crop and the like, they can be increased or decreased regardless of the ranges mentioned above.

In addition, Compound (11) can be combined with other active ingredients, including bactericides, insecticides, acaricides, herbicides and the like, such as those listed below, thereby enabling the use as an agro-horticultural agent having an enhanced performance.

<Anti-Bacterial Substances>

Acibenzolar-5-methyl, 2-phenylphenol (OPP), azaconazole, azoxystrobin, amisulbrom, bixafen, benalaxyl, benomyl, benthiavalicarb-isopropyl, bicarbonate, biphenyl, bitertanol, blasticidin-S, borax, Bordeaux mixture, boscalid, bromuconazole, bronopol, bupirimate, sec-butylamine, calcium polysulphide, captafol, captan, carbendazim, carboxin, carpropamid, quinomethionate, chloroneb, chloropicrin, chlorothalonil, chlozolinate, cyazofamid, cyflufenamid, cymoxanil, cyproconazole, cyprodinil, dazomet, debacarb, dichlofluanid, diclocymet, diclomezine, dicloran, diethofencarb, difenoconazole, diflumetorim, dimethomorph, dimoxystrobin, diniconazole, dinocap, diphenylamine, dithianon, dodemorph, dodine, edifenphos, epoxiconazole, ethaboxam, ethoxyquin, etridiazole, enestroburin, famoxadone, fenamidone, fenarimol, fenbuconazole, fenfuram, fenhexamid, fenoxanil, fenpiclonil, fenpropidin, fenpropimorph, fentin, ferbam, ferimzone, fluazinam, fludioxonil, flumorph, fluoroimide, fluoxastrobin, fluquinconazole, flusilazole, flusulfamide, flutolanil, flutriafol, folpet, fosetyl-Al, fuberidazole, furalaxyl, furametpyr, fluopicolide, fluopyram, guazatine, hexachlorobenzene, hexaconazole, hymexazol, imazalil, imibenconazole, iminoctadine, ipconazole, iprobenfos, iprodione, iprovalicarb, isoprothiolane, isopyrazam, isotianil, kasugamycin, copper preparations, such as copper hydroxide, copper naphthenate, copper oxychloride, copper sulfate, copper oxide, oxine copper, kresoxim-methyl, mancopper, mancozeb, maneb, mandipropamid, mepanipyrim, mepronil, metalaxyl, metconazole, metiram, metominostrobin, mildiomycin, myclobutanil, nitrothal-isopropyl, nuarimol, ofurace, oxadixyl, oxolinic acid, oxpoconazole, oxycarboxin, oxytetracycline, pefurazoate, orysastrobin, penconazole, pencycuron, penthiopyrad, pyribencarb, fthalide, picoxystrobin, piperalin, polyoxin, probenazole, prochloraz, procymidone, propamocarb, propiconazole, propineb, proquinazid, prothioconazole, pyraclostrobin, pyrazophos, pyrifenox, pyrimethanil, pyroquilon, quinoxyfen, quintozene, silthiopham, simeconazole, spiroxamine, sulfur and sulfur formulations, tebuconazole, tecloftalam, tecnazen, tetraconazole, thiabendazole, thifluzamide, thiophanate-methyl, thiram, thiadinil, tolclofos-methyl, tolylfluanid, triadimefon, triadimenol, triazoxide, tricyclazole, tridemorph, trifloxystrobin, triflumizole, triforine, triticonazole, validamycin, vinclozolin, zineb, ziram, zoxamide, amisulbrom, sedaxane, flutianil, valiphenal, ametoctradin, dimoxystrobin, metrafenone, hydroxyisoxazole, metasulfocarb and the like.

<Insecticides/Acaricides/Nematocides>

Abamectin, acephate, acrinathrin, alanycarb, aldicarb, allethrin, amitraz, avermectin, azadirachtin, azamethiphos, azinphos-ethyl, azinphos-methyl, azocyclotin, *Bacillus firmus, Bacillus subtilis, Bacillus thuringiensis*, bendiocarb, benfuracarb, bensultap, benzoximate, bifenazate, bifenthrin, bioallethrin, bio resmethrin, bis trifluoron, buprofezin, butocarboxim, butoxycarboxim, cadusafos, carbaryl, carbofuran, carbosulfan, cartap, CGA50439, chlordane, chlorethoxyfos, chlorphenapyr, chlorfenvinphos, chlorfluazuron, chlormephos, chlorpyrifos, chlorpyrifos methyl, chromafenozide, clofentezine, clothianidin, chlorantraniliprole, coumaphos, cryolite, cyanophos, cycloprothrin, cyfluthrin, cyhalothrin, cyhexatin, cypermethrin, cyphenothrin, cyromazine, Cyazapyr, cyenopyrafen, DCIP, DDT, deltamethrin, demeton-5-methyl, diafenthiuron, diazinon, dichlorophen, dichloropropene, dichlorvos, dicofol, dicrotophos, dicyclanil, diflubenzuron, dimethoate, dimethylvinphos, dinobuton, dinotefuran, emamectin, endosulfan, EPN, esfenvalerate, ethiofencarb, ethion, ethiprole, ethofenprox, ethoprophos, etoxazole, famphur, fenamiphos, fenazaquin, fenbutatin oxide, fenitrothion, fenobucarb, fenothiocarb, fenoxycarb, fenpropathrin, fenpyroximate, fenthion, fenvalerate, fipronil, flonicamid, fluacrypyrim, flucycloxuron, flucythrinate, flufenoxuron, flumethrin, fluvalinate, flubendiamide, formetanate, fosthiazate, halfenprox, furathiocarb, halofenozide, gamma-HCH, heptenophos, hexaflumuron, hexythiazox, hydramethylnon, imidacloprid, imiprothrin, indoxacarb, isoprocarb, isoxathion, lufenuron, malathion, mecarbam, metam, methamidophos, methidathion, methiocarb, methomyl, methoprene, methothrin, methoxyfenozide, metolcarb, milbemectin, monocrotophos, naled, nicotine, nitenpyram, novaluron, noviflumuron, omethoate, oxamyl, oxydemethon methyl, parathion, permethrin, phenthoate, phorate, phosalone, phosmet, phosphamidon, phoxim, pirimicarb, pirimiphos-methyl, profenofos, propoxur, prothiophos, pymetrozin, pyrachlophos, pyrethrin, pyridaben, pyridalyl, pyrimidifen, pyriproxifen, pyrifluquinazon, pyriprole, quinalphos, silafluofen, spinosad, spirodiclofen, spiromesifen, spirotetramat, sulfluramid, sulphotep, SZI-121, tebufenozid, tebufenpyrad, tebupirimphos, teflubenzuron, tefluthrin, temephos, terbufos, tetrachlorvinphos, thiacloprid, thiamethoxam, thiodicarb, thiofanox, thiometon, tolfenpyrad, tralomethrin, tralopyril, triazamate, triazophos, trichlorfon, triflumuron, vamidothion, valifenal, XMC, xylylcarb, imicyafos, lepimectin and the like.

<Plant Growth Regulators>

Ancymidol, 6-benzylaminopurine, paclobutrazol, diclobutrazole, uniconazole, methylcyclopropene, mepiquat chloride, ethefon, chlormequat chloride, inabenfide, prohexadione and its salts, trinexapac-ethyl and the like. As plant hormones, jasmonic acid, brassinosteoid, gibberellin and the like.

An industrial material protecting agent containing Compound (11) as an active ingredient may contain various components other than Compound (11). The industrial material protecting agent containing Compound (11) as an active ingredient can be used as being dissolved or dispersed in a suitable liquid carrier or as being mixed with a solid carrier. The industrial material protecting agents containing Compound (11) as an active ingredient may further contain an emulsifier, dispersing agent, spreading agent, penetrating agent, wetting agent, stabilizer and the like. The dosage form of the industrial material protecting agents containing Compound (11) as an active ingredient may for example be a wettable powder, powder, granule, tablet, paste, suspension, spray and the like. The industrial material protecting agents containing Compound (11) as an active ingredient may contain other biocides, insecticides, deterioration-preventing agent and the like.

The liquid carrier may be any liquid as long as it does not react with an active ingredient. The liquid carrier may for example be water, alcohols (for example, methyl alcohol, ethyl alcohol, ethylene glycol, cellosolve and the like), ketones (for example, acetone, methylethylketone and the like), ethers (for example, dimethyl ether, diethyl ether, dioxane, tetrahydrofuran and the like), aromatic hydrocarbons (for example, benzene, toluene, xylene, methylnaphthalene and the like), aliphatic hydrocarbons (for example, gasoline, kerosene, paraffin oil, machine oil, fuel oil and the like), acid amides (for example, dimethylformamide, N-methylpyrrolidone and the like), halogenated hydrocarbons (for example, chloroform, carbon tetrachloride and the like), esters (for example, acetic acid ethyl ester, fatty acid glycerin ester and the like), nitriles (for example, acetonitrile and the like), and dimethyl sulfoxide and the like.

The solid carrier may for example be a microparticle or a granule of kaolin clay, bentonite, acid clay, pyrophylite, talc, diatomaceous earth, calcite, urea, ammonium sulfate and the like.

The emulsifiers and the dispersing agents may for example be soaps, alkyl sulfonates, alkylaryl sulfonates, dialkyl sulfosuccinates, quaternary ammonium salts, oxyalkylamines, fatty acid esters, polyalkylene oxide-based, anhydrosorbitol-based surfactants.

When Compound (11) is contained as an active ingredient in a formulation, it is added in such an amount that the concentration becomes 0.1 to 99.9% by weight based on the entire amount of the formulation, although the content may vary depending on the dosage form and the purpose of use. Upon being used practically, it is combined appropriately with a solvent, diluent, extender and the like so that the treatment concentration is usually 0.005 to 5% by weight, and preferably 0.01 to 1% by weight.

As described above, an azolylmethylcyclopentanol compound represented by Compound (11) exhibits an excellent biocidal effect on a large number of microorganisms which induce diseases in plants. Thus, an agro-horticultural disease controlling agent containing an azolylmethylcyclopentanol compound represented by Compound (11) as an active ingredient has a low toxicity to humans and animals, are capable of being handled safely, and exhibits a high controlling effect on a wide range of plant diseases.

The following will provide Examples to more specifically describe embodiments of the present invention. As a matter of course, the present invention is not limited to Examples provided below, but details of the present invention can be realized in various manners. Further, the invention is not limited to the embodiments described above, and it may be varied in various ways within the scope of the appended Claims. Thus, an embodiment achieved by combining technical means varied appropriately within the scope of the appended claims will be included by the technical scope of the invention. All of the literatures referred herein are incorporated by reference herein.

EXAMPLES

Example 1

Production Example 1

Synthesis of 1-(4-chlorobenzyl)-3-hydroxymethyl-3-methyl-2-oxo-cyclopentancarboxylic acid methyl ester (Compound 2-1)

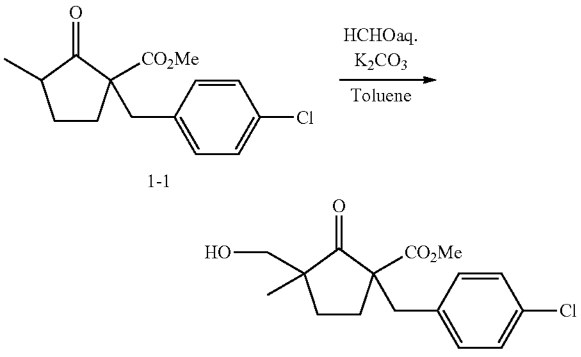

1-1

2-1

To 1.12 g of 1-(4-chlorobenzyl)-3-methyl-2-oxo-cyclopentancarboxylic acid methyl ester (Compound 1-1), which is a known compound, 0.90 ml of 37% aqueous solution of formaldehyde and 276 mg of potassium carbonate were added, and the resulting mixture was vigorously stirred at room temperature for 4 hours. After the reaction, water was added to the reaction solution thus obtained, and extraction with ethyl acetate was then carried out. The organic layer thus extracted was washed with saturated brine and then dried over anhydrous sodium sulfate. The solvent was distilled away, and the residue was then purified by silica gel column chromatography to obtain 1.180 g of Compound 2-1.

In a similar method as in the present production example, compounds represented by Formula (2) below were synthesized, wherein their respective combinations of $R^1$ and Ar were as listed in Table 1.

TABLE 1

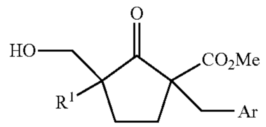

(2)

| Compound No. | $R^1$ | Ar |
|---|---|---|
| 2-2 | $CH_3$ | 4-FluoroPhenyl |
| 2-3 | $CH_3$ | Phenyl |
| 2-4 | $CH_3$ | 2-FluoroPhenyl |
| 2-5 | $CH_3CH_2$ | 4-ChloroPhenyl |
| 2-6 | $CH_3$ | 3-ChloroPhenyl |
| 2-7 | $CH_3$ | 4-TrifluoromethoxyPhenyl |
| 2-8 | $CH_3$ | 4-MethylPhenyl |
| 2-9 | $CH_3$ | 2,4-Difluoro-Phenyl |
| 2-10 | $CH_3$ | 2-ChloroPyridin-5-yl |
| 2-11 | $CH_3$ | 5-ChloroThiophen-2-yl |
| 2-12 | $CH_3$ | 2-ChloroThiazol-5-yl |

Production Example 2

Synthesis of 1-(4-chlorobenzyl)-3-methanesulfonyloxymethyl-3-methyl-2-oxo-cyclopentancarboxylic acid methyl ester (Compound 3-1-1)

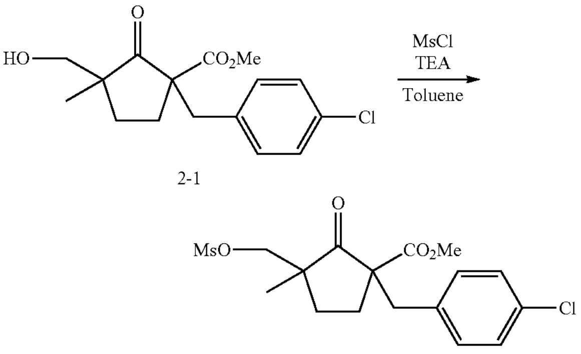

2-1

3-1-1

In 20 ml of methylene chloride, 1.00 g of Compound 2-1 obtained in Production Example 1 was dissolved. To the solution thus obtained, 0.68 ml of triethylamine and 0.324 ml of methanesulfonyl chloride were added. Thereafter, the resulting mixture was stirred at room temperature for 1.5 hours. After the reaction, water was added to the reaction solution thus obtained, and extraction with ethyl acetate was then carried out. The organic layer thus extracted was washed with an aqueous solution of sodium hydrogen carbonate and saturated brine and then dried over anhydrous sodium sulfate.

The solvent was distilled away, and the residue was then purified by silica gel column chromatography to obtain 1.141 g of Compound 3-1-1.

Production Example 3

Synthesis of 1-(4-chlorobenzyl)-3-(4-toluenesulfonyloxy)methyl-3-methyl-2-oxo-cyclopentancarboxylic acid methyl ester (Compound 3-1-2)

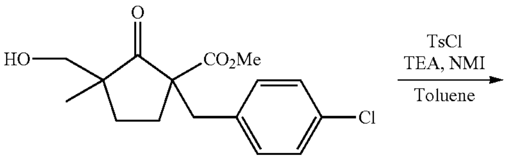

2-1

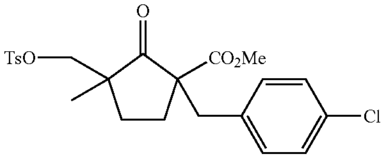

3-1-2

In 95 ml of toluene, 4.756 g of Compound 2-1 obtained in Production Example 1 was dissolved. To the solution thus obtained, 3.12 ml of triethylamine and 1.76 ml of N-methylimidazole were added, and 3.38 g of 4-toluenesulfonyl chloride was added. The resulting mixture was stirred at room temperature for 100 minutes. After the reaction, water was added to the reaction solution thus obtained, and the organic layer was separated from the suspension. Thereafter, the aqueous layer was extracted with toluene and then blended with the organic layer previously obtained. The resultant organic layer thus obtained was washed with an aqueous solution of 1 mol/l hydrochloric acid and saturated brine and then dried over anhydrous sodium sulfate. The solvent was distilled away, and the residue was then purified by silica gel column chromatography to obtain 5.397 g of Compound 3-1-2.

Production Example 4

Synthesis of 1-(4-chlorobenzyl)-3-chloromethyl-3-methyl-2-oxo-cyclopentancarboxylic acid methyl ester (Compound 3-1-3)

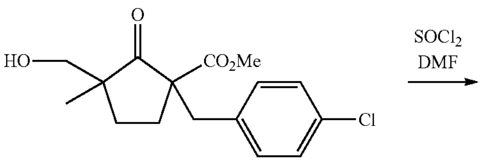

2-1

-continued

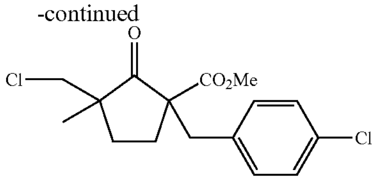

3-1-3

To 8.79 g of Compound 2-1 obtained in Production Example 1, 3.04 ml of thionyl chloride and 0.15 ml of DMF were added. The resulting mixture was stirred in an oil bath of 90° C. for 2.5 hours. After the reaction, water was added to the reaction solution thus obtained, and extraction with toluene was carried out. The organic layer thus extracted was washed with a saturated aqueous solution of sodium carbonate and saturated brine and then dried over anhydrous sodium sulfate. The solvent was distilled away, and the residue was then purified by silica gel column chromatography to obtain 6.57 g of Compound 3-1-3.

Production Example 5

Synthesis of methanesulfonic acid 3-(4-chlorobenzyl)-1-methyl-2-oxo-cyclopentylmethyl ester (Compound 4-1-1) and 2-bromomethyl-5-(4-chlorobenzyl)-2-methylcyclopentanone (Compound 4-1-4)

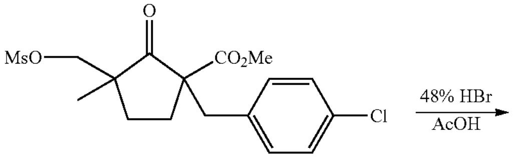

3-1-1

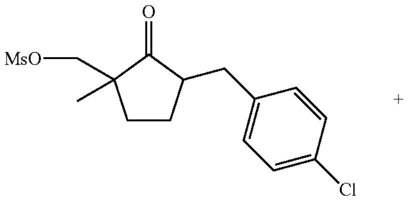

4-1-1

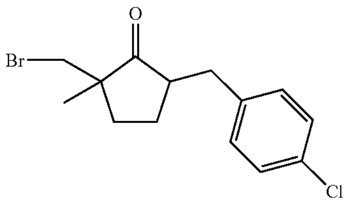

4-1-4

In 1.13 ml of acetic acid, 754.8 mg of Compound 3-1-1 synthesized in Production Example 2 was dissolved. To the solution thus obtained, 1.13 ml of 47% aqueous solution of hydrobromic acid was added, and the mixture solution thus obtained was then stirred at 110° C. for 1.5 hours. After the reaction, water was added to the reaction solution thus obtained, and extraction with ethyl acetate was then carried out. The extract was washed with an aqueous solution of sodium hydrogen carbonate, water, and saturated brine and then dried over anhydrous sodium sulfate. The solvent was distilled away, and the residue was then purified by silica gel column chromatography (hexane/ethyl acetate=5/1) to obtain 365.1 mg of Compound 4-1-4. Simultaneously, 138.4 mg of Compound 4-1-1 was obtained in a hexane:ethyl acetate fraction of 1:1.

Production Example 6

Synthesis of Methanesulfonic acid 3-(4-chlorobenzyl)-1-methyl-2-oxo-cyclopentylmethyl ester (Compound 4-1-1)

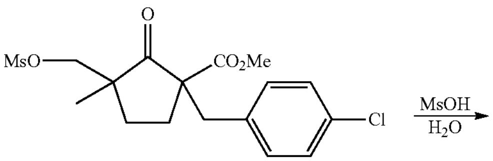

3-1-1

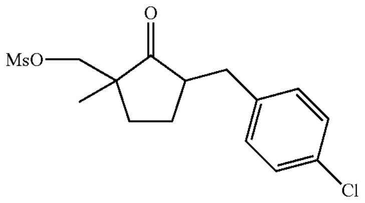

4-1-1

To 1.26 g of Compound 3-1-1 obtained in Production Example 2, 0.255 ml of methanesulfonic acid and 88.3 mg of water were added, and the resulting mixture was stirred at 110° C. for 3.5 hours. After the reaction, water was added to the reaction solution thus obtained, and extraction with ethyl acetate was then carried out. The extract was washed with an aqueous solution of sodium hydrogen carbonate and saturated brine. After the organic layer was dried over anhydrous sodium sulfate, the solvent was distilled away.

The residue was purified by silica gel column chromatography to obtain 794 mg of Compound 4-1-1.

Production Example 7

Synthesis of 4-toluenesulfonic acid 3-(4-chlorobenzyl)-1-methyl-2-oxo-cyclopentylmethyl ester (Compound 4-1-2)

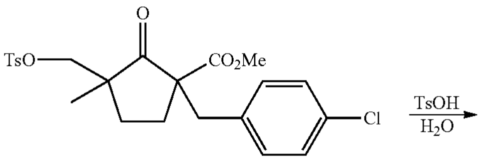

3-1-2

-continued

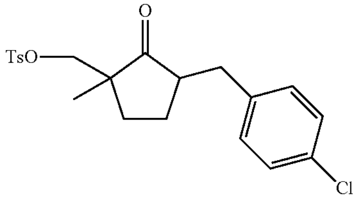

4-1-2

To 521 mg of Compound 3-1-2 synthesized in Production Example 3, 256 mg of 4-toluenesulfonic acid monohydrate and 32.3 μl of water were added, and the resulting mixture was stirred at 80° C. for 38.5 hours. After the reaction, water was added to the reaction solution thus obtained, and extraction with ethyl acetate was then carried out. The extract was washed with an aqueous solution of sodium hydrogen carbonate and saturated brine. After the organic layer was dried over anhydrous sodium sulfate, the solvent was distilled away. The residue was purified by silica gel column chromatography to obtain 361.1 mg of Compound 4-1-2.

Production Example 8

Synthesis of 5-(4-chlorobenzyl)-2-chloromethyl-2-methyl-cyclopentanone (Compound 4-1-3)

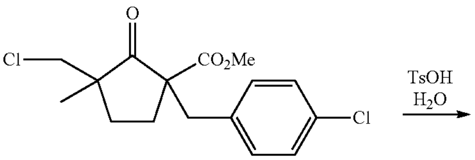

3-1-3

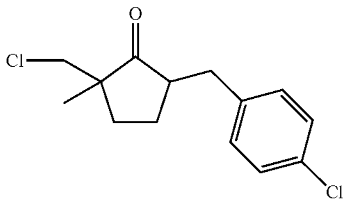

4-1-3

To 1.00 g of Compound 3-1-3 synthesized in Production Example 4, 0.578 g of toluenesulfonic acid monohydrate and 100 mg of water were added, and the resulting mixture was stirred in an oil bath of 120° C. for 1.5 hours. After the reaction, water was added to the reaction solution thus obtained, and extraction with ethyl acetate was then carried out. The extract was washed with an aqueous solution of sodium hydrogen carbonate and saturated brine. After the organic layer was dried over anhydrous sodium sulfate, the solvent was distilled away. The residue was purified by silica gel column chromatography to obtain 752 mg of Compound 4-1-3.

Production Example 9

Synthesis 1 of (1RS,5RS)-4-(4-chlorobenzyl)-1-methyl-6-oxa-bicyclo[3,2,0]heptane-5-carbonitrile (Compound 5-1)

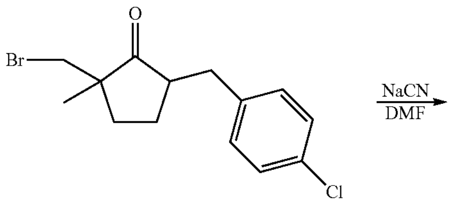

4-1-4

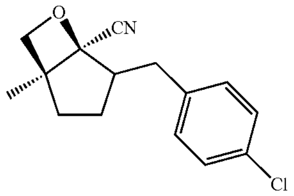

5-1

In 3.2 ml of dimethylformamide, 200 mg of Compound 4-1-4 synthesized in Production Example 5 was dissolved. To the solution thus obtained, 31.1 mg of sodium cyanide was added, and the resulting mixture was stirred at room temperature for 21 hours. After the reaction, water was added to the reaction solution thus obtained, and extraction with ethyl acetate was then carried out. The organic layer was washed with saturated brine and then dried over anhydrous sodium sulfate. The solvent was distilled away, and the residue was then purified by silica gel column chromatography to obtain 114.3 mg of Compound 5-1 containing two kinds of isomers.

The following shows the analysis result.

1,5-cis Form:

$^1$H-NMR ($CDCl_3$) δ=

1.39-1.48 (1H, m), 1.46 (3H, s), 1.85-1.94 (2H, m), 1.95-2.01 (1H, m), 2.15-2.26 (1H, m), 2.71 (1H, dd, J=13.7, 9.4 Hz), 2.93 (1H, dd, J=13.7, 5.6 Hz), 4.26 (1H, d, J=6.0 Hz), 4.52 (1H, dd, J=6.0, 1.5 Hz), 7.13 (2H, d, J=8.4 Hz), 7.26 (2H, d, J=8.4 Hz).

1,5-trans Form:

$^1$H-NMR ($CDCl_3$) δ=

1.51 (3H, s), 1.61-1.71 (1H, m), 1.72-1.78 (1H, m), 1.85-1.92 (1H, m), 2.15 (dd, J=13.8, 12.7 Hz), 2.21-2.32 (1H, m), 2.48-2.56 (1H, m), 2.93 (1H, dd, J=13.8, 4.2 Hz), 4.22 (1H, d, J=5.9 Hz), 4.53 (1H, dd, J=5.9, 1.6 Hz), 7.08 (2H, d, J=8.4 Hz), 7.29 (2H, d, J=8.4 Hz).

Production Example 10

Synthesis 2 of Compound 5-1

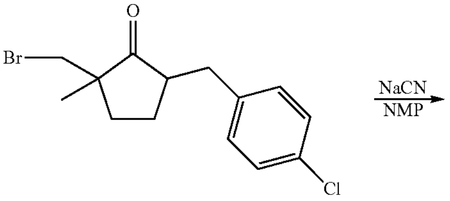

4-1-4

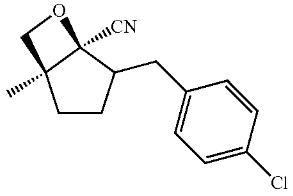

5-1

In 1 ml of N-methyl-2-pyrrolidone, 200 mg of Compound 4-1-4 synthesized in Production Example 5 was dissolved. To the solution thus obtained, 34.3 mg of sodium cyanide was added, and the resulting mixture was then stirred at room temperature for 20 hours. After the reaction, purification was carried out as in Production Example 9 to obtain 135.1 mg of Compound 5-1.

Production Example 11

Synthesis 3 of Compound 5-1

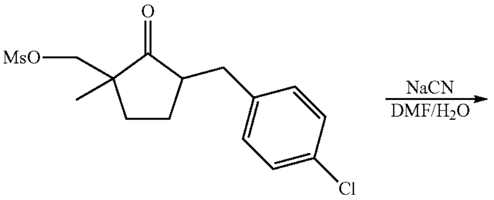

4-1-1

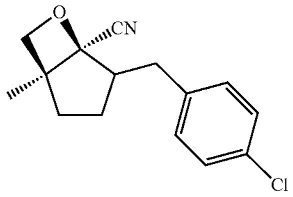

5-1

In 0.5 ml of water, 97.3 mg of sodium cyanide was dissolved. In 2.5 ml of DMF, 505 mg of Compound 4-1-1 obtained in Production Example 6 was dissolved, and the solution thus obtained was added to the aqueous solution of sodium cyanide. The resulting mixture was stirred at room temperature for 77 hours. Thereafter, water was added to the reaction solution thus obtained, and extraction with toluene was then carried out. The organic layer thus extracted was washed with water and saturated brine and then dried over anhydrous sodium sulfate. The solvent was distilled away, and the residue was then purified by silica gel column chromatography to obtain 326.4 mg of Compound 5-1.

Production Example 12

Synthesis 4 of Compound 5-1

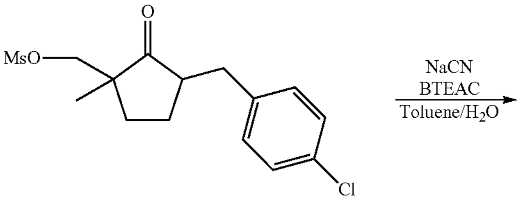

4-1-1

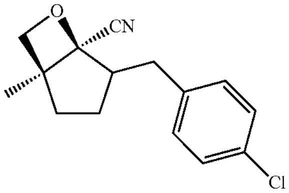

5-1

In 0.5 ml of water, 96.3 mg of sodium cyanide was dissolved. In 1 ml of toluene, 500 mg of Compound 4-1-1 obtained in Production Example 6 was dissolved, and the solution thus obtained was added to the aqueous solution of sodium cyanide. To the resulting mixture, 34.4 mg of benzyltriethylammonium chloride (BTEAC) was added, and the resulting mixture was then stirred at 70° C. for 20 hours. Thereafter, water was added to the reaction solution thus obtained, and extraction with toluene was then carried out. The organic layer thus extracted was purified as in Production Example 11 to obtain 305.9 mg of Compound 5-1.

Production Example 13

Synthesis 5 of Compound 5-1

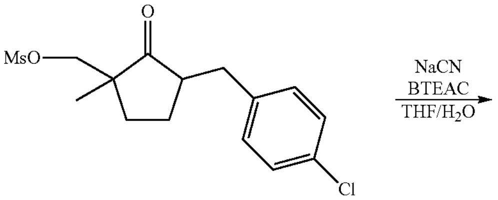

4-1-1

-continued

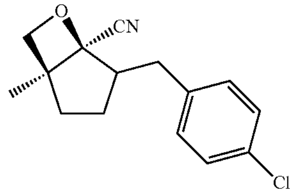

5-1

In 0.5 ml of water, 96.9 mg of sodium cyanide was dissolved. In 1 ml of THF, 503 mg of Compound 4-1-1 obtained in Production Example 6 was dissolved, and the solution thus obtained was added to the aqueous solution of sodium cyanide. To the resulting mixture, 34.6 mg of benzyltriethylammonium chloride was added, and the resulting mixture was then stirred at 70° C. for 23 hours. Thereafter, water was added to the reaction solution thus obtained, and extraction with toluene was then carried out. The organic layer thus extracted was purified as in Production Example 11 to obtain 294.3 mg of Compound 5-1.

Production Example 14

Synthesis 6 of Compound 5-1

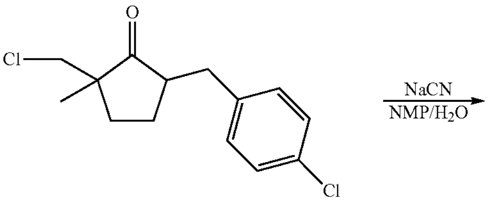

4-1-3

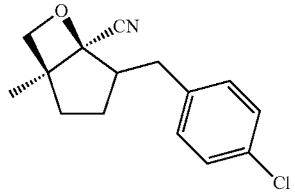

5-1

In 0.78 ml of water, 190.5 mg of sodium cyanide was dissolved. In 3.9 ml of NMP, 779.1 mg of Compound 4-1-3 obtained in Production Example 8 was dissolved, and the solution thus obtained was added to the aqueous solution of sodium cyanide. The resulting mixture was stirred at room temperature for 264 hours. Thereafter, water was added to the reaction solution thus obtained, and extraction with toluene was then carried out. The organic layer thus extracted was washed with water and saturated brine and then dried over anhydrous sodium sulfate. The solvent was distilled away, and the residue was then purified by silica gel column chromatography to obtain 535 mg of Compound 5-1.

Production Example 15

Synthesis 7 of Compound 5-1

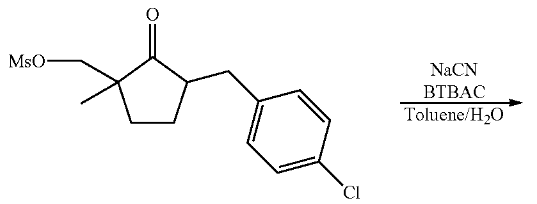

4-1-1

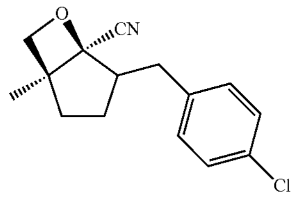

5-1

In 0.3 ml of water, 97.0 mg of sodium cyanide was dissolved. In 1 ml of toluene, 503 mg of Compound 4-1-1 obtained in Production Example 6 was dissolved, and the solution thus obtained was added to the aqueous solution of sodium cyanide. To the resulting mixture, 47.6 mg of benzyltributylammonium chloride (BTBAC) was added, and the resulting mixture was then stirred at room temperature for 24 hours. Thereafter, water was added to the reaction solution thus obtained, and extraction with toluene was then carried out. Purification was carried out as in Production Example 14 to obtain 367.1 mg of Compound 5-1.

Production Example 16

Synthesis of (1RS,5RS)-4-(4-chlorobenzyl)-1-ethyl-6-oxa-bicyclo[3,2,0]heptane-5-carbonitrile (Compound 5-5)

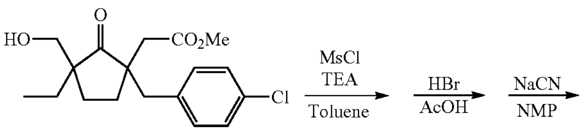

2-5

-continued

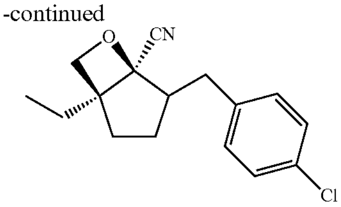

5-5

In 32 ml of toluene, 3.17 g of Compound 2-5 obtained as in Production Example 1 was dissolved. The solution thus obtained was mixed with 1.88 ml of triethylamine and 0.960 ml of methanesulfonyl chloride, and the mixture solution thus obtained was stirred at room temperature for 46 minutes. After the reaction, an aqueous solution of hydrochloric acid was added to the reaction solution thus obtained, and extraction with ethyl acetate was then carried out. The organic layer thus extracted was washed with an aqueous solution of sodium hydrogen carbonate and saturated brine and then dried over anhydrous sodium sulfate. The solvent was distilled away, and the residue was then dissolved in 6.0 ml of acetic acid. To the solution thus obtained, 6.0 ml of 47% aqueous solution of hydrobromic acid was added, and the resulting mixture was then stirred at 110° C. for 4 hours. After the reaction, water was added to the reaction solution thus obtained, and extraction with toluene was then carried out. The extract was washed with an aqueous solution of sodium hydrogen carbonate, water, and saturated brine and then dried over anhydrous sodium sulfate. The solvent was distilled away, and the residue was then dissolved in 17 ml of N-methyl-2-pyrrolidone. To the solution thus obtained, 621 mg of sodium cyanide was added, and the resulting mixture was stirred at room temperature for 72 hours. After the reaction, saline was added to the reaction solution thus obtained, and extraction with ethyl acetate was carried out. The organic layer thus extracted was washed with saturated brine and then dried over anhydrous sodium sulfate. The solvent was distilled away, and the residue was then purified by silica gel column chromatography to obtain 1.382 g of Compound 5-5. (1,5-cis Form)

$^1$H-NMR ($CDCl_3$) δ=

0.88 (3H, t, J=7.5 Hz), 1.40-1.49 (1H, m), 1.66-1.76 (1H, m), 1.84-2.04 (3H, m), 2.07-2.23 (2H, m), 2.70 (1H, dd, J=13.7, 9.6 Hz), 2.94 (1H, dd, J=13.7, 5.5 Hz), 4.22 (1H, d, J=6.0 Hz), 4.56 (1H, dd, J=6.0, 1.5 Hz), 7.13 (2H, d, J=8.4 Hz), 7.26 (1H, d, J=8.4 Hz).

In a similar method as in the present production example, compounds represented by Formula (5) below were synthesized, wherein their respective combinations of $R^1$ and Ar were as listed in Table 2.

TABLE 2

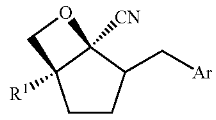

(5)

| Compound No. | $R^1$ | Ar |
|---|---|---|
| 5-2 | $CH_3$ | 4-FluoroPhenyl |
| 5-3 | $CH_3$ | Phenyl |
| 5-4 | $CH_3$ | 2-FluoroPhenyl |
| 5-7 | $CH_3$ | 4-TrifluoromethoxyPhenyl |

TABLE 2-continued (5)

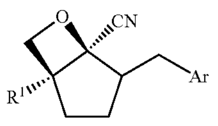

| Compound No. | $R^1$ | Ar |
|---|---|---|
| 5-8 | $CH_3$ | 4-MethylPhenyl |
| 5-9 | $CH_3$ | 2,4-Difluoro-Phenyl |
| 5-10 | $CH_3$ | 5-Chloro-Pyridin-2-yl |
| 5-11 | $CH_3$ | 5-Chloro-Thiophen-2-yl |
| 5-12 | $CH_3$ | 2-Chloro-Thiazol-5-yl |

The following shows the respective analysis results of the compounds obtained above. Note that NMR spectra are shown for the 1,5-cis forms only.

(Compound 5-2)

$^1$H-NMR ($CDCl_3$) δ=

1.39-1.50 (1H, m), 1.46 (3H, s), 1.87-2.05 (3H, m), 2.19-2.26 (1H, m), 2.72 (1H, dd, J=13.6, 9.2 Hz), 2.95 (1H, dd, J=13.6, 5.6 Hz), 4.25 (1H, d, J=6.0 Hz), 4.53 (1H, dd, J=6.0, 1.2 Hz), 6.98 (2H, t, 8.6 Hz), 7.16 (2H, dd, J=8.6, 5.4 Hz).

(Compound 5-3)

$^1$H-NMR ($CDCl_3$) δ=

1.38-1.50 (1H, m), 1.46 (3H, s), 1.86-2.04 (3H, m), 2.20-2.28 (1H, m), 2.74 (1H, dd, J=13.5, 9.6 Hz), 2.97 (1H, dd, J=13.5, 5.4 Hz), 4.27 (1H, d, J=5.9 Hz), 4.53 (1H, dd, J=5.9, 1.5 Hz), 7.16-7.36 (5H, m).

(Compound 5-4)

$^1$H-NMR ($CDCl_3$) δ=

1.39-1.50 (1H, m), 1.45 (3H, s), 1.85-2.10 (4H, m), 2.28-2.39 (1H, m), 2.87 (1H, dd, J=13.6, 8.2 Hz), 2.93 (1H, dd, J=13.6, 5.7 Hz), 4.27 (1H, d, J=5.9 Hz), 4.52 (1H, dd, J=5.9, 1.4 Hz), 6.95-7.10 (2H, m), 7.17-7.24 (2H, m).

(Compound 5-7)

$^1$H-NMR ($CDCl_3$) δ=

1.40-1.49 (1H, m), 1.46 (3H, s), 1.87-2.02 (3H, m), 2.17-2.26 (1H, m), 2.75 (1H, dd, J=13.7, 9.4 Hz), 2.96 (1H, dd, J=13.7, 5.5 Hz), 4.27 (1H, d, J=6.0 Hz), 4.53 (1H, dd, J=6.0, 1.5 Hz), 7.07-7.23 (4H, m).

(Compound 5-8)

$^1$H-NMR ($CDCl_3$) δ=

1.40-1.47 (1H, m), 1.45 (3H, s), 1.84-2.04 (3H, m), 2.20-2.24 (1H, m), 2.69 (1H, dd, J=13.6, 9.7 Hz), 2.93 (1H, dd, J=13.6, 5.3 Hz), 4.26 (1H, d, J=5.9 Hz), 4.52 (1H, dd, J=5.9, 1.5 Hz), 7.03-7.13 (4H, m).

(Compound 5-9)

$^1$H-NMR ($CDCl_3$) δ=

1.45 (3H, s), 1.48-1.53 (1H, m), 1.87-2.04 (3H, m), 2.25-2.33 (1H, m), 2.81-2.90 (2H, m), 4.27 (1H, d, J=5.9 Hz), 4.52 (1H, dd, J=5.9, 1.5 Hz), 6.76-6.83 (2H, m), 7.13-7.19 (1H, m).

(Compound 5-10)

$^1$H-NMR ($CDCl_3$) δ=

1.43-1.53 (1H, m), 1.47 (3H, s), 1.90-2.02 (3H, m), 2.18-2.26 (1H, m), 2.76 (1H, dd, J=13.9, 9.2 Hz), 2.95 (1H, dd, J=13.9, 5.9 Hz), 4.27 (1H, d, J=6.0 Hz), 4.54 (1H, dd, J=6.0, 1.5 Hz), 7.28 (1H, d, J=8.3 Hz), 7.51 (1H, dd, J=8.2, 2.5 Hz), 8.25 (1H, d, J=2.2 Hz).

(Compound 5-11)

$^1$H-NMR ($CDCl_3$) δ=

1.47 (3H, s), 1.47-1.52 (1H, m), 1.89-2.10 (3H, m), 2.20-2.27 (1H, m), 2.88 (1H, dd, J=14.7, 9.5 Hz), 3.07 (1H, dd, J=14.9, 5.8 Hz), 4.26 (1H, d, J=6.0 Hz), 4.52 (1H, dd, J=6.0, 1.5 Hz), 6.61 (1H, d, J=3.7 Hz), 6.73 (1H, d, J=3.7 Hz).

(Compound 5-12)

$^1$H-NMR ($CDCl_3$) δ=

1.48 (3H, s), 1.48-1.55 (1H, m), 1.92-2.08 (3H, m), 2.20-2.28 (1H, m), 2.92-3.00 (1H, m), 3.08-3.15 (1H, m), 4.26 (1H, d, J=6.0 Hz), 4.53 (1H, dd, J=6.0, 1.5 Hz), 7.30-7.34 (1H, s+s).

Production Example 17

Synthesis of (1RS,4SR,5RS)-4-(4-fluorobenzyl)-1-methyl-6-oxa-bicyclo[3,2,0]heptane-5-carboximide methyl ester (Compound 6a-2)

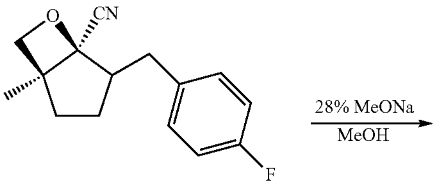

5-2

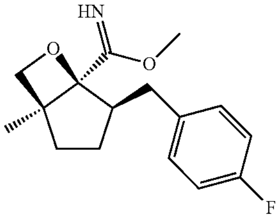

6a-2

First, Compound 5-2 was synthesized with use of Compound 2-2 as a starting material as in Production Example 16. Next, 481.4 mg of Compound 5-2 thus obtained was dissolved in 5 ml of anhydrous methanol. To the solution thus obtained, 0.454 ml of 28% solution of sodium methoxide/methanol was added. The resulting mixture was stirred at room temperature for 26 hours. After the reaction, an aqueous solution of 1 mol/l sulfuric acid was added to the reaction solution thus obtained to adjust the pH of the reaction solution to approximately 4. Thereafter, extraction with ethyl acetate was carried out. The organic layer thus extracted was washed with saturated brine and then dried over anhydrous sodium sulfate. The solvent was distilled away, and the residue was then purified by silica gel column chromatography to obtain 385 mg of Compound 6a-2.

The following shows the analysis result.

$^1$H-NMR ($CDCl_3$) δ=

1.10 (3H, s), 1.39-1.50 (1H, m), 1.80-2.01 (3H, m), 2.46-2.57 (3H, m), 3.63 (3H, s), 4.22 (1H, d, J=5.9 Hz), 4.27 (1H, dd, J=5.9, 1.5 Hz), 6.91 (2H, t, J=8.7 Hz), 7.05 (2H, d, J=8.7, 5.5 Hz), 7.94 (1H, brs).

In a similar method as in the present production example, compounds represented by Formula (6a) below were synthesized, wherein their respective combinations of $R^1$, $R^2$, and Ar were as listed in Table 3.

TABLE 3

(6a)

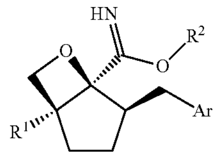

| Compound No. | $R^1$ | $R^2$ | Ar |
|---|---|---|---|
| 6a-1-1 | $CH_3$ | $CH_3$ | 4-ChloroPhenyl |
| 6a-1-2 | $CH_3$ | $CH_3CH_2$ | 4-ChloroPhenyl |
| 6a-3 | $CH_3$ | $CH_3$ | Phenyl |
| 6a-4 | $CH_3$ | $CH_3$ | 2-FluoroPhenyl |
| 6a-5 | $CH_3CH_2$ | $CH_3$ | 4-ChloroPhenyl |
| 6a-7 | $CH_3$ | $CH_3$ | 4-TrifluoromethoxyPhenyl |
| 6a-8 | $CH_3$ | $CH_3$ | 4-MethylPhenyl |
| 6a-9 | $CH_3$ | $CH_3$ | 2,4-Difluoro-Phenyl |
| 6a-10 | $CH_3$ | $CH_3$ | 5-ChloroPyridin-2-yl |
| 6a-11 | $CH_3$ | $CH_3$ | 5-ChloroThiophen-2-yl |
| 6a-12 | $CH_3$ | $CH_3$ | 2-ChloroThiazol-5-yl |

The following shows the respective analysis results of the compounds obtained above.

(Compound 6a-1-1)

$^1$H-NMR ($CDCl_3$) δ=

1.10 (3H, s), 1.39-1.48 (1H, m), 1.79-2.00 (3H, m), 2.44-2.58 (3H, m), 3.64 (3H, s), 4.22 (1H, d, J=5.9 Hz), 4.27 (1H, dd, J=5.9, 1.4 Hz), 7.04 (2H, d, J=8.5 Hz), 7.19 (2H, d, J=8.5 Hz), 7.96 (1H, brs).

(Compound 6a-1-2)

$^1$H-NMR ($CDCl_3$) δ=

1.12 (3H, s), 1.22 (3H, t, J=7.1 Hz), 1.39-1.48 (1H, m), 1.76-1.98 (3H, m), 2.46-2.57 (3H, m), 3.95-4.04 (1H, m), 4.10-4.19 (1H, m), 4.22 (1H, d, J=5.9 Hz), 4.27 (1H, dd, J=5.9, 1.1 Hz), 7.03 (2H, d, J=8.3 Hz), 7.19 (2H, d, J=8.3 Hz), 7.96 (1H, brs).

(Compound 6a-3)

$^1$H-NMR ($CDCl_3$) δ=

1.11 (3H, s), 1.39-1.47 (1H, m), 1.80 (1H, dd, J=5.5 Hz), 1.78-1.99 (2H, m), 2.48-2.60 (3H, m), 3.65 (3H, s), 4.23 (1H, d, J=5.9 Hz), 4.28 (1H, dd, J=5.9, 1.4 Hz), 7.19-7.26 (5H, m), 7.95 (1H, s).

(Compound 6a-4)

$^1$H-NMR ($CDCl_3$) δ=

1.10 (3H, s), 1.40-1.50 (1H, m), 1.78-1.84 (1H, m), 1.90-2.04 (2H, m), 2.56-2.73 (3H, m), 3.58 (3H, s), 4.23 (1H, d, J=5.9 Hz), 4.28 (1H, dd, J=5.9, 1.4 Hz), 6.92-7.02 (2H, m), 7.07-7.18 (2H, m), 7.93 (1H, brs).

(Compound 6a-5)

$^1$H-NMR ($CDCl_3$) δ=

0.72 (3H, t, J=7.5 Hz), 1.33-1.45 (2H, m), 1.57-1.65 (1H, m), 1.84-1.93 (3H, m), 2.44-2.57 (3H, m), 3.63 (3H, s), 4.22 (1H, d, J=5.9 Hz), 2.27 (1H, dd, J=5.9, 1.4 Hz), 7.01 (2H, d, J=8.0 Hz), 7.05 (2H, d, J=8.0 Hz), 7.9 (1H, brs).

(Compound 6a-7)

$^1$H-NMR ($CDCl_3$) δ=

1.10 (3H, s), 1.40-1.48 (1H, m), 1.79-1.84 (1H, m), 1.90-1.97 (2H, m), 2.45-2.53 (1H, m), 2.59 (2H, s), 3.61 (3H, s), 4.23 (1H, d, J=5.9 Hz), 4.28 (1H, dd, J=5.9, 1.4 Hz), 7.07-7.14 (4H, m), 7.97 (1H, brs).

(Compound 6a-8)

$^1$H-NMR ($CDCl_3$) δ=

1.11 (3H, s),1.41-1.46 (1H, m), 1.77-1.82 (1H, m), 1.88-1.95 (1H, m), 2.30 (3H. s), 2.48-2.55 (2H, m),3.67 (3H, s), 4.18 (1H, d, J=5.9 Hz), 4.34 (1H, dd, J=5.9, 1.5 Hz), 7.05 (2H, d, J=8.4 Hz), 7.20 (2H, d, J=8.4 Hz), 7.97 (1H, brs).

(Compound 6a-9)

$^1$H-NMR ($CDCl_3$) δ=

1.09 (3H, s), 1.41-1.49 (1H, m), 1.79-1.99 (3H, m), 2.51-2.66 (3H, m), 3.59 (3H, s), 4.23 (1H, d, J=5.9 Hz), 4.27 (1H, dd, J=5.9, 1.4 Hz), 6.69-6.76 (2H, m), 7.01-7.07 (1H, m), 7.93 (1H, brs).

(Compound 6a-10)

$^1$H-NMR ($CDCl_3$) δ=

1.11 (3H, s), 1.42-1.47 (1H, m), 1.70-1.86 (1H, m), 1.90-1.97 (2H, m), 2.46-2.65 (3H, m), 3.64 (3H, s), 4.23 (1H, d, J=5.9 Hz), 4.28 (1H, dd, J=5.9, 1.3 Hz), 7.19 (1H, d, J=8.1 Hz), 7.39 (1H, dd, J=8.14, 2.5 Hz), 7.96 (1H, s), 8.16 (1H, d, J=2.4 Hz).

(Compound 6a-11)

$^1$H-NMR ($CDCl_3$) δ=

1.12 (3H, s), 1.44-1.52 (1H, m), 1.81-1.97 (2H, m), 2.01-2.07 (1H, m), 2.46-2.54 (1H, m), 2.71 (2H, d, J=7.2 Hz), 3.72 (3H, s), 4.22 (1H, d, J=5.9 Hz), 4.27 (1H, dd, J=5.9, 1.4 Hz), 6.49 (1H, d, J=3.7 Hz), 6.67 (1H, d, J=3.7 Hz), 7.95 (s, 1H).

(Compound 6a-12)

$^1$H-NMR ($CDCl_3$) δ=

1.13 (3H, s), 1.45-1.51 (1H, m), 1.83-1.97 (2H, m), 2.00-2.06 (1H, m), 2.45-2.53 (1H, m), 2.74-2.80 (1H, m), 3.74 (3H, s), 4.22 (1H, d, J=6.0 Hz), 4.28 (1H, dd, J=6.0, 1.4 Hz), 7.19-7.22 (1H, s+s), 7.99 (1H, s).

Production Example 18

Synthesis of (1RS,4SR,5RS)-4-(4-chlorobenzyl)-1-methyl-6-oxa-bicyclo[3,2,0]heptane-5-carboxylic acid methyl ester (Compound 7a-1)

First, Compound 6a-1 was synthesized with use of Compound 5-1 as in Production Example 17.

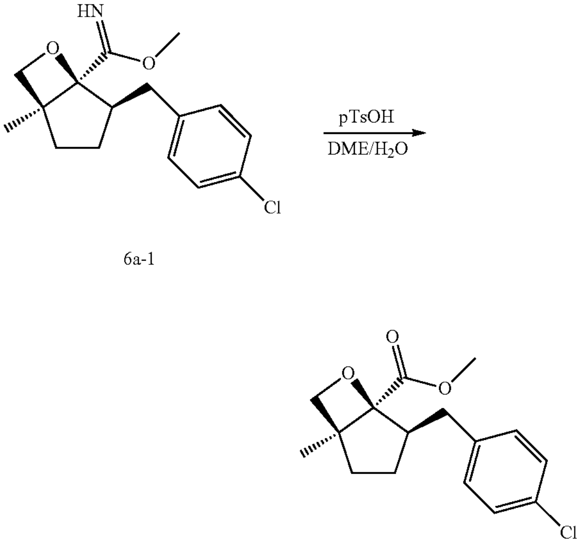

6a-1

7a-1

Next, 200 mg of Compound 6a-1 thus obtained was dissolved in 4 ml of dimethoxymethane. To the solution thus obtained, 0.8 ml of water and 130 mg of p-toluenesulfonic acid monohydrate was added. The resulting mixture was stirred at 80° C. for 45 minutes. After the reaction, water was added to the reaction solution thus obtained, and extraction with ethyl acetate was then carried out. Thereafter, the extract was washed with saturated brine. The organic layer thus extracted was dried over anhydrous sodium sulfate, and the solvent was then distilled away. The residue was purified by silica gel column chromatography to obtain 173.5 mg of Compound 7a-1.

The following shows the analysis result.

$^1$H-NMR ($CDCl_3$) δ=

1.14 (3H, s), 1.45-1.54 (1H, m), 1.79-1.85 (1H, m), 1.95-2.04 (2H, m), 2.58-2.72 (3H, m), 3.51 (3H, s), 4.27 (1H, d, J=5.8 Hz), 4.39 (1H, dd, J=5.8, 1.4 Hz), 7.07 (2H, d, J=8.4 Hz), 7.19 (2H, d, J=8.4 Hz).

Production Example 19

Synthesis of (1RS,4SR,5RS)-4-(4-chlorobenzyl)-1-methyl-6-oxa-bicyclo[3,2,0]hept-5-yl-methanol (Compound 8a-1)

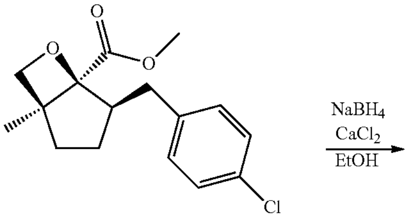

7a-1

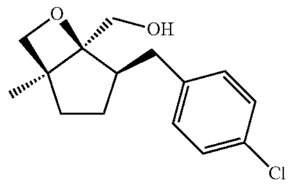

8a-1

In 20 ml of ethanol, 970.6 mg of Compound 7a-1 synthesized in Production Example 18 was dissolved. Thereafter, the solution thus obtained was cooled to 0° C. To the solution thus cooled, 249 mg of sodium borohydride and 365 mg of calcium chloride (powder) were added. The resulting mixture was stirred at 0° C. for 2 hours. After the reaction, the reaction was stopped with an aqueous solution of 1 mol/l citric acid. Then, extraction with ethyl acetate was carried out. The organic layer thus extracted was washed with an aqueous solution of sodium hydrogen carbonate and saturated brine and then dried over anhydrous sodium sulfate. The solvent was distilled away, and the residue was then purified by silica gel column chromatography to obtain 845.3 mg of Compound 8a-1.

The following shows the analysis result.

$^1$H-NMR ($CDCl_3$) δ=

1.23-1.31 (1H, m), 1.32 (3H, s), 1.62-1.94 (4H, m), 2.20 (1H, dd, J=9.1, 3.0 Hz), 2.58 (1H, dd, J=13.7, 9.3 Hz), 2.71 (1H, dd, J=13.7, 4.4 Hz), 3.57 (1H, dd, J=12.2, 9.1 Hz), 3.78 (1H, dd, J=12.2, 3.0 Hz), 4.23 (1H, d, J=5.9 Hz), 4.33 (1H, dd, J=5.9, 1.4 Hz), 7.10 (2H, d, J=8.5 Hz), 7.23 (2H, d, J=8.5 Hz).

Production Example 20

Synthesis of (1RS,4SR,5RS)-methanesulfonic acid 4-(4-chlorobenzyl)-1-methyl-6-oxa-bicyclo[3,2,0]hept-5-ylmethyl ester (Compound 9a-1-1)

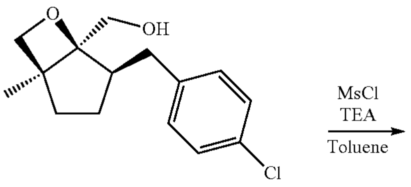

8a-1

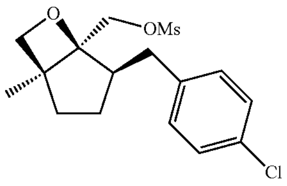

9a-1-1

In 6 ml of toluene, 300 mg of Compound 8a-1 synthesized in Production Example 19 was dissolved. To the solution thus obtained, 235 μl of triethylamine and 122 μl of methanesulfonyl chloride were added, and the resulting mixture was stirred at room temperature for 1 hour. After the reaction, water was added to the reaction solution thus obtained, and extraction with ethyl acetate was carried out. The organic layer thus extracted was washed with an aqueous solution of hydrochloric acid, an aqueous solution of sodium hydrogen carbonate, and saturated brine, and then dried over anhydrous sodium sulfate. The solvent was distilled away, and the residue was then purified by silica gel column chromatography to obtain 378.3 mg of Compound 9a-1-1.

The following shows the analysis result.

$^1$H-NMR ($CDCl_3$) δ=

1.29 (3H, s), 1.33 (1H, tdd, J=12.9, 6.7, 1.4 Hz), 1.74-1.82 (2H, m), 1.83-1.95 (1H, m), 2.00-2.09 (1H, m), 2.61 (1H, dd, J=13.6, 9.5 Hz), 2.77 (1H, dd, J=13.6, 5.2 Hz), 4.17 (1H, d, J=11.0 Hz), 4.20 (1H, d, J=5.9 Hz), 4.34 (1H, dd, J=5.9, 1.4 Hz), 4.43 (1H, d, J=1.0 Hz), 7.12 (2H, d, J=8.5 Hz), 7.24 (2H, d, J=8.5 Hz).

Production Example 21

Synthesis of toluene-4-sulfonic acid(1RS,4SR,5RS)-4-(4-chlorobenzyl)-1-methyl-6-oxa-bicyclo[3,2,0]hept-5-ylmethyl ester (Compound 9a-1-2)

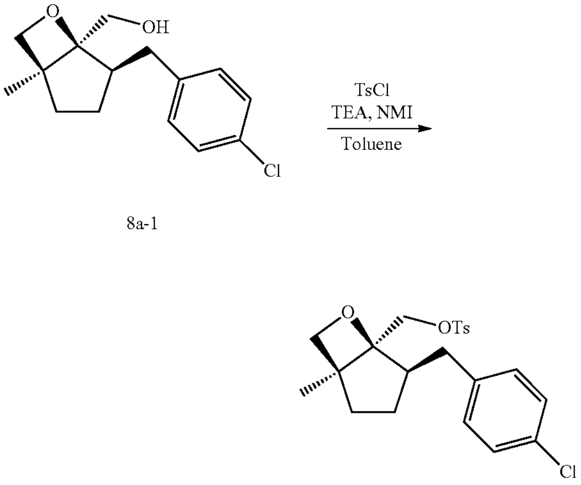

8a-1

9a-1-2

In 1 ml of toluene, 50 mg of Compound 8a-1 synthesized in Production Example 19 was dissolved. To the solution thus obtained, 39.5 μl of triethylamine, 22.2 μl of N-methylimidazole, and 53.6 mg of p-toluenesulfonyl chloride were added, and the resulting mixture was stirred at room temperature for 1.5 hours. After the reaction, water was added to the reaction solution thus obtained, and extraction with ethyl acetate was then carried out. The organic layer thus extracted was washed with an aqueous solution of hydrochloric acid, an aqueous solution of sodium hydrogen carbonate, and saturated brine, and then dried over anhydrous sodium sulfate. The solvent was distilled away, and the residue was then purified by silica gel column chromatography to obtain 77.0 mg of Compound 9a-1-2.

The following shows the analysis result.

$^1$H-NMR ($CDCl_3$) δ=

1.20 (3H, s), 1.27-1.36 (1H, m), 1.69-1.89 (3H, m), 2.03-2.12 (1H, m), 2.46 (3H, s), 2.48 (1H, dd, J=13.6, 9.3 Hz), 2.55 (1H, dd, J=13.6, 5.6 Hz), 3.89 (1H, d, J=10.4 Hz), 4.13 (1H, d, J=5.9 Hz), 4.22 (1H, d, J=10.4 Hz), 4.25 (1H, dd, J=5.9, 1.4 Hz), 7.01 (2H, d, J=8.4 Hz), 7.17 (2H, d, J=8.4 Hz), 7.35 (2H, d, J=8.0 Hz), 7.77 (2H, d, J=8.0 Hz).

Production Example 22

Synthesis of (1RS,4SR,5RS)-1-[4-(4-chlorobenzyl)-1-methyl-6-oxa-bicyclo[3,2,0]hept-5-ylmethyl-1H-[1,2,4]]-triazole (Compound 10a-1)

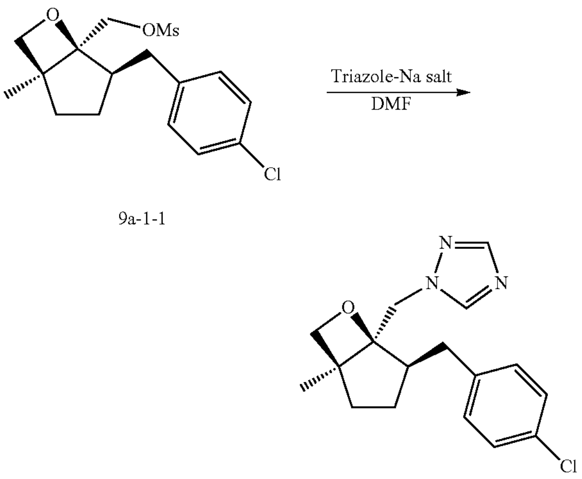

9a-1-1

10a-1

Compound 9a-1-1 (47.1 mg) synthesized in Production Example 20 was dissolved in 1.5 ml of dimethylformamide. To the solution thus obtained, 14.9 mg of triazole sodium salt was added, and the resulting mixture solution was stirred at 60° C. for 45 minutes. The reaction temperature was raised to 80° C., so that the reaction solution was further stirred at 80° C. for 45 minutes. Thereafter, to the reaction solution thus obtained, 10.0 mg of triazole sodium salt was added. After the resulting mixture solution was stirred at the same temperature for 45 minutes, the reaction temperature was raised to 100° C., so that the reaction solution was further stirred at 100° C. for 3 hours. The reaction temperature was further raised to 120° C., so that the reaction solution was stirred at 120° C. for 6 hours. To the reaction solution thus obtained, 12.5 mg of triazole sodium salt was added. The mixture solution thus obtained was further stirred at the same temperature for 9.5 hours. After the reaction, the solvent was distilled away from the reaction solution thus obtained, and the residue was then mixed with water. Thereafter, extraction with ethyl acetate was carried out. The organic layer thus extracted was washed with water and saturated brine and then dried over anhydrous sodium sulfate. The solvent was distilled away, and the residue was then purified by silica gel column chromatography to obtain 35.4 mg of Compound 10a-1.

The following shows the analysis result.

$^1$H-NMR ($CDCl_3$) δ=

1.21 (3H, s), 1.24-1.34 (1H, m), 1.68-1.79 (2H, m), 1.80-1.87 (2H, m), 2.31 (1H, dd, J=13.5, 4.0 Hz), 2.39 (1H, dd, J=13.5, 9.3 Hz), 4.22 (1H, s), 4.42 (1H, d, J=15.0 Hz), 4.48 (1H, d, J=15.0 Hz), 7.50 (2H, d, J=8.4 Hz), 7.22 (1H, d, J=8.4 Hz), 7.95 (1H, s), 8.15 (1H, s).

Production Example 23

Synthesis of (1RS,4SR,5RS)-1-[4-(4-fluorobenzyl)-1-methyl-6-oxa-bicyclo[3,2,0]hept-5-ylmethyl-1H-[1,2,4]]-triazole (Compound 10a-2)

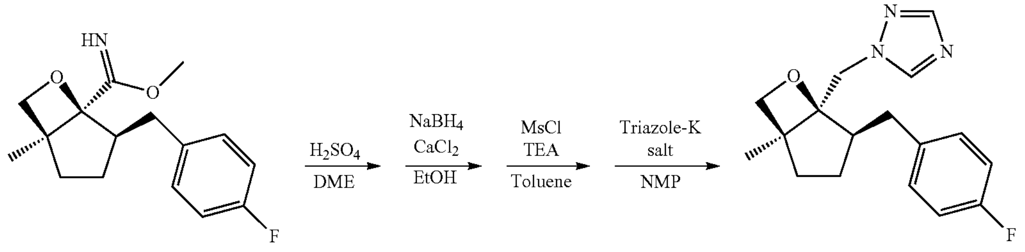

6a-2 10a-2

In 145 ml of dimethoxymethane, 14.351 g of Compound 6a-2 obtained in Production Example 17 was dissolved. To the solution thus obtained, 47.3 ml of aqueous solution of 1 mol/l sulfuric acid was added. The resulting mixture was subjected to stirring at room temperature for 25 hours and then subjected to further stirring at 40° C. for 4 hours. After the reaction, the reaction solution thus obtained was concentrated. To the solution thus concentrated, water was added, and extraction with toluene was carried out. The organic layer thus extracted was washed with a saturated aqueous solution of sodium carbonate and saturated brine. The organic layer thus extracted was dried with anhydrous sodium sulfate.

The organic layer thus dried was dissolved in 141 ml of ethanol, and the solution thus obtained was cooled to 0° C. To the solution thus cooled, 5.25 g of calcium chloride and 3.58 g of sodium borohydride were added. While the reaction temperature was raised to room temperature, the resulting mixture thus obtained was stirred for 3.5 hours. After the reaction, the reaction solution thus obtained was subjected to cooling with water. While being stirred, an aqueous solution of 10% citric acid was added to the solution thus cooled to stop the reaction. The organic solvent was removed from the reaction solution, and extraction with toluene was then carried out. The organic layer thus extracted was washed with an aqueous solution of sodium hydrogen carbonate and saturated brine, and then dried over anhydrous sodium sulfate. Thereafter, the solvent was distilled away.

The residue was dissolved in 60 ml of toluene, and 9.84 ml of triethylamine was added to the solution thus obtained. While the temperature of the resulting mixture solution was controlled to be 25° C. or lower, a solution obtained by dissolving 5.13 ml of methanesulfonyl chloride in 12 ml of toluene was allowed to drip onto the mixture solution. Thereafter, the resulting mixture solution was stirred at room temperature for 80 minutes. After the reaction, 50 ml of water was added to the reaction solution thus obtained, and extraction with toluene was then carried out. The organic layer thus extracted was washed with an aqueous solution of sodium hydrogen carbonate and saturated brine, and then dried over anhydrous sodium sulfate. Thereafter, the solvent was distilled away.

The residue was dissolved in 83 ml of NMP, and 10.14 g of triazole potassium salt was added to the solution thus obtained. The resulting mixture was stirred at 120° C. for 2. hours. After the reaction, water was added to the reaction solution thus obtained, and extraction with toluene was then carried out. The organic layer thus extracted was washed with water and saturated brine and then dried over anhydrous sodium sulfate. The solvent was distilled away, and the residue was then purified by silica gel column chromatography to obtain 10.98 g of Compound 10a-2.

The following shows the analysis result.

$^1$H-NMR ($CDCl_3$) δ=

1.20 (3H, s), 1.23-1.35 (1H, m), 1.61-1.80 (2H, m), 1.82-1.90 (2H, m), 2.31 (1H, dd, J=13.5, 4.0 Hz), 2.50 (1H, dd, J=13.5, 9.2 Hz), 4.21 (1H, d, J=7.9 Hz), 4.23 (1H, d, J=7.9 Hz), 4.42 (1H, d, J=14.9 Hz), 4.47 (1H, d, J=14.9 Hz), 6.94 (2H, t, J=8.8 Hz), 7.07 (1H, dd, J=8.8, 5.5 Hz), 7.95 (1H, s), 8.14 (1H, s).

In a similar method as in the present production example, compounds represented by Formula (10a) below were synthesized, wherein their respective combinations of $R^1$, A, and Ar were as listed in Table 4.

TABLE 4

(10a)

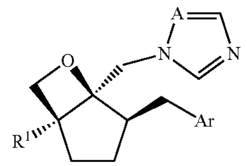

| Compound No. | $R^1$ | A | Ar |
|---|---|---|---|
| 10a-3 | $CH_3$ | N | Phenyl |
| 10a-4 | $CH_3$ | N | 2-FluoroPhenyl |
| 10a-5 | $CH_3CH_2$ | N | 4-ChloroPhenyl |
| 10a-7 | $CH_3$ | N | 4-TrifluoromethoxyPhenyl |
| 10a-8 | $CH_3$ | N | 4-MethylPhenyl |
| 10a-9 | $CH_3$ | N | 2,4-Difluoro-Phenyl |
| 10a-10 | $CH_3$ | N | 5-ChloroPyridin-2-yl |
| 10a-11 | $CH_3$ | N | 5-ChloroThiophen-2-yl |
| 10a-12 | $CH_3$ | N | 2-ChloroThiazol-2-yl |
| 10a-38 | $CH_3$ | CH | 4-ChloroPhenyl |

The following shows the respective analysis results of the compounds obtained above.

(Compound 10a-3)

$^1$H-NMR ($CDCl_3$) δ=

1.20 (3H, s), 1.30-1.33 (1H, m), 1.69-1.91 (4H, m), 2.45 (1H, dd, J=13.4, 4.7 Hz), 2.56 (1H, dd, J=13.4, 8.5 Hz), 4.20 (1H, dd, J=6.0, 1.3 Hz), 4.23 (1H, d, J=6.0 Hz), 4.37 (1H, d, J=14.9 Hz), 4.45 (1H, d, J=14.9 Hz), 7.12-7.25 (3H, m), 7.27 (2H, d, J=7.0 Hz), 7.93 (1H, s), 8.02 (1H, s).

(Compound 10a-4)

$^1$H-NMR ($CDCl_3$) δ=

1.18 (3H, s), 1.28-1.37 (1H, m), 1.67-1.77 (2H, m), 1.83-1.96 (2H, m), 2.47 (1H, dd, J=13.6, 3.9 Hz), 2.65 (1H, dd,

J=13.6, 8.7 Hz), 4.19 (1H, dd, J=6.0, 1.3 Hz), 4.23 (1H, d, J=6.0 Hz), 4.40 (1H, d, J=15.0 Hz), 4.49 (1H, d, J=15.0 Hz), 6.95-7.02 (1H, m), 7.02-7.07 (1H, m), 7.14-7.21 (2H, m), 7.94 (1H, s), 8.14 (1H, s).

(Compound 10a-5)

$^1$H-NMR ($CDCl_3$) δ=

0.77 (3H, t, J=7.4 Hz), 1.19-1.28 (1H, m), 1.47-1.58 (1H, m), 1.68-1.87 (5H, m), 2.27 (1H, dd, J=13.4, 3.6 Hz), 2.47 (1H, dd, J=13.4, 9.3 Hz), 4.20 (1H, d, J=6.1 Hz), 4.30 (1H, dd, J=6.1, 1.4 Hz), 4.45 (1H, d, J=14.9 Hz), 4.49 (1H, d, J=14.9 Hz), 7.04 (1H, d, J=8.4 Hz), 7.22 (1H, d, J=8.4 Hz), 7.95 (1H, s), 8.15 (1H, s).

(Compound 10a-7)

$^1$H-NMR ($CDCl_3$) δ=

1.22 (3H, s), 1.24-1.34 (1H, m), 1.69-1.75 (2H, m), 1.79-1.87 (2H, m), 2.32 (1H, dd, J=13.6, 3.8 Hz), 2.52 (1H, dd, J=13.5, 9.6 Hz), 4.24 (2H, s), 4.45 (1H, d, J=14.9 Hz), 4.50 (1H, d, J=14.9 Hz), 7.09-7.15 (4H, m), 7.95 (1H, s), 8.16 (1H, s).

(Compound 10a-8)

$^1$H-NMR ($CDCl_3$) δ=

1.19 (3H, s), 1.26-1.34 (1H, m), 1.69-1.90 (4H, m), 2.31 (3H, s), 2.42 (1H, dd, J=13.5, 4.6 Hz), 2.53 (1H, dd, J=13.5, 8.5 Hz), 4.18 (1H, dd, J=6.0, 1.3 Hz), 4.22 (1H, d, J=6.0 Hz), 4.36 (1H, d, J=15.0 Hz), 7.01 (2H, d, J=7.9 Hz), 7.07 (2H, d, J=7.9 Hz), 7.92 (1H, s), 8.02 (1H, s).

(Compound 10a-9)

$^1$H-NMR ($CDCl_3$) δ=

1.19 (3H, s), 1.24-1.33 (1H, m), 1.67-1.74 (2H, m), 1.86-1.88 (2H, m), 2.35 (1H, d, J=13.3 Hz), 2.60 (1H, dd, J=13.5, 8.9 Hz), 4.21 (1H, dd, J=6.0, 1.2 Hz), 4.23 (1H, d, J=6.0 Hz), 4.45 (1H, d, J=15.0 Hz), 4.50 (1H, d, J=15.0 Hz), 6.72-6.80 (2H, m), 7.08-7.14 (1H, m), 7.95 (1H, s), 8.22 (1H, s).

(Compound 10a-10)

$^1$H-NMR ($CDCl_3$) δ=

1.24 (3H, s), 1.24-1.34 (1H, m), 1.65-1.91 (4H, m), 2.19 (1H, dd, J=13.6, 3.6 Hz), 2.48 (1H, dd, J=13.6, 10.2 Hz), 4.24 (1H, d, J=6.1 Hz), 4.28 (1H, dd, J=6.1, 1.2 Hz), 4.54 (2H, s), 7.22 (1H, d, J=8.1 Hz), 7.41 (1H, dd, J=8.2, 2.5 Hz), 7.97 (1H, s), 8.18 (1H, d, J=2.4 Hz), 8.24 (1H, s).

(Compound 10a-11)

$^1$H-NMR ($CDCl_3$) δ=

1.19 (3H, s), 1.31-1.39 (1H, m), 1.75 (1H, dd, J=13.2, 5.4 Hz), 1.82-1.95 (3H, m), 2.40 (1H, dd, J=14.9, 3.5 Hz), 2.67 (1H, dd, J=14.8, 8.6 Hz), 4.21 (2H, s), 4.45 (2H, s), 6.51 (1H, d, J=3.7 Hz), 6.69 (1H, d, J=3.7 Hz), 7.95 (1H, s), 8.20 (1H, s).

(Compound 10a-12)

$^1$H-NMR ($CDCl_3$) δ=

1.23 (3H, s), 1.33-1.39 (1H, m), 1.76-1.92 (4H, m), 2.26-2.32 (m, 1H), 2.66-2.75 (1H, m), 4.23 (1H, d, J=6.2 Hz), 4.26 (1H, dd, J=6.1, 1.1 Hz), 4.48 (1H, d, J=15.0 Hz), 4.53 (1H, d, J=14.9 Hz), 7.20-7.23 (1H, s+s), 7.96 (1H, s), 8.23 (1H, s).

(Compound 10a-38)

$^1$H-NMR ($CDCl_3$) δ=

1.12 (3H, s), 1.22-1.34 (1H, m), 1.67-1.78 (2H, m), 1.78-1.90 (2H, m), 1.97-2.06 (1H, m), 2.15 (1H, dd, J=13.7, 3.9 Hz), 2.51 (1H, dd, J=13.7, 9.7 Hz), 4.15 (1H, d, J=15.1 Hz), 4.20 (1H, d, J=6.0 Hz), 4.22 (1H, dd, J=15.1 Hz), 4.22 (1H, dd, J=6.0, 1.2 Hz), 7.02 (2H, d, J=8.4 Hz), 7.09 (2H, d, J=1.0 Hz), 7.21 (2H, d, J=8.4 Hz), 7.59 (1H, s).

Production Example 24

Synthesis of (1RS,2SR,5SR)-5-(4-chlorobenzyl)-2-chloromethyl-2-methyl-1-(1H-1,2,4-triazole)-1-ylmethylcyclopentanol (Compound 11a-1)

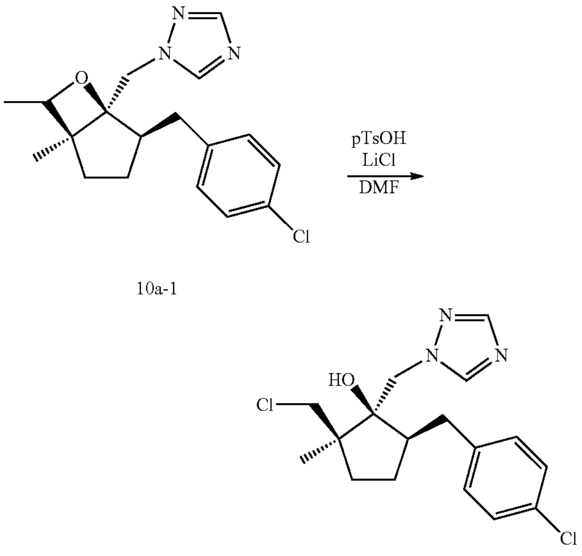

10a-1

11a-1

In 200 ml of dimethylformamide, 20.79 g of Compound 10a-1 obtained in Production Example 22 was dissolved, and the solution thus obtained was heated to 80° C. To the solution thus heated, 39.59 g of lithium chloride and 14.20 g of p-toluenesulfonic acid monohydrate were added, and the resulting mixture was stirred for 1.5 hours. After the reaction, the DMF was distilled away under a reduced pressure, the residue was mixed with water, and extraction with ethyl acetate was then carried out. The organic layer thus extracted was washed with water and saturated brine and then dried over anhydrous sodium sulfate. The solvent was distilled away, and the residue was then recrystallized to obtain 22.24 g of Compound 11a-1.

The following shows the respective analysis results of the compounds obtained above.

$^1$H-NMR (400 MHz, $CDCl_3$) δ:

1.18 (3H, s), 1.46 (2H, m), 1.70 (1H, m), 1.92 (2H, m), 2.35 (2H, m), 3.26 (1H, d, J=10.8 Hz), 3.57 (1H, d, J=10.8 Hz), 4.06 (1H, s), 4.25 (1H, d, J=14.2 Hz), 4.54 (1H, d, J=14.2 Hz), 6.98 (2H, d, J=8.4 Hz), 7.21 (2H, d, J=8.4 Hz), 8.02 (1H, s), 8.19 (1H, s).

In a similar method as in the present production example, compounds represented by Formula (11a) below were synthesized, wherein their respective combinations of $R^1$, $X^4$, A, and Ar were as listed in Table 5.

TABLE 5

(11a)

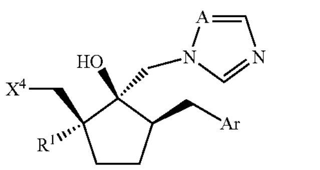

| Compound No. | $R^1$ | A | Ar | $X^4$ |
|---|---|---|---|---|
| 11a-2 | $CH_3$ | N | 4-FluoroPhenyl | Cl |
| 11a-3 | $CH_3$ | N | Phenyl | Cl |
| 11a-4 | $CH_3$ | N | 2-FluoroPhenyl | Cl |
| 11a-5 | $CH_3CH_2$ | N | 4-ChloroPhenyl | Cl |
| 11a-7 | $CH_3$ | N | 4-TrifluoromethoxyPhenyl | Cl |
| 11a-8 | $CH_3$ | N | 4-MethylPhenyl | Cl |
| 11a-9 | $CH_3$ | N | 2,4-Difluoro-Phenyl | Cl |
| 11a-10 | $CH_3$ | N | 5-ChloroPyridin-2-yl | Cl |
| 11a-11 | $CH_3$ | N | 5-ChloroThiophen-2-yl | Cl |
| 11a-12 | $CH_3$ | N | 2-ChloroThiazol-2-yl | Cl |
| 11a-31 | $CH_3$ | N | 4-FluoroPhenyl | Br |
| 11a-32 | $CH_3$ | N | Phenyl | Br |
| 11a-33 | $CH_3$ | N | 5-ChloroPyridin-2-yl | Br |
| 11a-34 | $CH_3$ | N | 5-ChloroThiophen-2-yl | Br |
| 11a-38 | $CH_3$ | CH | 4-ChloroPhenyl | Cl |

The following shows the respective analysis results of the compounds obtained above.

(Compound 11a-2)

$^1$H-NMR ($CDCl_3$) δ=

1.18 (3H, s), 1.41-1.53 (2H, m), 1.65-1.76 (1H, m), 1.89-1.98 (2H, m), 2.28-2.38 (2H, m), 3.26 (1H, d, J=10.8 Hz), 3.57 (1H, d, J=10.8 Hz), 4.05 (1H, s), 4.25 (1H, d, J=14.2 Hz), 4.54 (1H, d, J=14.2 Hz), 6.92 (2H, t, J=8.7 Hz), 7.00 (2H, dd, J=8.7, 5.5 Hz), 8.01 (1H, s), 8.19 (1H, s).

(Compound 11a-3)

$^1$H-NMR ($CDCl_3$) δ=

1.18 (3H, s), 1.40-1.56 (2H, m), 1.67-1.77 (1H, m), 1.91-2.04 (2H, m), 2.34-2.43 (2H, m), 3.22 (1H, d, J=10.8 Hz), 3.57 (1H, d, J=10.8 Hz), 4.02 (1H, s), 4.25 (1H, d, J=14.2 Hz), 4.53 (1H, d, J=14.2 Hz), 7.05 (2H, d, J=7.3 Hz), 7.16 (1H, t, J=7.3 Hz), 7.23 (2H, d, J=7.3 Hz), 8.01 (1H, s), 8.19 (1H, s).

(Compound 11a-4)

$^1$H-NMR ($CDCl_3$) δ=

1.18 (3H, s), 1.41-1.57 (2H, m), 1.63-1.74 (1H, m), 1.91-2.10 (2H, m), 2.36-2.47 (2H, m), 3.22 (1H, d, J=10.8 Hz), 3.59 (1H, d, J=10.8 Hz), 4.29 (1H, d, J=14.2 Hz), 4.30 (1H, s), 4.56 (1H, d, J=14.2 Hz), 6.94-6.99 (1H, m), 7.01 (1H, td, J=7.5, 1.2 Hz), 7.09 (1H, td, J=7.5, 1.8 Hz), 7.12-7.19 (1H, m), 8.01 (1H, s), 8.20 (1H, s).

(Compound 11a-5)

$^1$H-NMR ($CDCl_3$) δ=

0.94 (3Ht, J=7.3 Hz), 1.31-1.46 (2H, m), 1.49 (1H, dd, J=13.0, 3.2 Hz), 1.50-1.63 (3H, m), 1.79-1.80 (1H, m), 2.13 (1H, dd, J=13.0, 11.5 Hz), 2.23-2.31 (1H, m), 3.50 (1H, d, J=11.4 Hz), 4.03 (1H, s), 4.34 (1H, d, J=14.2 Hz), 4.79 (1H, d, J=14.2 Hz), 6.88 (2H, d, J=8.4 Hz), 7.17 (2H, d, J=8.4 Hz), 8.01 (1H, s), 8.21 (1H, s).

(Compound 11a-7)

$^1$H-NMR ($CDCl_3$) δ=

1.19 (3H, s), 1.41-1.52 (2H, m), 1.66-1.76 (1H, m), 1.91-1.99 (2H, m), 2.30-2.41 (2H, m), 3.29 (1H, d, J=10.8 Hz), 3.58 (1H, d, J=10.8 Hz), 4.07 (1H, s), 4.27 (1H, d, J=14.2 Hz), 4.56 (1H, d, J=14.2 Hz), 7.04-7.10 (4H, m), 8.02 (1H, s), 8.20 (1H, s).

(Compound 11a-8)

$^1$H-NMR ($CDCl_3$) δ=

1.18 (3H, s), 1.41-1.52 (2H, m), 1.71-1.76 (1H, m), 1.90-2.02 (2H, m), 2.29 (3H, s), 2.31-2.37 (2H, m), 3.20 (1H, d, J=10.8 Hz), 3.57 (1H, d, J=10.8 Hz), 3.97 (3H, s), 4.24 (1H, d, J=14.2 Hz), 4.51 (1H, d, J=14.2 Hz), 6.95 (2H, d, J=7.9 Hz), 7.05 (2H, d, J=7.9 Hz), 8.00 (1H, s), 8.18 (1H, s).

(Compound 11a-9)

$^1$H-NMR ($CDCl_3$) δ=

1.18 (3H, s), 1.41-1.47 (2H, m), 1.63-1.69 (1H, m), 1.91-1.99 (2H, m), 2.36-2.39 (2H, m), 3.26 (1H, d, J=10.8 Hz), 3.58 (1H, d, J=10.8 Hz), 4.29 (1H, d, J=14.2 Hz), 4.34 (1H, s), 4.57 (1H, d, J=14.2 Hz), 6.70-6.78 (2H, m), 7.01-7.07 (1H, m), 8.02 (1H, s), 8.20 (1H, s).

(Compound 11a-10)

$^1$H-NMR ($CDCl_3$) δ=

1.19 (s, 3H), 1.40-1.49 (m, 2H), 1.65-1.75 (m, 1H), 1.87-1.99 (m, 2H), 2.31-2.41 (m, 2H), 3.31 (d, 1H, J=10.9 Hz), 3.57 (d, 1H, J=10.8 Hz), 4.16 (s, 1H), 4.28 (d, 1H, J=14.2 Hz), 4.58 (d, 1H, J=14.2 Hz), 7.21 (d, 1H, J=8.2 Hz), 7.34 (dd, 1H, J=8.2, 2.5 Hz), 8.03 (s, 1H), 8.11 (d, 1H, J=2.4 Hz), 8.20 (s, 1H).

(Compound 11a-11)

$^1$H-NMR ($CDCl_3$) δ=

1.19 (s, 3H), 1.44-1.53 (m, 2H), 1.89-1.97 (m, 2H), 2.02 (dd, 1H, J=15.1, 3.6 Hz), 2.29-2.34 (m, 1H), 2.55 (dd, 1H, J=14.6, 10.3 Hz), 3.22 (d, 1H, J=10.8 Hz), 3.55 (d, 1H, J=10.8 Hz), 4.17 (s, 1H), 4.23 (d, 1H, J=14.2 Hz), 4.54 (d, 1H, J=14.2 Hz), 6.45 (d, 1H, J=3.7 Hz), 6.66 (d, 1H, J=3.7 Hz), 8.02 (s, 1H), 8.16 (s, 1H).

(Compound 11a-12)

$^1$H-NMR ($CDCl_3$) δ=

1.19 (s, 3H), 1.43-1.53 (m, 2H), 1.86-2.00 (m, 3H), 2.31-2.36 (m, 1H), 2.56-2.65 (m, 1H), 3.29 (d, 1H, J=10.8 Hz), 3.55 (d, 1H, J=10.9 Hz), 4.26 (s, 1H), 4.27 (d, 1H, J=14.2 Hz), 4.58 (d, 1H, J=14.2 Hz), 7.14-7.17 (s+s, 1H), 8.03 (s, 1H), 8.18 (s, 1H).

(Compound 11a-31)

$^1$H-NMR ($CDCl_3$) δ=

1.20 (3H, s), 1.42-1.53 (2H, m), 1.65-1.76 (1H, m), 1.91-1.99 (2H, m), 2.30-2.42 (2H, m), 2.95 (1H, d, J=9.9 Hz), 3.54 (1H, d, J=9.9 Hz), 4.08 (1H, s), 4.23 (1H, d, J=14.2 Hz), 4.51 (1H, d, J=14.2 Hz), 6.93 (2H, t, J=8.7 Hz), 7.01 (2H, dd, J=8.7, 5.4 Hz), 8.02 (1H, s), 8.18 (1H, s).

(Compound 11a-32)

$^1$H-NMR ($CDCl_3$) δ=

1.20 (3H, s), 1.45-1.58 (2H, m), 1.67-1.78 (1H, m), 1.93-2.01 (1H, m), 2.03-2.17 (1H, m), 2.35-2.46 (2H, m), 2.92 (1H, d, J=9.9 Hz), 3.54 (1H, d, J=9.9 Hz), 4.05 (1H, s), 4.24 (1H, d, J=14.2 Hz), 4.50 (1H, d, J=14.2 Hz), 7.07 (2H, d, J=7.3 Hz), 7.15 (1H, t, J=7.3 Hz), 7.24 (2H, d, J=7.3 Hz), 8.01 (1H, s), 8.18 (1H, s).

(Compound 11a-33)

$^1$H-NMR ($CDCl_3$) δ=

1.20 (s, 3H), 1.39-1.54 (m, 2H), 1.64-1.74 (m, 1H), 1.95-2.02 (m, 2H), 2.33-2.45 (m, 2H), 3.00 (d, 1H, J=10.0 Hz), 3.54 (d, 1H, J=10.0 Hz), 4.23 (s, 1H), 4.27 (d, 1H, J=14.2 Hz), 4.56 (d, 1H, J=14.2 Hz), 7.22 (d, 1H, J=7.6 Hz), 7.35 (dd, 1H, J=8.2, 2.5 Hz), 8.03 (s, 1H), 8.12 (d, 1H, J=2.3 Hz), 8.20 (s, 1H).

(Compound 11a-34)

$^1$H-NMR ($CDCl_3$) δ=

1.20 (s, 3H), 1.45-1.57 (m, 2H), 1.86-2.02 (m, 2H), 2.13 (dd, 1H, J=15.1, 3.8 Hz), 2.34-2.39 (m, 1H), 2.59 (dd, 1H, J=14.7, 10.2 Hz), 2.91 (d, 1H, J=9.9 Hz), 3.52 (d, 1H, J=9.8

Hz), 4.23 (s, 1H), 4.23 (d, 1H, J=14.2 Hz), 6.52 (d, 1H, J=14.2 Hz), 6.47 (d, 1H, J=3.6 Hz), 6.67 (d, 1H, J=3.6 Hz), 8.02 (s, 1H), 8.16 (s, 1H).

(Compound 11a-38)

$^1$H-NMR ($CDCl_3$) δ=

1.20 (3H, s), 1.39-1.53 (2H, m), 1.70-1.81 (1H, m), 1.85-1.93 (1H, m), 1.93 (1H, dd, J=13.1, 3.3 Hz), 2.26 (1H, dd, J=13.1, 11.2 Hz), 2.34-2.42 (2H, m), 3.39 (1H, d, J=11.0 Hz), 3.57 (1H, d, J=11.0 Hz), 4.07 (1H, d, J=14.5 Hz), 4.31 (1H, d, J=14.5 Hz), 6.98 (2H, d, J=8.3 Hz), 7.08-7.11 (2H, m), 7.21 (2H, d, J=8.3 Hz), 7.64 (1H, s).

Example 2

Production Example 25

Synthesis of (1RS,5RS)-4-(4-chlorobenzyl)-1-methyl-6-oxa-bicyclo[3,2,0]heptane-5-carboxyamide (Compound 12-1)

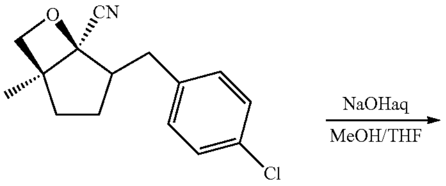

5-1

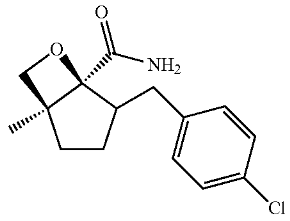

12-1

In 7 ml of tetrahydrofuran, 703 mg of Compound 5-1 obtained in Production Example 9 of Example 1 was dissolved. To the solution thus obtained, 7 ml of methanol and 5 ml of 25% aqueous solution of sodium hydride were added, and the resulting mixture was refluxed in hot water bath of 80° C. for 5 hours. After the reaction, the solvent was distilled away, and the residue was then mixed with water.

The crystal precipitated out of the solution was recovered by filtration, washed with water, and then dried under a reduced pressure to obtain 699.7 mg of Compound 12-1.

The following shows the analysis result.

(1,5-cis Form)

$^1$H-NMR ($CDCl_3$) δ=

1.23 (3H, s), 1.42-1.51 (1H, m), 1.72-1.82 (1H, m), 1.86-1.95 (2H, m), 2.55-2.76 (3H, m), 4.31 (1H, d, J=8.2 Hz), 4.32 (1H, d, J=8.2 Hz), 5.47 (1H, brs), 6.82 (1H, brs), 7.10 (2H, d, J=8.5 Hz), 7.20 (2H, d, J=8.5 Hz).

(1,5-trans form)

$^1$H-NMR ($CDCl_3$) δ=

1.31 (3H, s), 1.67-1.86 (3H, m), 2.15-2.25 (1H, m), 2.40-2.48 (2H, m), 2.81-2.91 (1H, m), 4.22 (1H, d, J=5.8 Hz), 4.28 (1H, d, J=5.8 Hz), 5.57 (brs, 1H), 6.89 (brs, 1H), 7.07 (1H, d, J=8.3 Hz), 7.23 (1H, d, J=8.3 Hz).

Production Example 26

(1RS,5RS)-4-(4-chlorobenzyl)-1-methyl-6-oxa-bicyclo[3,2,0]heptane-5-carboxylic acid (Compound 13-1)

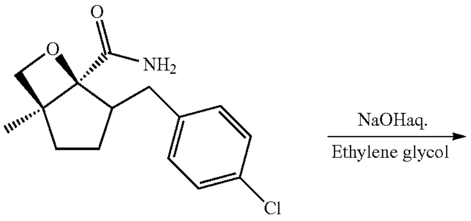

12-1

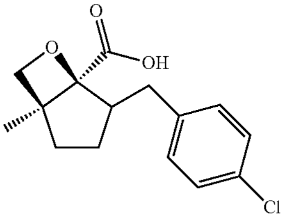

13-1

In 30 ml of ethylene glycol, 3.00 g of Compound 12-1 synthesized in Production Example 25 was dissolved by heating at 70° C. To the solution thus obtained, 8.58 g of 50% (w/w) aqueous solution of sodium hydride was added, and the resulting mixture solution was then stirred for 13 hours while being heated at an internal temperature of 117° C. After the reaction, the reaction solution thus obtained was cooled to around room temperature while being stirred. After the cooling, the solution thus cooled was mixed with ice water and toluene and then subjected to suction filtration for recovery of a hardly soluble product. The product thus recovered was washed with a small amount of water and toluene to obtain 1.393 g of white solid. After the white solid was stirred in a mixture solution of 1M sulfuric acid and ethyl acetate, the ethyl acetate layer was extracted from the mixture solution and then dried to obtain white solid. Further, an aqueous layer obtained from the filtrate was neutralized with 1M sulfuric acid to pH 5 and then extracted with ethyl acetate. The organic layer was washed with water and saturated brine and then dried over anhydrous sodium sulfate. The solvent was distilled away, and the residue was mixed with the previously obtained white solid. the mixture was recrystallized. As a result, 1.612 g of Compound 13-1 was obtained.

The following shows the analysis result.

(1,5-cis Form)

$^1$H-NMR ($CDCl_3$)=

1.25 (s, 3H), 1.47-1.55 (m, 1H), 1.82-1.90 (m, 1H), 1.93-1.99 (m, 2H), 2.63-2.69 (m, 3H), 4.38 (d, 1H, J=6.2 Hz), 4.42 (dd, 1H, J=6.2, 1.3 Hz), 7.08 (dd, 2H, J=6.5, 1.9 Hz), 7.21 (dd, 2H, J=6.5, 2.0 Hz).

(1,5-trans Form)

$^1$H-NMR ($CDCl_3$)=

1.33 (3H, s), 1.70-1.80 (2H, m), 1.84-1.92 (1H, m), 2.17-2.30 (2H, m), 2.39 (1H, dd, J=13.9, 12.3 Hz), 2.47-2.54 (1H, m), 2.84 (1H, dd, J=13.9, 4.2 Hz), 4.30 (1H, d, J=6.2 Hz), 4.34 (1H, dd, J=6.2, 1.1 Hz), 7.05 (2H, d, J=8.3 Hz), 7.25 (2H, dd, J=8.3 Hz).

Production Example 27

Synthesis of (1RS,5RS)-4-(4-chlorobenzyl)-1-methyl-6-oxa-bicyclo[3,2,0]heptane-5-carboxylic acid methyl ester (Compound 7-1)

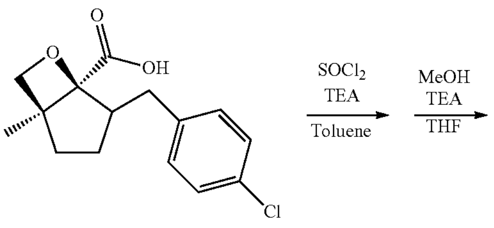

13-1

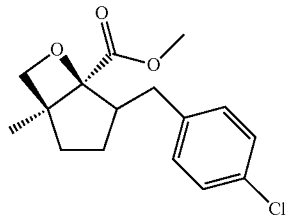

7-1

In 2 ml of toluene, 50 mg of Compound 13-1 synthesized in Production Example 26 was dissolved. To the solution thus obtained, 0.06 ml of triethylamine was added, and the resulting mixture solution was then cooled. To the solution thus cooled, 0.02 ml of thionyl chloride was added, and the resulting mixture solution was stirred for 1 hour while being allowed to reach room temperature. After the reaction, triethylamine hydrochloride generated was removed by filtration from the reaction solution, and the solvent was then distilled away under a reduced pressure to obtain 73 mg of crude product. To the crude product, 2 ml of tetrahydrofuran, 0.05 ml of triethylamine, and 0.05 ml of methanol were added, and the resulting mixture was stirred at room temperature for 0.5 hour. After the reaction, an aqueous solution of diluted sulphuric acid was added to the reaction solution thus obtained, and extraction with ethyl acetate was then carried out. The organic layer was washed with saturated brine and then dried over anhydrous sodium sulfate. The solvent was distilled away under a reduced pressure to obtain 58 mg of Compound 7-1.

The following shows the analysis result (Note that a 1,5-cis form of Compound 7-1 is as mentioned previously.).

(1,5-trans Form)

$^1$H-NMR ($CDCl_3$) δ=

1.35 (3H, s), 1.64-1.85 (3H, m), 2.24-2.27 (1H, m), 2.32 (1H, dd, J=15.5, 12.8 Hz), 2.49-2.58 (2H, m), 3.74 (3H, s), 4.19 (1H, d, J=5.7 Hz), 4.29 (1H, dd, J=5.7, 1.2 Hz), 7.05 (2H, d, J=8.4 Hz), 7.25 (2H, d, J=8.4 Hz).

Production Example 28

Synthesis 1 of (1RS,5RS)-4-(4-chlorobenzyl)-1-methyl-6-oxa-bicyclo[3,2,0]heptane-5-methyl alcohol (Compound 8-1)

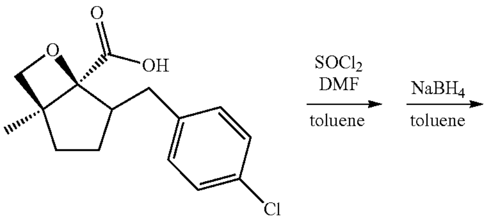

13-1

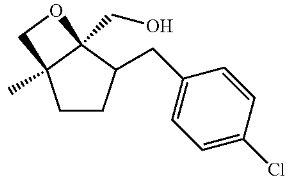

8-1

In 2 ml of toluene, 100 mg of Compound 13-1 obtained in Production Example 26 was dissolved. To the solution thus obtained, two drops of DMF and 0.05 ml of thionyl chloride were added. The resulting mixture solution was stirred at room temperature for 4 hours, and the solvent was distilled away under a reduced pressure to obtain a crude product of acid chloride. The crude product was dissolved in 2 ml of toluene. To the solution thus obtained, 30 mg of sodium borohydride was added, and the resulting mixture solution was stirred at room temperature for 1.3 hours. To the reaction solution thus obtained, 20 mg of sodium borohydride was added, and the resulting mixture solution was further stirred at room temperature for 0.5 hour. The reaction solution was cooled to 0° C. and then mixed with methanol and purified water to stop the reaction. The resulting solution was subjected to extraction with ethyl acetate. The organic layer thus extracted was washed with saturated brine and then dried over anhydrous sodium sulfate, and the solvent was distilled away under a reduced pressure. The residue was purified by silica gel column chromatography to obtain 91 mg of Compound 8-1.

Example 3

Production Example 29

Synthesis of (1RS,5RS)-4-(4-chlorobenzyl)-1-methyl-6-oxa-bicyclo[3,2,0]heptane-5-carbaldehyde (Compound 15-1)

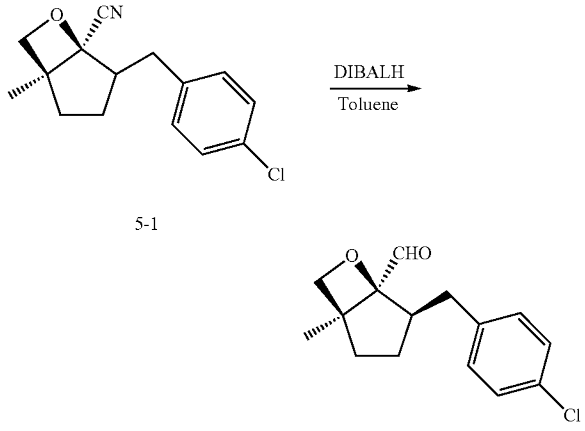

5-1

15-1

In 12 ml of toluene, 267 mg of Compound 5-1 obtained in Production Example 9 of Example 1 described above was dissolved. The solution thus obtained was then cooled to −78° C. To the solution thus cooled, 1.2 ml of hexane solution of 1.0M diisobutylaluminum hydride was added dropwise. Thereafter, the resulting mixture solution was stirred for 1 hour. After the reaction, 1 ml of methanol and 10 ml of 10% aqueous solution of tartaric acid were added to the reaction solution thus obtained. The resulting mixture solution was stirred for 0.5 hour while being allowed to reach room temperature. The reaction solution thus obtained was mixed with saturated brine, and extraction with ethyl acetate was then carried out. The organic layers thus extracted were blended with each other and then washed with saturated brine. Thereafter, the organic layers were dried over anhydrous sodium sulfate, and the solvent was distilled away under a reduced pressure. The residue was purified by silica gel column chromatography to obtain 184 mg of Compound 15-1.

The following shows the analysis result.

$^1$H-NMR ($CDCl_3$): δ=

1.13 (3H, s), 1.46-1.51 (1H, m), 1.78-1.83 (1H, m), 1.98-2.07 (2H, m), 2.52-2.57 (1H, m), 2.67 (1H, d, J=2.8 Hz), 2.69 (1H, d, J=3.05 Hz), 4.40 (1H, d, J=6.0 Hz), 4.44 (1H, dd, J=6.0, 1.3 Hz), 7.04 (2H, d, J=8.4 Hz), 7.21 (1H, d, J=8.4 Hz), 9.60 (1H, s).

Production Example 30

Synthesis 2 of Compound 8-1

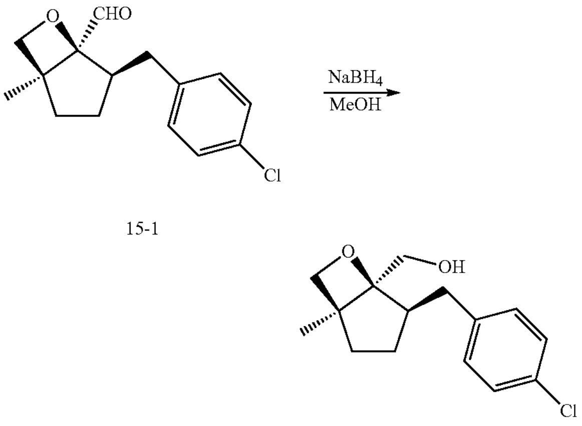

15-1

8-1

In 3 ml of methanol, 76 mg of Compound 15-1 synthesized in Production Example 29 was dissolved. Thereafter, the solution thus obtained was cooled in ice bath. The solution thus cooled was stirred for 6 hours with addition of 73 mg of sodium borohydride thereto in four portions. After the reaction, purified water and 10% tartaric acid were added to the reaction solution thus obtained, and the resulting mixture solution was stirred for 10 minutes. To the reaction solution thus obtained, saturated brine was added, and extraction with ethyl acetate was then carried out. The organic layers thus extracted were blended with each other and then washed with saturated brine. Thereafter, the organic layers were dried over anhydrous sodium sulfate. The solvent was distilled away under a reduced pressure to obtain 83 mg of Compound 8-1.

Example 4

In similar methods with the production examples of the above Examples, compounds represented by Formula (11a) below were synthesized, wherein their respective combinations of $R^1$, Ar, A, and $X^4$ were as listed in Tables 6 and 7.

TABLE 6

(11a)

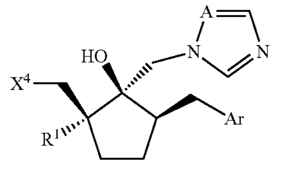

| Compound No. | $R^1$ | A | Ar | $X^4$ |
|---|---|---|---|---|
| 11a-6 | $CH_3$ | N | 3-ChloroPhenyl | Cl |
| 11a-13 | $CH_3CH_2$ | N | Phenyl | Cl |
| 11a-24 | $CH_3OCH_2$ | N | 4-ChloroPhenyl | Cl |
| 11a-25 | $CH_3OCH_2$ | N | 4-FluoroPhenyl | Cl |

TABLE 6-continued (11a)

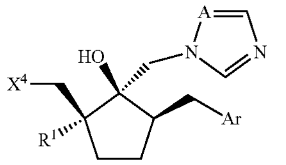

| Compound No. | $R^1$ | A | Ar | $X^4$ |
|---|---|---|---|---|
| 11a-26 | $CH_3OCH_2$ | N | Phenyl | Cl |
| 11a-27 | $CH_3CH_2OCH_2$ | N | 4-ChloroPhenyl | Cl |
| 11a-28 | $CH_3CH_2OCH_2$ | N | 4-FluoroPhenyl | Cl |
| 11a-29 | $CH_3CH_2OCH_2$ | N | Phenyl | Cl |
| 11a-30 | $CH_3$ | N | 4-ChloroPhenyl | Br |
| 11a-35 | $CH_3OCH_2$ | N | 4-FluoroPhenyl | Br |
| 11a-36 | $CH_3OCH_2$ | N | Phenyl | Br |

TABLE 7

| Compound No. | $R^1$ | A | Ar | $X^4$ |
|---|---|---|---|---|
| 11a-14 | $CH_3CH_2$ | N | 4-FluoroPhenyl | Cl |
| 11a-15 | $CH_3CH_2CH_2$ | N | 4-FluoroPhenyl | Cl |
| 11a-16 | $CH_3CH_2CH_2$ | N | 4-ChloroPhenyl | Cl |
| 11a-17 | $CH_3$ | N | 4-TrifluoromethylPhenyl | Cl |
| 11a-18 | $CH_3$ | N | 4-BromoPhenyl | Cl |
| 11a-19 | $CH_3$ | N | 3-FluoroPhenyl | Cl |
| 11a-20 | $CH_3$ | N | 2-ChloroPhenyl | Cl |
| 11a-21 | $CH_3$ | N | 2,4-Difluoro-Phenyl | Cl |
| 11a-22 | $CH_3$ | N | 2-Naphthyl | Cl |
| 11a-23 | $CH_3$ | N | 1-Benzothiophen-5-yl | Cl |
| 11a-37 | $CH_3OCH_2$ | N | 4-ChloroPhenyl | Br |

INDUSTRIAL APPLICABILITY

The present invention is suitably applicable to the production of (i) a compound that can be used as an active ingredient of agro-horticultural bactericides, plant growth regulators and industrial material protecting agents and (ii) an intermediate thereof.

The invention claimed is:

1. A method for producing an oxetane compound represented by Formula (II) shown below, comprising the step of: contacting a compound of Formula (I) with a cyanide salt, a compound represented by Formula (I):

(I)

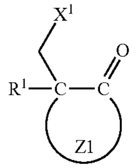

wherein $R^1$ is selected from a hydrogen atom and a linear or branched $C_1$-$C_6$ alkyl group; a hydrogen atom(s) contained in the alkyl group may be substituted with a $C_1$-$C_4$ alkoxy group; $X^1$ is selected from a halogen atom and —$OSO_2R^3$ where $R^3$ is selected from a $C_1$-$C_3$ alkyl group, a phenyl group, and a naphthyl group; a hydrogen atom(s) contained in the alkyl group may be substituted with a halogen atom; a hydrogen atom(s) contained in the phenyl group and the naphthyl group may be substituted with a halogen atom, a methyl group, a trifluoromethyl group, a nitro group, or an amino group; and a ring Z1 represents a $C_5$-$C_8$ cyclic hydrocarbon having a ring structure which includes (i) a carbon atom bonded to $R^1$ and (ii) a carbonyl carbon atom, where a hydrogen atom(s) contained in the cyclic hydrocarbon may be substituted with an aliphatic hydrocarbon group, an aromatic hydrocarbon group, an aromatic heterocyclic group, an aliphatic hydrocarbon group in which a hydrogen atom is substituted with an aromatic hydrocarbon group or an aromatic heterocyclic group; an alkoxylalkyl group, a carbonyloxyalkyl group, and an amido group, to obtain the oxetane compound represented by Formula (II):

(II)

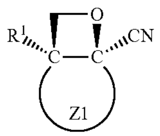

wherein $R^1$ and a ring Z1 are identical to $R^1$ and the ring Z1 in Formula (I), respectively.

2. A method for producing an oxetane compound represented by Formula (V) shown below, comprising the steps of: contacting a compound of Formula (III) with a cyanide salt, a compound represented by Formula (III):

(III)

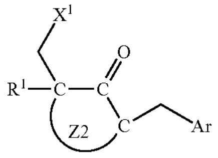

wherein $R^1$ is selected from a hydrogen atom and a linear or branched $C_1$-$C_6$ alkyl group; a hydrogen atom(s) contained in the alkyl group may be substituted with a $C_1$-$C_4$ alkoxy group; $X^1$ is selected from a halogen atom and —$OSO_2R^3$ where $R^3$ is selected from a $C_1$-$C_3$ alkyl group, a phenyl group, and a naphthyl group; a hydrogen atom(s) contained in the alkyl group may be substituted with a halogen atom; a hydrogen atom(s) contained in the phenyl group and the naphthyl group may be substituted with a halogen atom, a methyl group, a trifluoromethyl group, a nitro group, or an amino group; Ar is selected from a $C_6$-$C_{10}$ aromatic hydrocarbon group and a 5 to 10-membered aromatic heterocyclic group having a hydrogen atom(s) both of which may be substituted with a halogen atom, a phenyl group, a $C_1$-$C_4$ alkyl group, a $C_1$-$C_4$ haloalkyl group, a $C_1$-$C_4$ alkoxy group, and a $C_1$-$C_4$ haloalkoxy group; and a ring Z2 represents a $C_5$-$C_8$ cyclic hydrocarbon having a ring structure which includes (i) a carbon atom bonded to $R^1$, (ii) a carbonyl carbon atom, and (iii) a carbon atom bonded to —$CH_2$—Ar, where a hydrogen atom(s) contained in the cyclic hydrocarbon may be substituted with an aliphatic hydrocarbon group, an aromatic hydrocarbon group in which a hydrogen atom is substituted with an aromatic hydrocarbon group or an aromatic heterocyclic group, an alkoxylalkyl group, a carbonyloxyalkyl group, and an amido group, to obtain an oxetane compound represented by Formula (IV):

(IV)

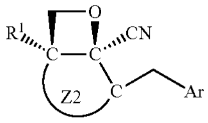

wherein $R^1$, a ring Z2, and Ar are identical to $R^1$, the ring Z2, and Ar in Formula (III) shown above, respectively; and contacting the oxetane compound represented by Formula (IV) shown above with an alkoxide, to obtain the oxetane compound represented by Formula (V):

(V)

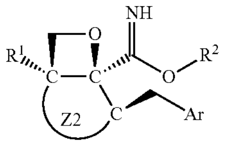

wherein $R^1$, a ring Z2, and Ar are identical to $R^1$, the ring Z2, and Ar in Formula (III) shown above, respectively, and $R^2$ represents a linear or branched $C_1$-$C_6$ alkyl group.

3. The method according to claim 1, wherein the compound represented by Formula (I) is a compound represented by Formula (4):

(4)

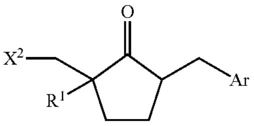

wherein $R^1$ represents a linear or branched $C_1$-$C_6$ alkyl group; a hydrogen atom(s) contained in the alkyl group may be substituted with a $C_1$-$C_4$ alkoxy group; $X^2$ is selected from a halogen atom and —$OSO_2R^3$ where $R^3$ is selected from a $C_1$-$C_3$ alkyl group, a phenyl group, and a naphthyl group, and a hydrogen atom(s) contained in any one of the alkyl group, the phenyl group, and the naphthyl group may be substituted as in claim 1; and Ar is selected from a $C_6$-$C_{10}$ aromatic hydrocarbon group and a 5 to 10-membered aromatic heterocyclic group having a hydrogen atom(s) both of which may be substituted with a halogen atom, a phenyl group, a $C_1$-$C_4$ alkyl group, a $C_1$-$C_4$ haloalkyl group, a $C_1$-$C_4$ alkoxy group, and a $C_1$-$C_4$ haloalkoxy group, and the compound represented by Formula (II) is a compound represented by Formula (5):

(5)

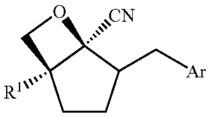

wherein $R^1$ and Ar are identical to $R^1$ and Ar in Formula (4) shown above, respectively.

4. The method according to claim 2, wherein the compound represented by Formula (III) is a compound represented by Formula (4):

(4)

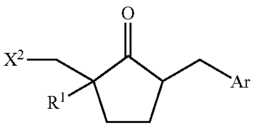

wherein $R^1$ represents a linear or branched $C_1$-$C_6$ alkyl group; a hydrogen atom(s) contained in the alkyl group may be substituted with a $C_1$-$C_4$ alkoxy group; $X^2$ is selected from a halogen atom and —$OSO_2R^3$ where $R^3$ is selected from a $C_1$-$C_3$ alkyl group, a phenyl group, and a naphthyl group, and a hydrogen atom(s) contained in any one of the alkyl group, the phenyl group, and the naphthyl group may be substituted as in claim 2; and Ar is selected from a $C_6$-$C_{10}$ aromatic hydrocarbon group and a 5 to 10-membered aromatic heterocyclic group having a hydrogen atom(s) both of which may be substituted as in claim 2, the compound represented by Formula (IV) is a compound represented by Formula (5):

(5)

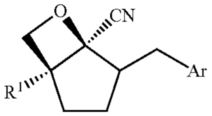

wherein $R^1$ and Ar are identical to $R^1$ and Ar in Formula (4) shown above, respectively, and the compound represented by Formula (V) is a compound represented by Formula (6a):

(6a)

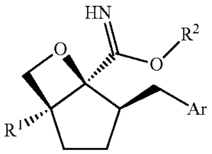

wherein $R^1$ and Ar are identical to $R^1$ and Ar in Formula (4) shown above, respectively, and $R^2$ represents a linear or branched $C_1$-$C_6$ alkyl group.

5. The method according to claim 2, wherein

Ar in Formulae (III), (IV), and (V) is represented by any one of Formulae (a) through (d):

(a)

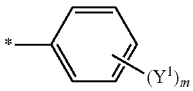

-continued (b)

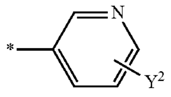

(c)

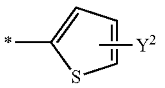

(d)

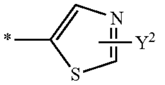

wherein $Y^1$ is selected from a halogen atom, a $C_1$-$C_3$ alkyl group, and a $C_1$-$C_3$ haloalkoxy group, m is selected from 0, 1, and 2, $Y^2$ represents a halogen atom, and * represents bonding to the methylene group of formula (III), (IV), or (V).

6. The method according to claim 3, wherein

Ar in Formulae (4) and (5) is represented by any one of Formulae (a) through (d):

(a)

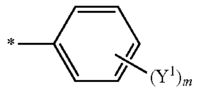

(b)

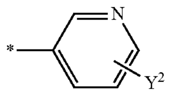

(c)

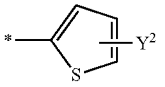

(d)

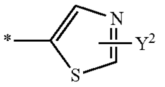

wherein $Y^1$ is selected from a halogen atom, a $C_1$-$C_3$ alkyl group, and a $C_1$-$C_3$ haloalkoxy group, m is selected from 0, 1, and 2, $Y^2$ represents a halogen atom, and * represents bonding to the methylene group of formula (III), IV) or (V).

7. A method for producing an azolylmethylcyclopentanol compound represented by Formula (11):

(11)

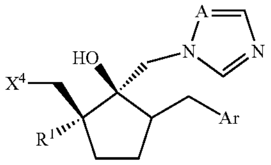

wherein $R^1$ and Ar are identical to $R^1$ and Ar in Formula (4), respectively, $X^4$ represents a halogen atom, and A is selected from a nitrogen atom and a methine group, the method comprising:

the method according to claim 3;

contacting the oxetane compound represented by Formula (5) to hydrolyze in a solvent in the presence of a base to obtain the oxetane compound represented by Formula (12):

(12)

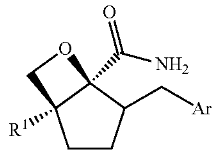

contacting the oxetane compound represented by Formula (12) with a nitrogen oxide and then subjecting to carboxylation with denitrification or carrying out hydrolysis with use of a high concentration aqueous solution of hydroxide to obtain the oxetane compound represented by Formula (13);

(13)

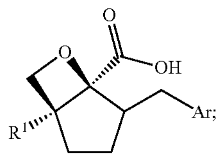

contacting the oxetane compound represented by Formula (13) with an acid catalyst in an alcohol solvent or a base or preparing an acid halide and subjecting the prepared acid halide to an alcohol solvent to obtain the oxetane compound represented by Formula (7);

(7)

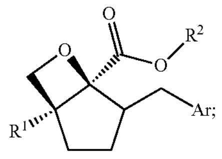

contacting the oxtene compound represented by Formula (7) with a reducing agent, to obtain the oxetane compound represented by Formula (8a):

(8a)

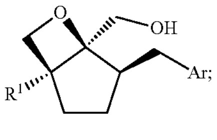

contacting the oxetane compound represented by Formula (8a) with a sulfonyl chloride in a solvent in the presence of an excessive amount of base or with a thionyl halide, to obtain the oxetane compound represented by Formula (9a):

(9a)

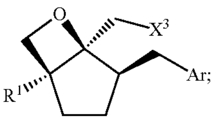

contacting the oxetane compound represented by Formula (9a) with an imidazole compound or a triazole compound, in a solvent, in the presence of a base to obtain the oxetane compound represented by Formula (10a):

(10a)

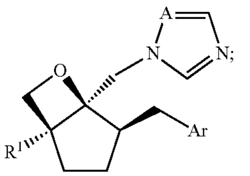

and

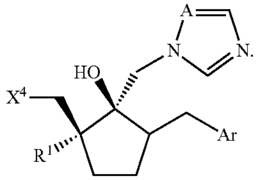

(11)

contacting the oxetane compound represented by Formula (10a) with a halogen acid in a solvent to produce a halogenated methyl group and a tertiary hydroxyl group to obtain the compound represented by Formula (11):

8. A method for producing an azolylmethylcyclopentanol compound represented by Formula (11a):

(11a)

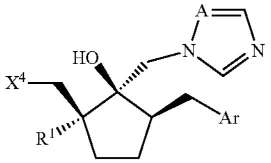

wherein $R^1$ and Ar are identical to $R^1$ and Ar in Formula (4), respectively, $X^4$ represents a halogen atom, and A is selected from a nitrogen atom and a methine group, the method comprising:

the method according to claim 4, contacting the oxetane compound represented by Formula (6a) with an acid catalyst to add an acid and then removing the ammonium to obtain the oxetane compound represented by Formula (7a):

(7a)

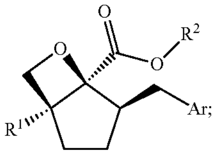

contacting the oxtene compound represented by Formula (7a) with a reducing agent, to obtain the oxetane compound represented by Formula (8a):

(8a)

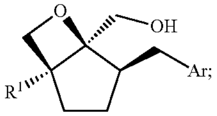

contacting the oxetane compound represented by Formula (8a) with a sulfonyl chloride in a solvent in the presence of an excessive amount of base or with a thionyl halide, to obtain the oxetane compound represented by Formula (9a):

(9a)

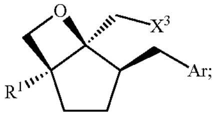

contacting the oxetane compound represented by Formula (9a) with an imidazole compound or a triazole compound, in a solvent, in the presence of a base to obtain the oxetane compound represented by Formula (10a):

(10a)

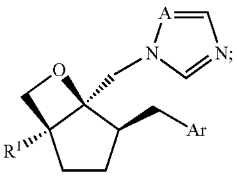

and contacting the oxetane compound represented by Formula (10a) with a halogen acid in a solvent to produce a halogenated methyl group and a tertiary hydroxyl group to obtain the compound represented by Formula (11a):

(11a)

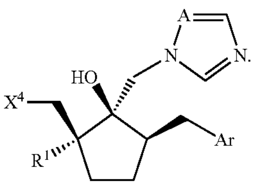

9. A method for producing an azolylmethylcyclopentanol compound represented by Formula (11):

(11)

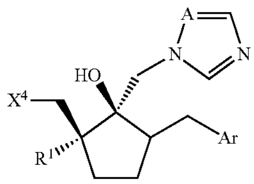

wherein $R^1$ and Ar are identical to $R^1$ and Ar in Formula (4), respectively, $X^4$ represents a halogen atom, and A is selected from a nitrogen atom and a methine group, the method comprising:

the method according to claim 3;

contacting the oxetane compound represented by Formula (5) to reduce and hydrolyze diisobutylaluminum hydride to obtain the oxetane compound represented by Formula (15):

(15)

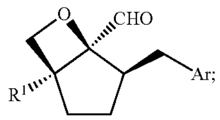

contacting the oxetane compound represented by Formula (15) with a reducing agent to obtain the oxetane compound represented by Formula (8a);

(8a)

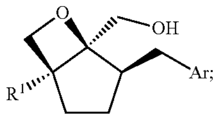

contacting the oxetane compound represented by Formula (8a) with a sulfonyl chloride in a solvent in the presence of an excessive amount of base or with a thionyl halide to obtain the oxetane compound represented by Formula (9a):

(9a)

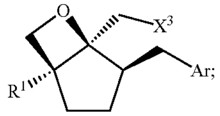

contacting the oxetane compound represented by Formula (9a) with an imidazole compound or a triazole compound, in a solvent, in the presence of a base, to obtain the oxetane compound represented by Formula (10a):

(10a)

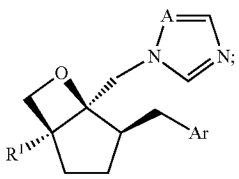

and contacting the oxetane compound represented by Formula (10a) with a halogen acid in a solvent to produce a halogenated methyl group and a tertiary hydroxyl group to obtain the compound represented by Formula (11):

(11)

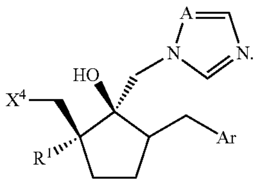

10. A method according to claim 1, wherein the contacting is in the presence of a solvent selected from an aromatic hydrocarbon, ether, amide, alcohol, dimethyl sulfoxide, water and a mixture of at least two of the previous.

11. A method according to claim 10, wherein the contacting takes place at a temperature of 10 degrees Celsius to 150 degrees Celsius.

12. A method according to claim 11, wherein the cyanide salt is selected from sodium cyanide, potassium cyanide, calcium cyanide, and tetrabutyl cyanide.

* * * * *